United States Patent
Wilkinson et al.

(10) Patent No.: US 9,492,183 B2
(45) Date of Patent: Nov. 15, 2016

(54) PATIENT-MATCHED INSTRUMENTATION AND METHODS

(75) Inventors: Zachary Christopher Wilkinson, Germantown, TN (US); Brian W. McKinnon, Bartlett, TN (US); David Timothy Mehl, Memphis, TN (US); Luke Andrew Gibson, Sothaven, MS (US);

(Continued)

(73) Assignee: Smith & Nephew, Inc., Memphis, TN (US)

(*) Notice: Subject to any disclaimer, the term of this patent is extended or adjusted under 35 U.S.C. 154(b) by 628 days.

(21) Appl. No.: 13/821,582

(22) PCT Filed: Oct. 14, 2011

(86) PCT No.: PCT/US2011/056380
§ 371 (c)(1),
(2), (4) Date: Sep. 25, 2013

(87) PCT Pub. No.: WO2012/051542
PCT Pub. Date: Apr. 19, 2012

(65) Prior Publication Data
US 2014/0066720 A1  Mar. 6, 2014

Related U.S. Application Data

(60) Provisional application No. 61/393,175, filed on Oct. 14, 2010.

(51) Int. Cl.
*A61B 17/17* (2006.01)
*A61B 17/02* (2006.01)
(Continued)

(52) U.S. Cl.
CPC .......... *A61B 17/1703* (2013.01); *A61B 17/02* (2013.01); *A61B 17/157* (2013.01);
(Continued)

(58) Field of Classification Search
CPC .................... A61B 17/17; A61B 17/02; A61B 17/1703; A61B 17/56
(Continued)

(56) References Cited

U.S. PATENT DOCUMENTS

| 2007/0226986 | A1* | 10/2007 | Park | A61B 17/155 29/592 |
| 2008/0243127 | A1* | 10/2008 | Lang | A61B 5/4528 606/87 |

(Continued)

OTHER PUBLICATIONS

Japanese Patent Office, First Office Action, dated Sep. 7, 2015, with English translation, 8 pages.
(Continued)

*Primary Examiner* — Christopher Beccia
(74) *Attorney, Agent, or Firm* — David A. Chambers, Esq.

(57) ABSTRACT

A patient-matched cutting block including a surface or point contact features adapted to at least partially conform to or reference a patient specific anatomy. The cutting block having guide slots configured for guiding the movement of cutting tools relative to the patient specific anatomy or features configured to mate to and guide standard cutting guides relative to patient specific anatomy in order to form plateau and eminence resections of the patient specific anatomy.

14 Claims, 68 Drawing Sheets

(75) Inventors: Scott Kennedy Laster, Memphis, TN (US)

(51) Int. Cl.
*A61B 17/15* (2006.01)
*A61B 17/32* (2006.01)
*A61B 17/56* (2006.01)
*A61F 2/38* (2006.01)

(52) U.S. Cl.
CPC ............... *A61B 2017/320052* (2013.01); *A61B 2017/568* (2013.01); *A61F 2/38* (2013.01)

(58) Field of Classification Search
USPC .......................................... 606/86 R, 87–89
See application file for complete search history.

(56) References Cited

U.S. PATENT DOCUMENTS

2008/0275452 A1* 11/2008 Lang ...................... A61B 17/15
606/88
2009/0088758 A1* 4/2009 Bennett ................ A61B 17/155
606/82

OTHER PUBLICATIONS

Australian Patent Office, Patent Examination Report No. 1, dated Mar. 7, 2014, 5 pages.
European Patent Office, European Search Report, Feb. 17, 2014, 7 pages.
Chinese Patent Office, First Office Action, dated Jan. 19, 2015, with English translation, 25 pages.
Chinese Patent Office, Second Office Action, dated Nov. 16, 2015, with English translation, 17 pages.

* cited by examiner

PATIENT-MATCHED INSTRUMENTATION AND METHODS

CROSS REFERENCE TO RELATED APPLICATION

This application is a United States National Phase filing of International Application No. PCT/US11/056380 filed on Oct. 14, 2011 which claims priority to and the full benefit of U.S. Provisional Application Ser. No. 61/393,175, filed Oct. 14, 2010, and titled "Patient-Matched Instrumentation and Methods," the entire contents of which are incorporated herein by reference.

TECHNICAL FIELD

This disclosure relates to patient-matched instrumentation.

BACKGROUND

Patient-matched or patient-specific implant guides are used during orthopaedic procedures to accurately insert pins, guide cuts, and place implants. The patient-matched guides are generally based on data received from an MRI or CT scan of the patient and rely on matching an anatomic feature for correct positioning of the guide during a surgical procedure.

Generally these patient matched guides are held in place by pins or screws to reduce the risk of slipping during surgery. Pins are typically inserted into healthy bone outside of the resection area to ensure continued stability and to avoid interference with surgical instruments used during the procedure.

There remains a need for a less damaging solution that reduces the amount of damage to healthy bone and retains at least a portion of the tibial eminence during use of surgical instrument guides while maintaining the ease of use and speed associated with patient-matched guides.

There also remains a need for improved structural rigidity of the features guiding cutting tools relative to patient specific anatomy.

There also remains a need for a means within patient matched instrumentation of making resections which result in the appropriate balance soft tissue tension.

There also remains a need for patient matched instrumentation able to orient and guide the additional resections required for preserving at least a portion of the proximal tibia.

SUMMARY

In one general aspect, a patient matched cutting block includes a surface or point feature adapted to at least partially conform to or reference a patient specific anatomy, and a plurality of guide slots configured for guiding the movement of cutting tools relative to the patient specific anatomy to form plateau and eminence resections of the patient's anatomy.

Implementations can optionally include one or more of the following features. For example, the patient specific surface or point contact feature is established in pre-surgical planning based on imaging data of the patient's anatomy. The patient matched cutting block further includes one or more apertures configured to guide the placement of provisional fixation pins, and wherein the apertures contain position control elements configured to control the depth of the provisional fixation pins. The patient matched cutting block may further comprise retractor features detachably coupled to the cutting block and configured to retain soft tissue away from the guide slots. The plurality of guide slots may include surfaces that facilitate horizontal medial and lateral plateau resections and medial and lateral vertical eminence resections of a proximal tibia. The patient matched cutting block may further comprise guide slots for facilitating vertical and horizontal anterior tibial eminence resections of the proximal tibia.

In another general aspect, a patient specific tibial cutting guide includes a central portion configured to at least partially overlay anterior and superior portions of the proximal tibia, a plurality of outrigger portions extending from the central portion and configured to at least partially overlay medial and lateral articulation surfaces of the proximal tibia, and a plurality of wing portions extending medially and laterally from the central portion and configured to extend at least partially around medial and lateral sides of an anterior face of the proximal tibia, wherein the central portion and the plurality of outrigger portions define guides configured for guiding a cutting tool to form vertical and anterior eminence resections of the proximal tibia and the plurality of wing portions define guide slots for guiding a cutting tool to form horizontal plateau resections of the proximal tibia.

Implementations can optionally include one or more of the following features. For example, one or more of the central portion, the plurality of outrigger portions, and the plurality of wing portions may include one or more surfaces or point contacts adapted to at least partially conform to or reference a corresponding surface of the proximal tibia. The one or more surfaces or point contacts is established in pre-surgical planning based on imaging data of the patient's proximal tibia. The patient specific tibial cutting guide may further comprise one or more apertures defined in the central portion or the plurality of outrigger portions and configured to guide the placement of provisional fixation pins. The plurality of wing portions may include retractor features configured to retain soft tissue away from the guide slots. The patient specific tibial cutting guide may further comprise reinforcing elements at least partially embedded in one or more of the central portion, the plurality of outrigger portions, or the plurality of wing portions.

In another general aspect, a system includes a patient matched cutting block or a patient specific tibial cutting guide and a standard instrument attachable to the patient matched cutting block or the patient specific tibial cutting guide to assist in the configuration of and guidance of a cutting tool during a bone resection procedure.

In another general aspect, a method of resectioning a proximal tibia includes securing a patient matched instrument to a patient's proximal tibia and using the patient matched instrument to guide one or more cutting guides relative to the proximal tibia to form horizontal medial and lateral plateau resections, medial and lateral vertical eminence resections.

Implementations can optionally include one or more of the following features. For example, securing the patient matched instrument to the patient's proximal tibia may comprise using one or more fixation pins to secure the instrument in a particular location relative to the tibia, and wherein one or more holes formed in the tibia during the securing step are removed during resectioning.

Instrumentation and methods, including patient-matched instrumentation and methods, for facilitating orthopaedic procedures including knee arthroplasty procedures such as bi-cruciate retaining knee arthroplasty procedures are further described herein.

It should be understood that the drawings are not necessarily to scale and that the disclosed implementations are sometimes illustrated diagrammatically and in partial views. In certain instances, details which are not necessary for an understanding of the disclosure or which render other details difficult to perceive may have been omitted. It should be understood, of course, that this disclosure is not limited to the particular implementations illustrated herein.

DETAILED DESCRIPTION

Figure 1:
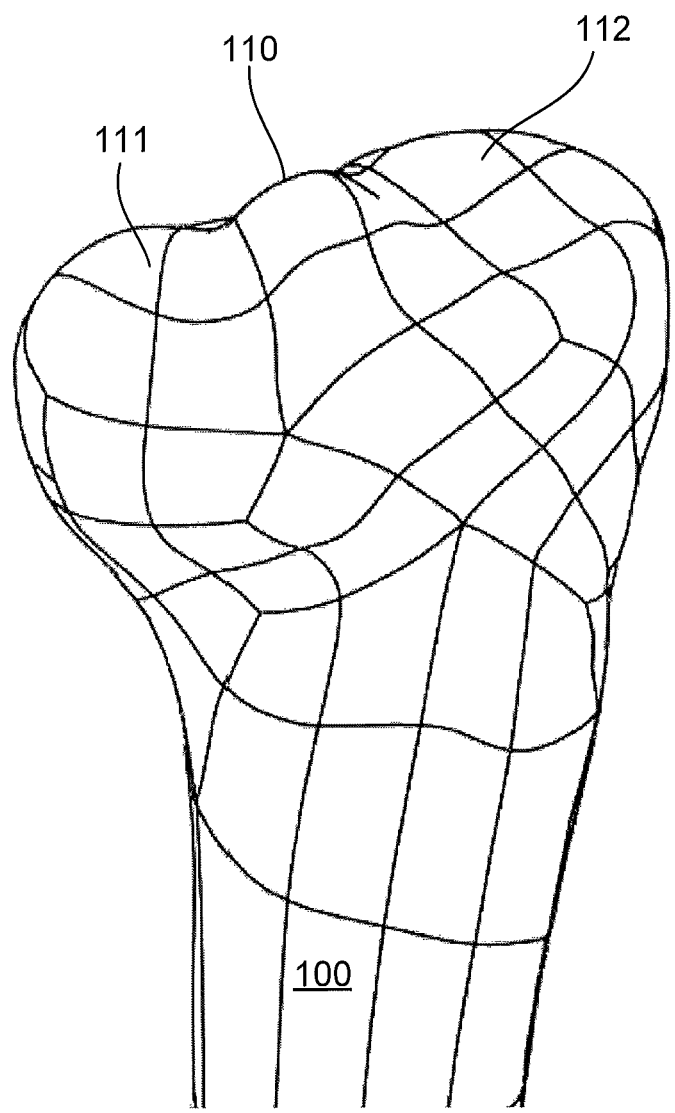
FIG. 1 shows an unresected, proximal tibia.

FIG. 1 shows a proximal portion of a tibia 100 including, among other things, a tibial eminence 110 that is flanked on a medial side by a medial articulation surface 111 for articulation with a medial femoral condyle and flanked on a lateral side by a lateral articulation surface 112 for articulation with a lateral femoral condyle. The tibial eminence 110, among other things, may provide attachment sites for anterior and posterior cruciate ligaments. Other anatomy, although not necessarily specifically shown, may also be present, such as a meniscus, patellar tendon, collateral ligaments, and other soft tissues.

As shown in later figures and described below, in some knee arthroplasty procedures, one or more portions of the proximal tibia are resected to facilitate the positioning and/or attachment of orthopaedic implants such as tibial baseplates and/or separate or integral tibial inserts. In some implementations, such as those relating to bi-cruciate retaining knee arthroplasty procedures discussed below, the medial and lateral articular surfaces, as well as an anterior portion of the tibial eminence, are resected, while a substantial portion of the tibial eminence remains, including, in some implementations, portions of the tibial eminence 110 functioning as anterior and posterior cruciate ligament attachment sites. In some instances, properly positioning and orienting these resections to achieve optimal positions and orientations for the tibial implant(s) can be difficult and time consuming.

Figure 2:
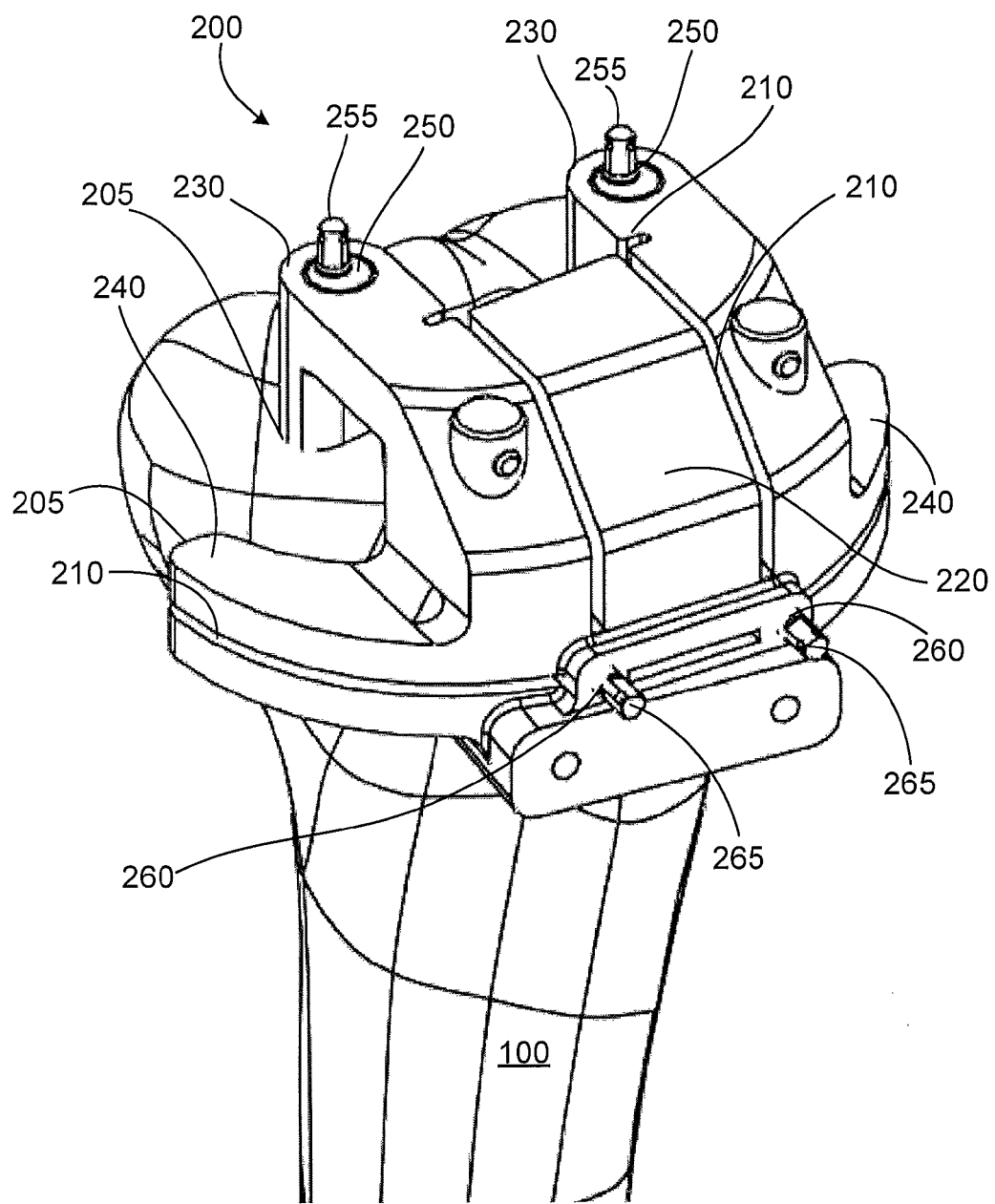
FIG. 2 shows one implementation of a patient-matched cutting guide positioned on the proximal tibia of FIG. 1.

FIG. 2 shows a patient-matched instrument 200 positioned on the proximal tibia of FIG. 1. The patient-matched instrument 200 shown in FIG. 2 is a tibial cutting guide with a plurality of slots and other guide surfaces for guiding the movement of cutting tools such as reciprocating and oscillating saw blades with respect to the proximal tibia. In the particular implementation shown in FIG. 2, the tibial cutting guide 200 includes guide surfaces 210 for guiding horizontal medial and lateral plateau resections, medial and lateral vertical eminence resections, and vertical and horizontal anterior tibial eminence resections. The tibial cutting guide 200 of FIG. 2, when properly positioned and oriented on the patient's tibia, establishes the positions and orientations of these six resections. As discussed in more detail below, the tibial cutting guide 200 of FIG. 2 includes several surfaces 205 that are adapted to at least somewhat conform to or reference the unique geometry of the particular patient's anatomy, these surfaces 205 substantially facilitating a precise or substantially precise positioning and orienting of the patient-matched instrument of the patient's anatomy with respect to a desired position and orientation, which, in some implementations, may have been established in pre-surgical planning stages based on imaging data of the patient's specific anatomy or other information.

Other implementations can include patient-matched tibial cutting guides, other cutting guides, and other surgical instrumentation for guiding other resections or other bone modifications with respect to a particular patient's anatomy. Other implementations may include different numbers, positions and orientations of cutting guide slots or other guide surfaces or point contact features, such as, for example, a probe having a small radius (i.e., a radius less than the radius of the anatomy contacted) that without deformation, contacts the anatomy in a single point, as desired.

The patient-matched tibial cutting guide 200 shown in FIG. 2 includes a central portion 220 overlying to at least some extent anterior and superior portions of the proximal tibia, two outrigger portions 230 extending from the central portion over the medial and lateral articulation surfaces, and two wings 240 extending medially and laterally from the central portion around medial and lateral sides of the anterior face of the tibia. In this particular implementation, the central portion 220 and outriggers 230 define guide slots and other guide surfaces 210 for the vertical eminence and anterior eminence resections, and the two wings 240 define guide slots 210 for the horizontal plateau resections. The tibial cutting guide 200 shown in FIG. 2 includes guide surfaces 210 that are captured to at least some extent. Other implementations of patient-matched instruments may include slots or other guide surfaces or structures that are completely captured, not captured at all, or other combinations.

Figure 3:
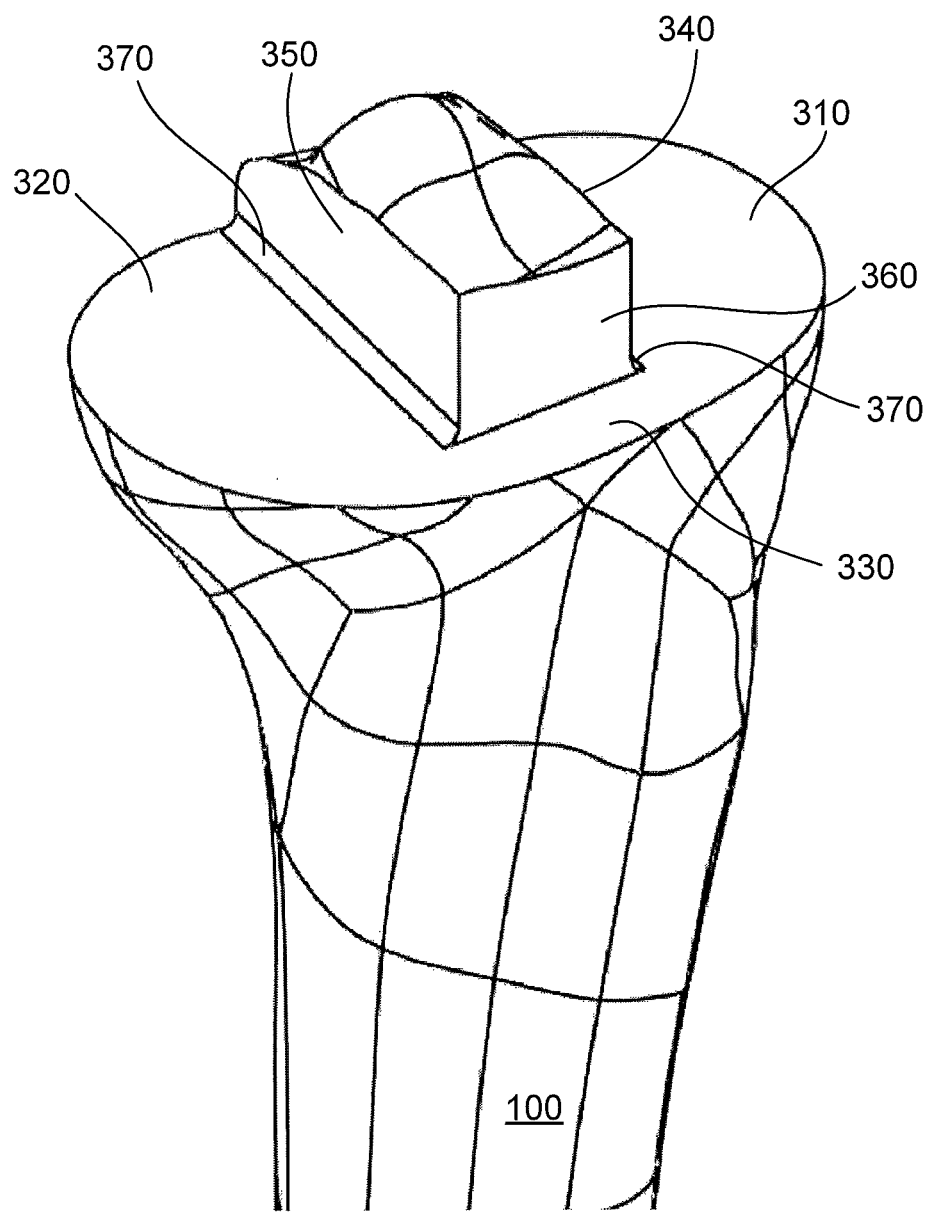
FIG. 3 shows the proximal tibia of FIG. 1 after resection.
Figure 4:
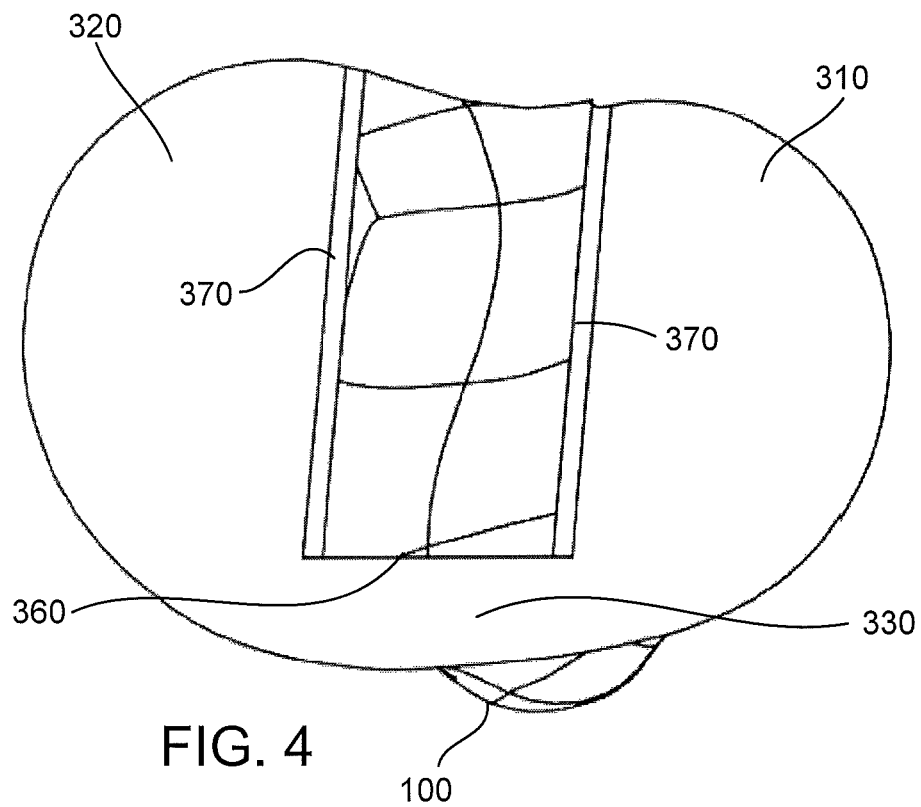
FIG. 4 is a top plan view of the resected proximal tibia of FIG. 3, and a cutting profile for a vertical anterior eminence resection.
Figure 5:
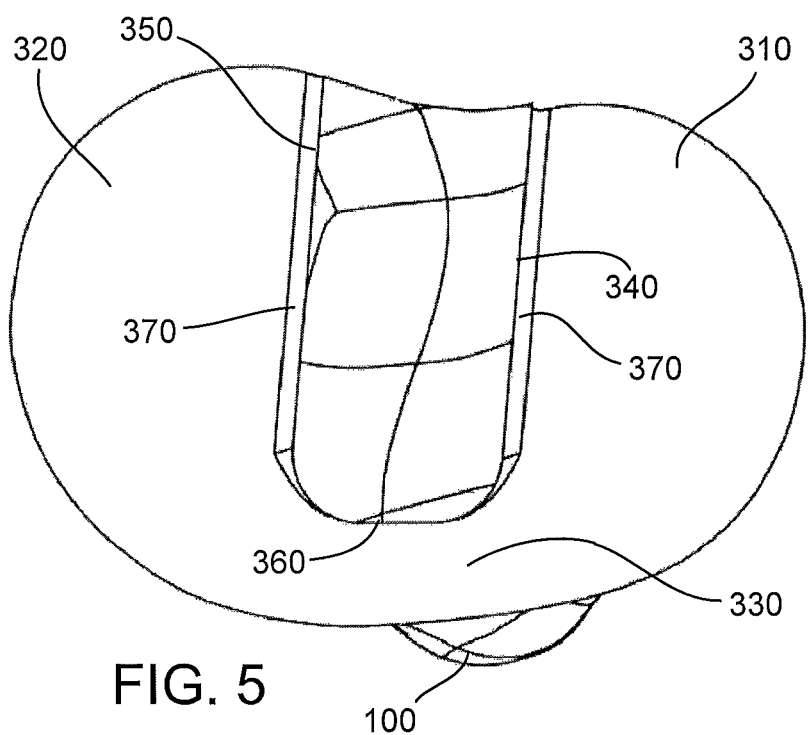
FIG. 5 is a top plan view of a resected proximal tibia according to another implementation, and a cutting profile for a vertical anterior eminence resection.

FIGS. 3 and 4 show the proximal tibia 100 of FIG. 1 after resections using the patient-matched tibial cutting guide 200 of FIG. 2. As shown in FIGS. 3 and 4, the medial 310 and lateral 320 plateau resections, as well as the horizontal anterior eminence resection 330, are substantially co-planar, while the medial 340 and lateral 350 vertical eminence resections and the vertical anterior eminence resections 360 are substantially perpendicular to the plateau resections. The curved sections 370 joining the vertical eminence resections to the horizontal plateau resections shown in the particular implementation of FIG. 3 are caused by two of the fastening pins discussed further below. FIG. 5 shows a top plan view of the resections from an alternative implementation where the vertical anterior eminence resection 360 is provided by a cutter having a curved profile.

Other resection layouts, positions and orientations of resections are also possible and within the scope of the present disclosure. For instance, in some implementations, the plateau resections 310, 320 do not have to be coplanar and the vertical eminence resections 340, 350 could be non-parallel and/or extend at non-perpendicular angles from the plateau resections 310, 320.

In some implementations utilizing the cutting guide of FIG. 2, the two plateau resections 310, 320 are made first, followed by the two anterior eminence resections, with the two vertical eminence resections 340, 350 being performed last, although, in other implementations, other resection orders could be used. In some implementations, this order of resections may preserve pin fixation longer during the procedure.

Figure 6:
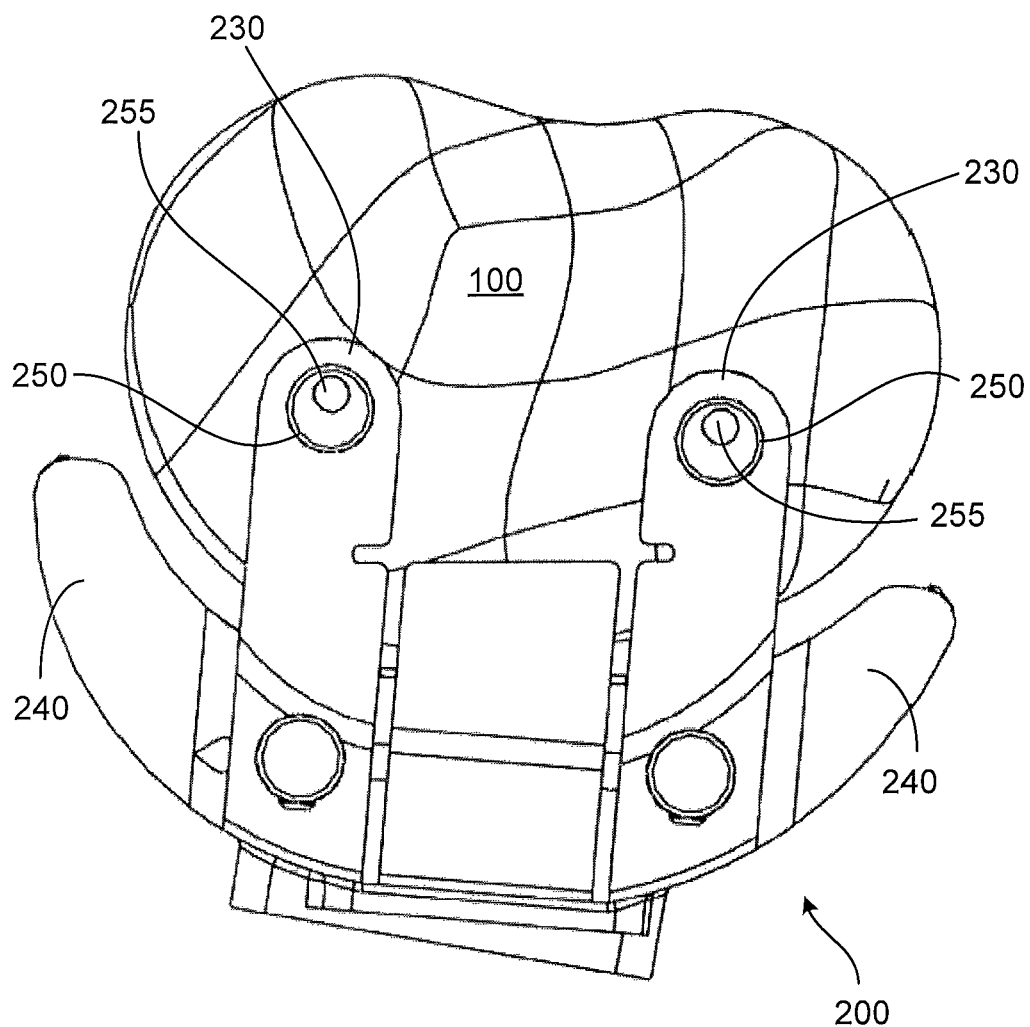
FIG. 6 is a top plan view of the patient-matched cutting guide and proximal tibia of FIG. 2.
Figure 7:
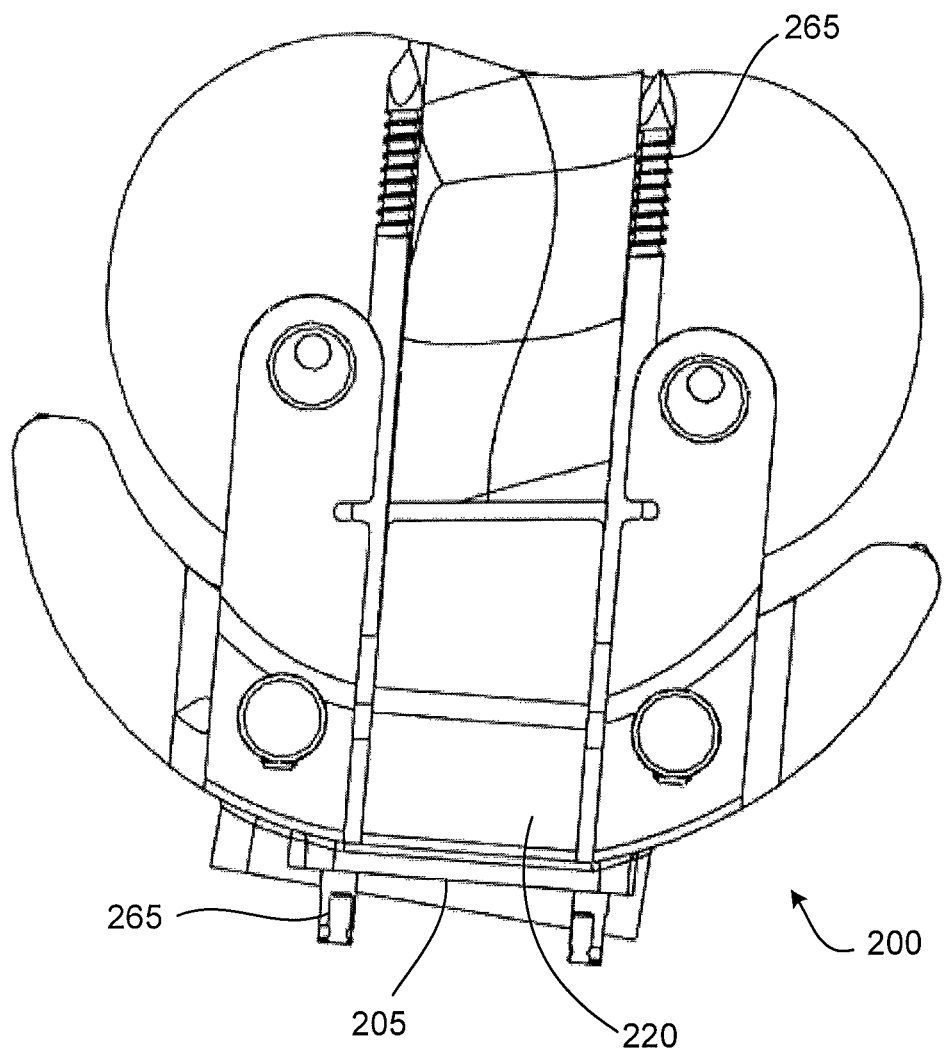
FIG. 7 is a top plan view of the patient-matched cutting guide and proximal tibia of FIG. 2 after resection.

The patient-matched tibial cutting guide 200 of FIG. 2 may include two or more apertures, 260 for receiving fixation pins to secure the guide to the proximal tibia 100. In the particular implementation shown, two secondary, optional apertures 250 are located on distal ends of the outriggers 230 and are oriented vertically to receive pins 255 penetrating surfaces of the medial and lateral articulation surfaces. Two primary apertures 260 are located in the central portion and are oriented horizontally to receive pins 265 penetrating anterior surfaces of the proximal tibia 100. FIG. 6 shows the location of the two vertical pins 255. FIG. 7 shows the location of the two horizontal pins 265. In this particular implementation, the apertures are located proximate the patient-matched surfaces on the bone facing sides of the instrument, although other locations are also possible.

The horizontal pins 265 shown in FIGS. 2 and 7 extend just to the posterior side of the proximal tibia. In the implementation shown by FIG. 7, exterior surfaces on the central portion of the cutting guide (i.e. surfaces that do not face the bone) are calibrated to the specific patient and to the specific length of pin to be used such that the pins just reach the posterior side of the proximal tibia. In this particular implementation, the exterior surface 205 on the central portion 220 contacts shoulders (not shown) on each pin to limit the anterior-posterior insertion depth of each pin 265 to a precise, pre-determined depth, although other structures and pin/cutting guide interaction mechanisms could be utilized in other implementations to limit pin-depth to a desired depth. In some implementations, the portions of the "exterior" surface for contacting the pin could be recessed into the block compared to the surrounding "exterior" surfaces, although, in other implementations, these surfaces could be flush with respect to one another or arranged in other manners. In some implementations, alternative mechanisms can be used to calibrate the pin depth with respect to the exterior surface or other portions of the cutting guide. For instance, in some implementations, laser etched lines or other indicia could be used to indicate the anterior-posterior depth of the pin with respect to the patient-matched exterior surface of the cutting guide.

In some implementations, this depth can be set by examining MRI or other image data specific to the patient's anatomy and, in conjunction with a desired pin length, determine where the exterior surface of the patient-matched cutting guide (or portions of the exterior surface, or other structures or mechanisms) is positioned to properly limit the depth of the pins. Various automated, semi-automated, or manual procedures and systems could be used to process imaging data or otherwise determine the proper insertion depth.

In some, although not necessarily all, implementations, it may be desirable to use the horizontal pins (or other structures associated with the cutting guide) to protect the tibial eminence from notching, undercutting or other unintended resection or damage by the cutting instruments and other instruments used during the surgical procedure. In some, although not necessarily all, of these implementations, it may be desirable to precisely control the anterior-posterior depth of the horizontal pins (or other horizontal, vertical or other oriented pins or other fastening mechanisms) such that the pins extend along the entire (or substantially entire) anterior-posterior length of the tibial eminence to provide such protection without substantially extending posterior to the tibia (which could undesirably impact on surrounding soft tissue or other anatomy). In such instances, the depth control mechanisms discussed above may be desirable.

In some implementations, the patient-matched tibial cutting guide may be packaged, shipped and/or otherwise associated with the proper length of pins to be used for the specific patient. In these or other implementations, the correct pin length could be indicated on the patient-matched guide itself (or on the guide's packaging).

In some implementations, the particular positions and orientations of the pin receiving openings in the patient-matched instrument are such that once all of the resections have been completed, the cavities formed by the pins inserted through those openings do not remain in the patient's bone. In other words, in some implementations, the pins used with the patient-matched instrument only extend through bone that are removed by the resections. In some implementations, pin length may also be adjusted or optimized to reduce or eliminate the incidence of pin holes in the remaining bone. For instance, in some implementations, the vertical pins may be positioned such that they do not extend below the level where the horizontal plateau resections are made.

Figure 8:
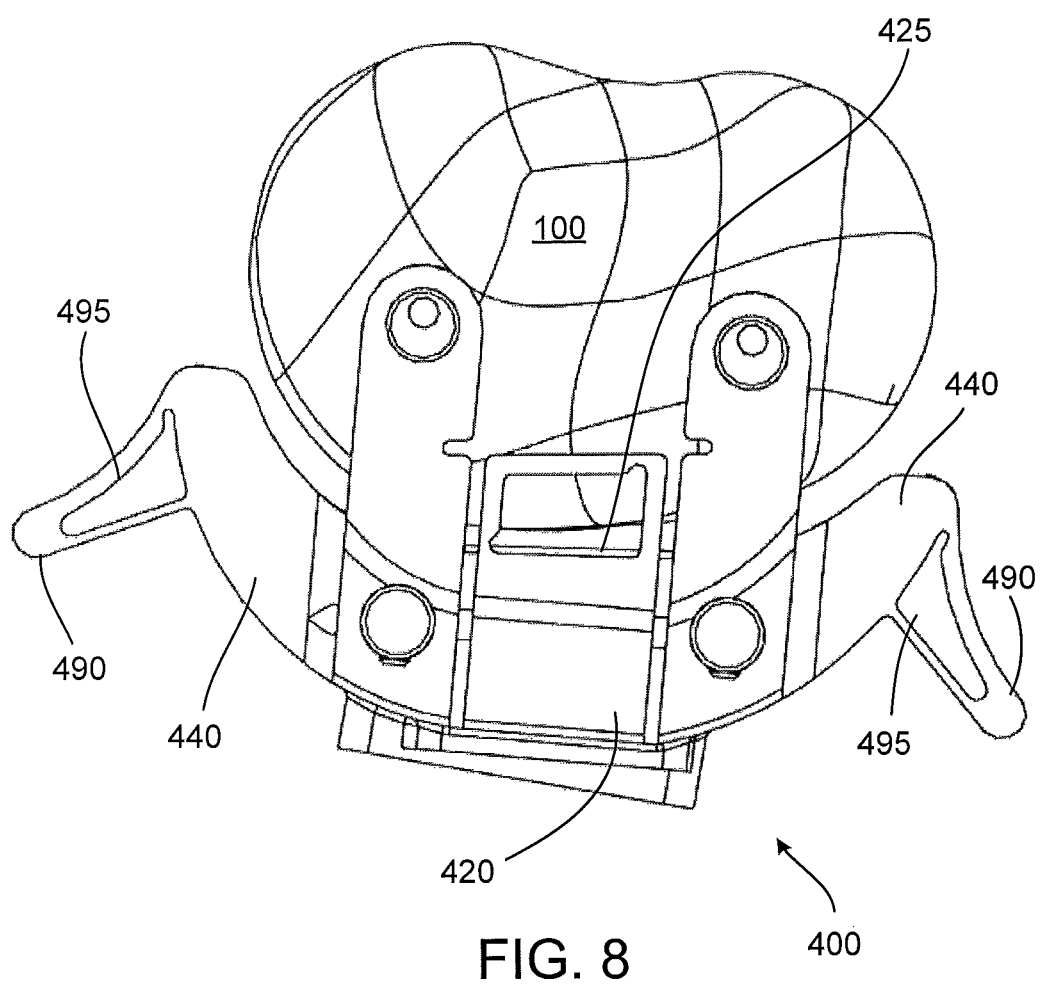
FIG. 8 shows another implementation of a patient-matched cutting guide.

FIG. 8 shows an alternative implementation of a patient-matched tibial cutting guide 400 having additional features. The cutting guide of FIG. 8 includes a visualization window 425 positioned in the central portion 420 of the guide 400 for visualizing anterior portions of the tibial eminence. In the particular implementation shown, the visualization window 425 can be revealed by breaking off a frangible portion of the guide (not shown).

The cutting guide 400 of FIG. 8 also includes retractor features 490 positioned on distal ends of the two wings 440. In some implementations the retractor features 490 may facilitate retaining soft tissues away from the operation site, to allow better visualization and to protect those soft tissues from damage. In the particular implementation of FIG. 8, the retractor features 490 include hollow portions 495, which may help to dampen at least somewhat the forces exerted on the cutting guide 400 by the soft tissues retained by the retractor features 490. In some implementations, this may help avoid potentially undesirable deflection, deformation or other alteration of the shape, position and/or orientation of the cutting guide or particular portions of it, such as the wings 440 and guide surfaces on those wings. In other implementations, other shapes and configurations of retractor features 490 are possible, or, in other implementations, retractor features are unnecessary.

Figure 9:
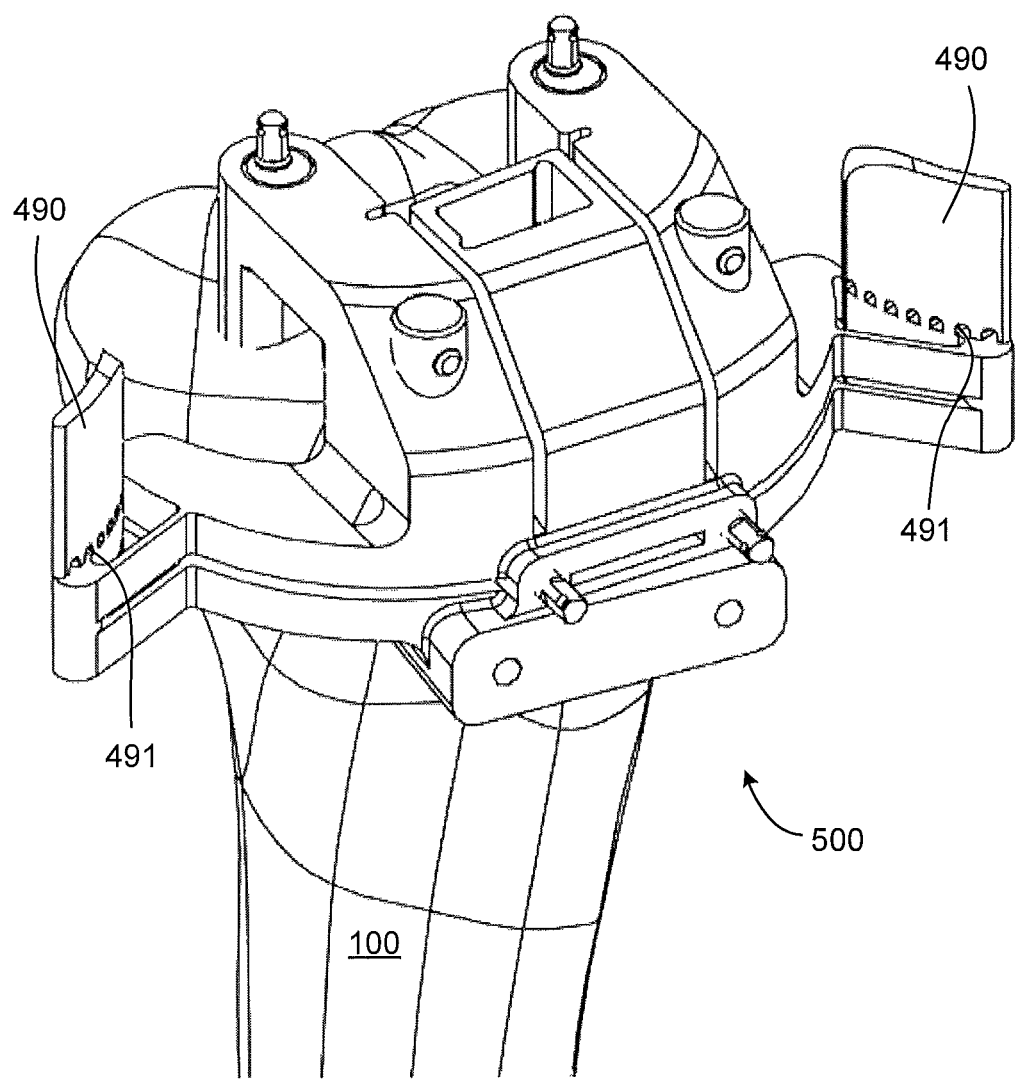
FIG. 9 is another view of the patient-matched cutting guide of FIG. 8.

In some implementations, certain features of the patient-matched guide, such as the retractor features 490 and visualization window 425 feature of the patient-matched tibial cutting guide 400 of FIG. 8, may be removable or otherwise reconfigurable. For instance, as shown in FIG. 9, the retractor features 490 may include a series of perforations 491 that may facilitate the removal of the retractor features 490 after use or if they are not desired for the particular procedure. In other implementations, other frangible or non-frangible connections, structures or other mechanisms can be used to allow portions of the patient-matched instrument to be broken away, removed or otherwise repositioned.

In some implementations in which portions of the patient-matched instrument are intended to be broken off during the procedure, it may be desirable to utilize frangible connections that do not result in excessive (or any) debris when broken to avoid contamination of the wound site. In some implementations, the particular geometry of the frangible connection may lower the chances of small pieces contaminating the wound when the frangible portion is removed. In these or other implementations, the patient-matched instrument itself can be formed from one or more materials that reduce the likelihood of debris resulting from severing a frangible connection.

In some implementations, the frangible features can be formed in a patient-matched instrument formed in a selective laser sintering process using Nylon-12 as the manufacturing material. In these or other implementations, the power of the laser could be varied during the manufacturing process to create lines or regions of material in which the bonding strength is reduced, allowing certain portions of the patient-matched instrument to be broken off more easily.

In some implementations, the removable features can be removed after use to avoid interference with later portions of the procedure. In some implementations, removal of the removable features may allow greater access or visualization of portions of the patient-matched instrument, anatomy, or other items that were not easily accessible or were not able to be easily visualized prior to removal of the removable feature. For instance, in some implementations, removal of a removable feature from the patient-matched instrument may allow access to other features of the patient-matched guide for guiding or otherwise performing other operations or portions of operations on the anatomy using other features of the patient-matched guide that were originally hidden by the removable feature. In these or still other implementations, removal of a removable portion or portions may facilitate adjusting the guides or other features of the patient-matched instrument.

Figure 10:
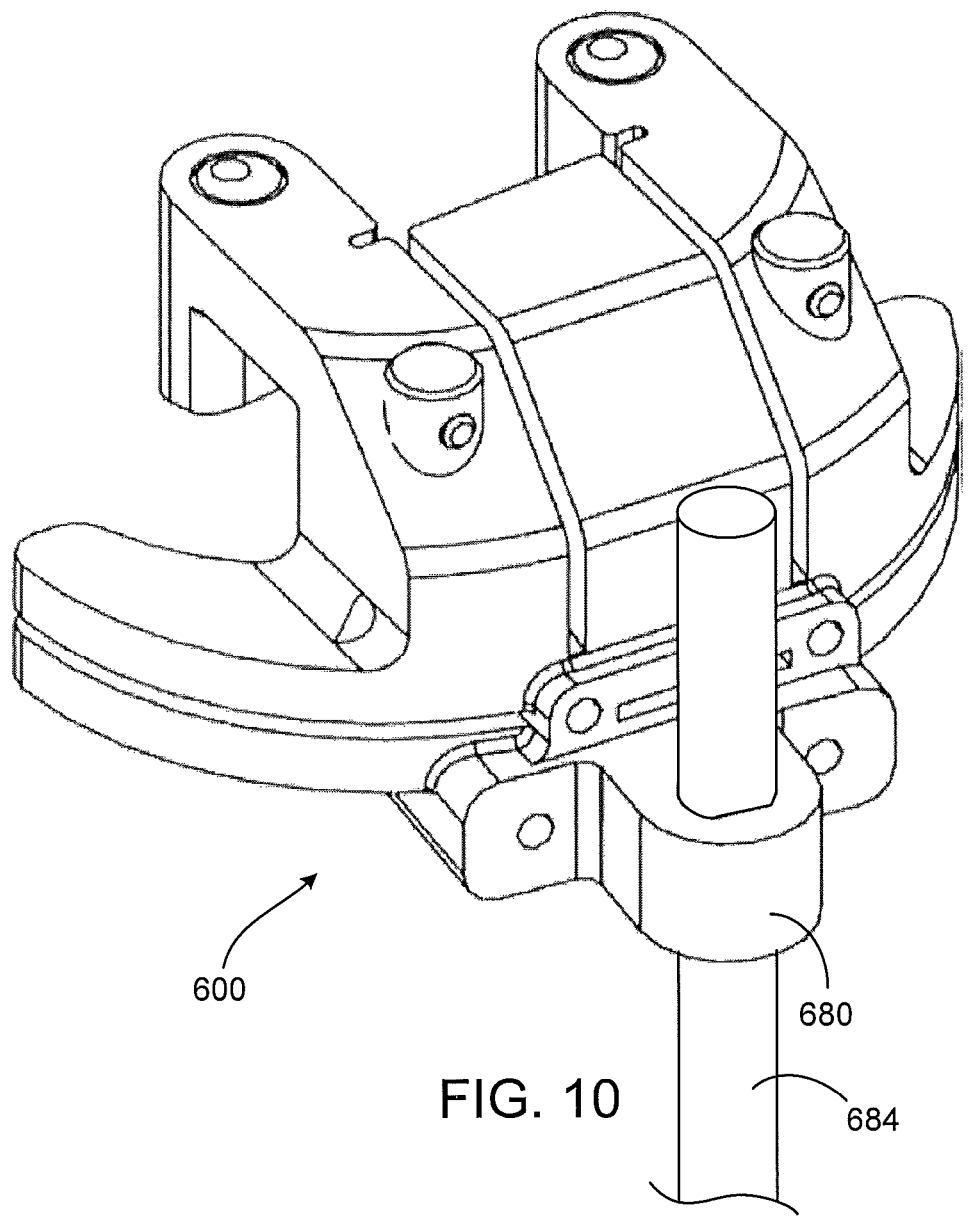
FIG. 10 shows another implementation of a patient-matched cutting guide.

FIG. 10 shows a patient-matched tibial cutting guide 600 that includes a built in drop rod connector 680. In some implementations, this can be an integral part of the patient-matched instrument, whereas, in other implementations, this can be a feature that can be added and/or removed from the patient-matched instrument at the user's discretion and at the time of his or her choosing. In some implementations, the drop rod connector 680 can be secured to the patient-matched guide 600 using a frangible connection similar to those described above for the removable retractor features. The drop rod connector 680 shown in FIG. 10 facilitates the connection and alignment of a drop rod 684 with the patient-matched tibial guide 600, which, in some implementations, may facilitate visualizing the alignment of the patient-matched instrument 600 with an anatomic or mechanical axis of the tibia or other structure of the tibia or other anatomy. This visualization may allow for cross-checking of orientation of the patient-matched guide intraoperatively.

Figure 11:
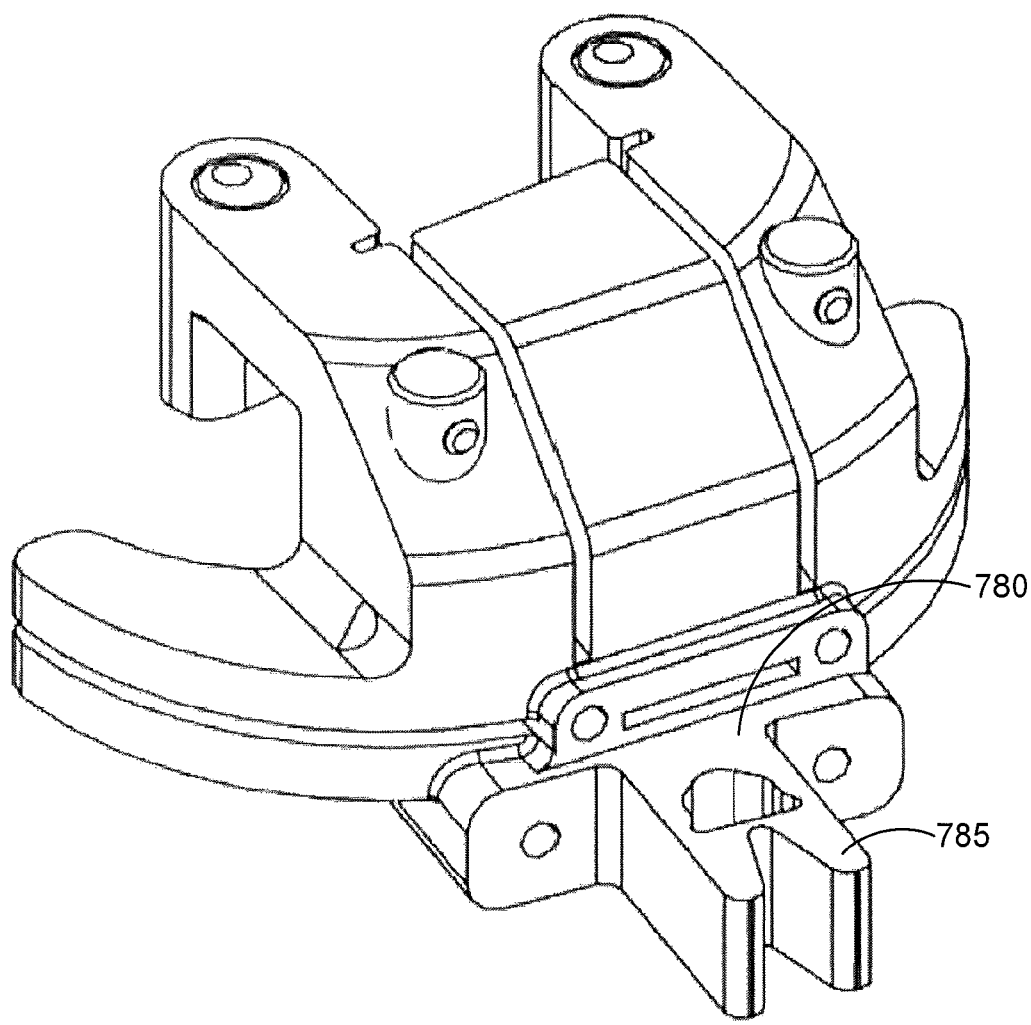
FIG. 11 shows another implementation of a patient-matched cutting guide.

FIG. 11 shows another implementation 700 of a patient-matched tibial cutting guide that includes a drop-rod connector 780 that has a user-operated mechanism with two protrusions 785 that, when pinched together, holds a drop rod (not shown) in the aperture of the connector 780, ensuring that it is in a desired position and orientation with respect to the cutting guide. In the particular implementation of FIG. 11, the user operated mechanism 785 and at least portions of the aperture of the drop-rod connector 780 are formed from a material that is compliant such that when the protrusions are pinched together the aperture deforms at least slightly to tighten its fit around a drop rod extending through it. In some implementations, the entire patient-matched instrument may be made from a compliant material that is sufficiently sized, shaped, and has other characteristics such that some portions of it can be deformed whereas other portions are more resistant to deformation (e.g., in some implementations, it may be desirable for portions defining and/or supporting the cutting guide surfaces or point contact features (some of which are described above and below) to be resistant to deformation to ensure accurate alignment of the tibial resections). In some implementations, other portions of the patient-matched instrument or features associated with the patient-matched instrument may be made of material or in a sufficient shape or other configuration to take advantage of a compliant portion of the construct.

Figure 12:
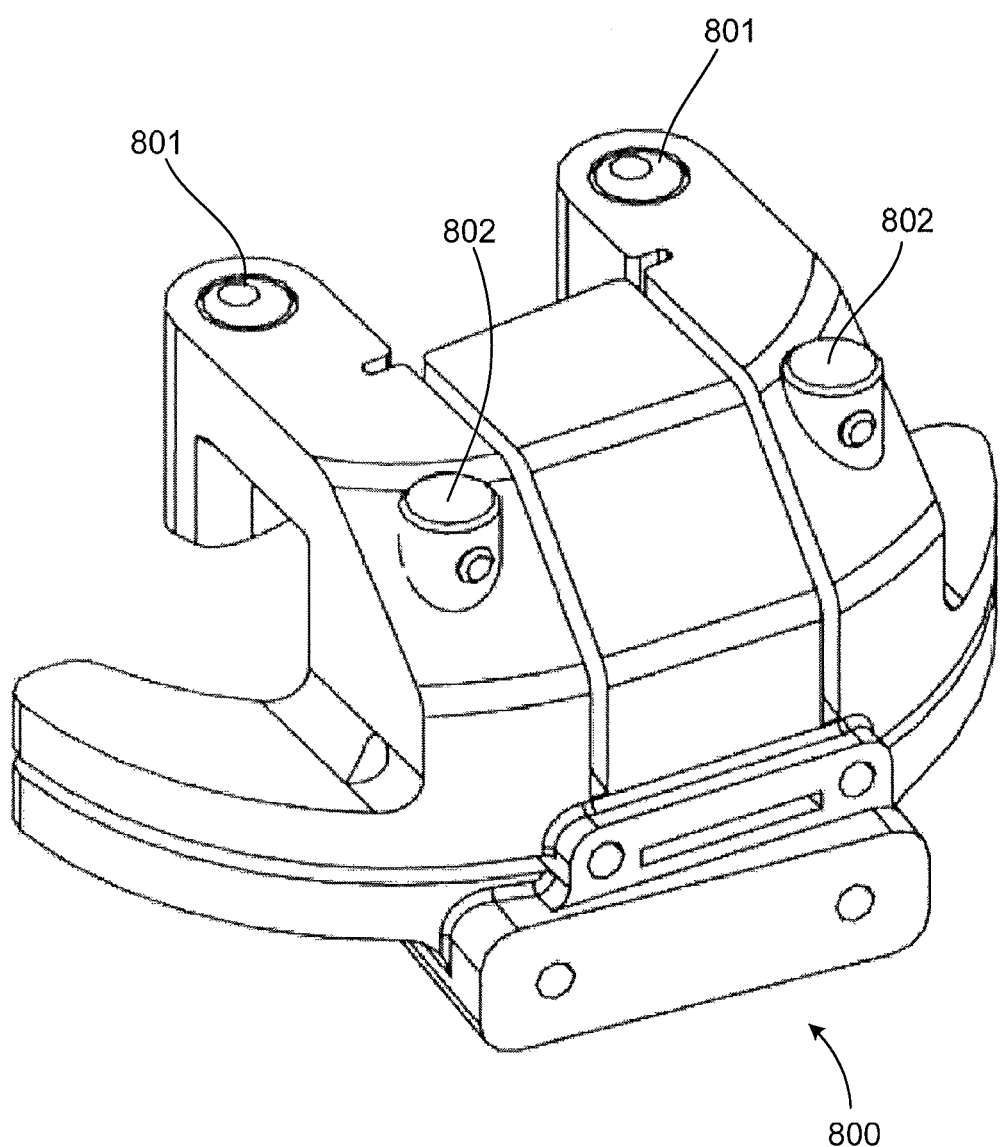
FIG. 12 shows another implementation of a patient-matched cutting guide.

In some implementations, such as the implementation shown in FIG. 12, the patient-matched instrument 800 may include reinforcements to increase the rigidity of the instrument or certain portions of the instrument. For instance, in the implementation of FIG. 12, many portions of the patient-matched tibial cutting 800 guide may be formed from Nylon-12 using a selective laser sintering process (SLS), and, at least conceptually, could be subject to undesired deformation, especially when a cutting blade or other cutting device is being used in conjunction with the instrument. In at least some of these instances, it may be desirable to include reinforcements 801 in the patient-matched instrument to help increase the rigidity of the device. In the particular implementation of FIG. 12, these reinforcements 801 are mostly embedded in the instrument, and are not visible from the outside (except for the two posts 802 extending superiorly from anterior portions of the outriggers).

In some implementations, the reinforcements may be formed from materials having different properties than the rest of the patient-matched instrument. Thus, in some implementations, the majority of the patient-matched instrument may be made from Nylon-12 using an SLS process whereas the reinforcements may be formed from surgical grade stainless steel or other suitable materials. In some implementations, the reinforcements may be formed from traditional manufacturing methods, and used as a scaffold around which the rest of the patient-matched instrument is formed using SLS or other manufacturing techniques used to form a patient-matched instrument. In other implementations, both the reinforcements and the rest of the patient-matched instrument may be formed using SLS or other rapid production technologies, with, in some implementations, the reinforcements formed first using a first material and the rest of the patient-matched instrument formed second using a second material. In other implementations, the reinforcement portions and the rest of the patient-matched instrument may be formed simultaneously.

Figure 13:
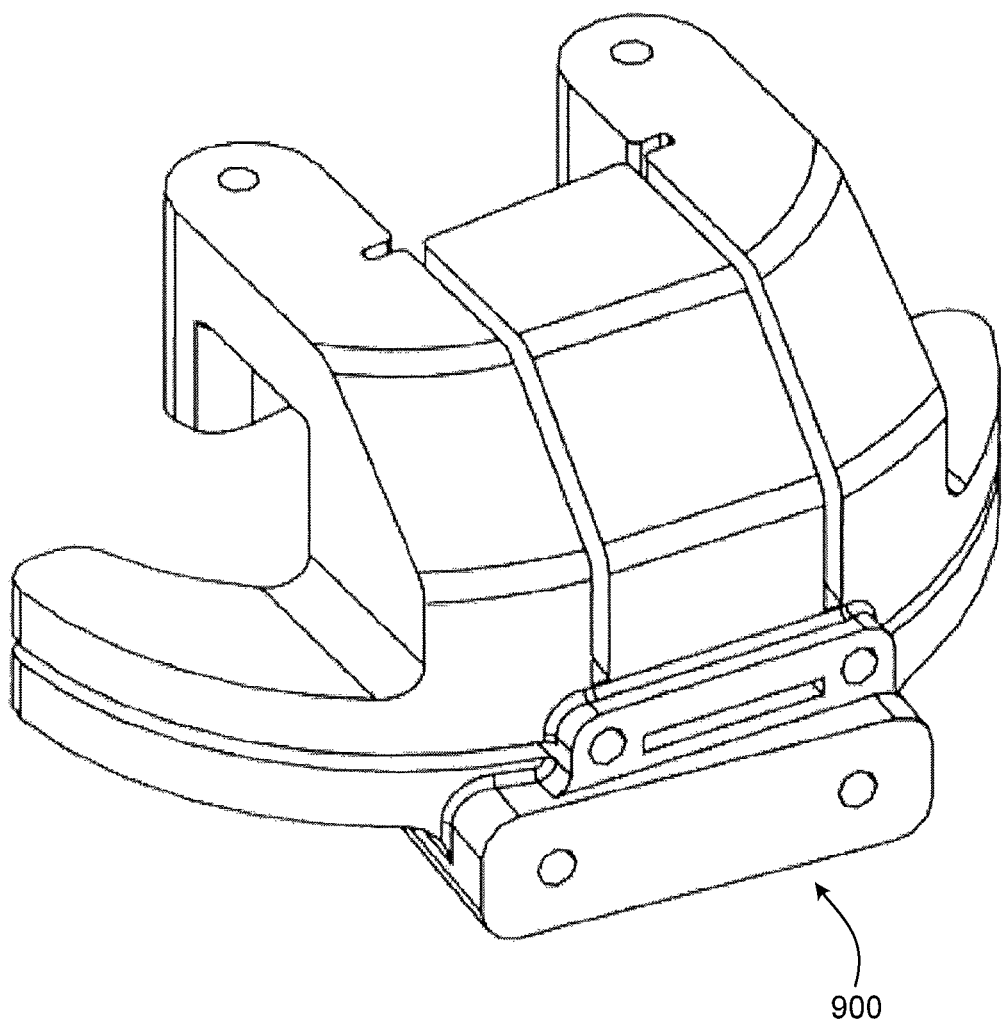
FIG. 13 shows another implementation of a patient-matched cutting guide.

In other implementations, such as the implementation shown in FIG. 13, it is not necessary to include reinforcement materials and the patient-matched instrument 900 may be formed from a single material, yet still be sufficiently rigid.

Figure 14:
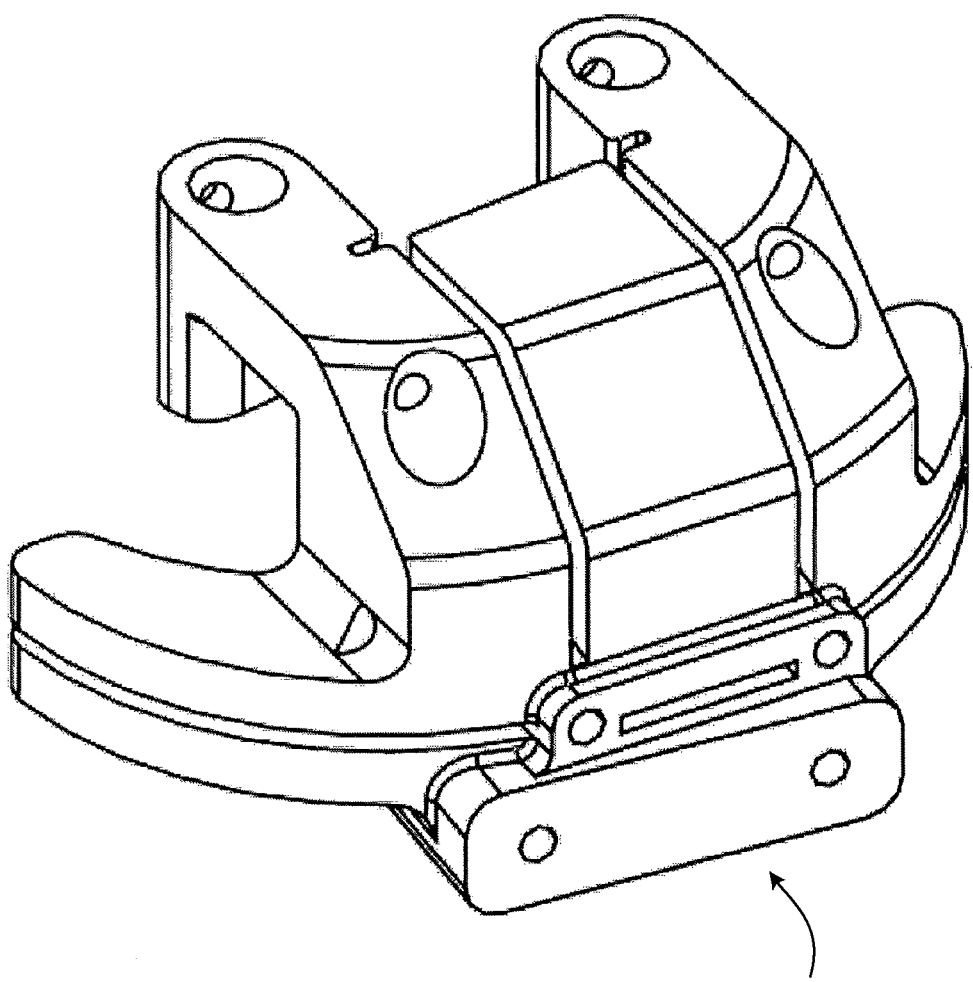
FIG. 14 shows the patient-matched cutting guide of FIG. 12 with certain components removed.

FIG. 14 shows a patient-matched tibial cutting block 1000 configured to receive reinforcement members, but without those reinforcement members in place. In some implementations, the patient-matched instrument could be formed through SLS or other rapid production techniques first, and the reinforcement members could be introduced later (either manually or using automation) into the patient-matched instrument, such as by sliding cylindrical reinforcements into cylindrical holes formed in the patient-matched instrument.

Figure 15:
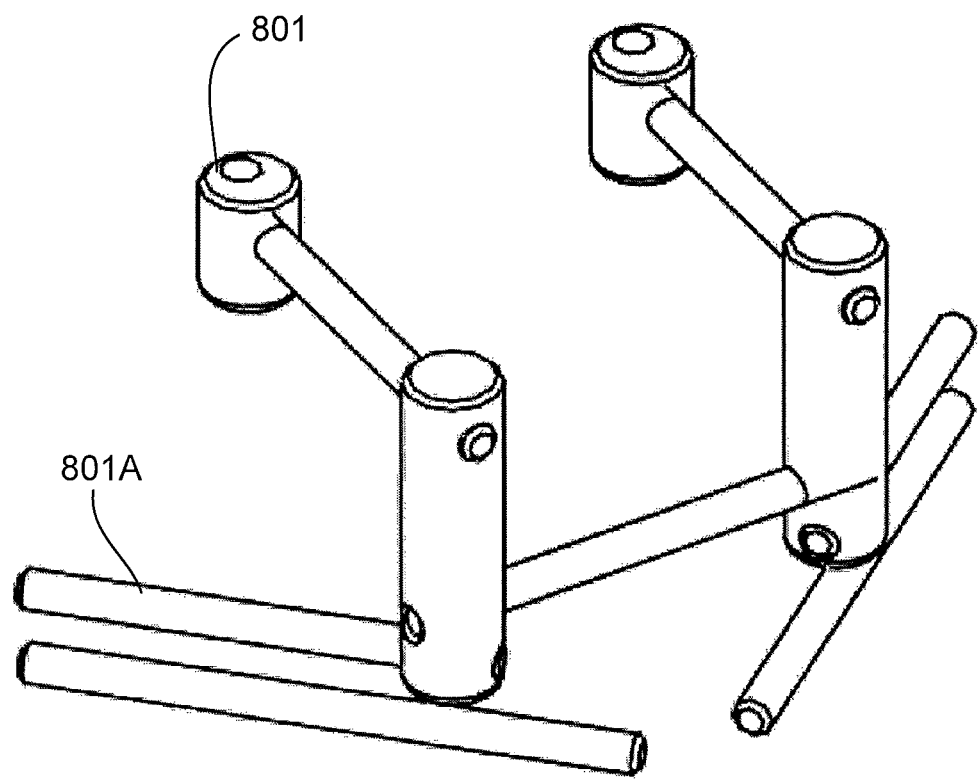
FIG. 15 shows reinforcement structures of the patient-matched cutting guide of FIG. 12.
Figure 17:
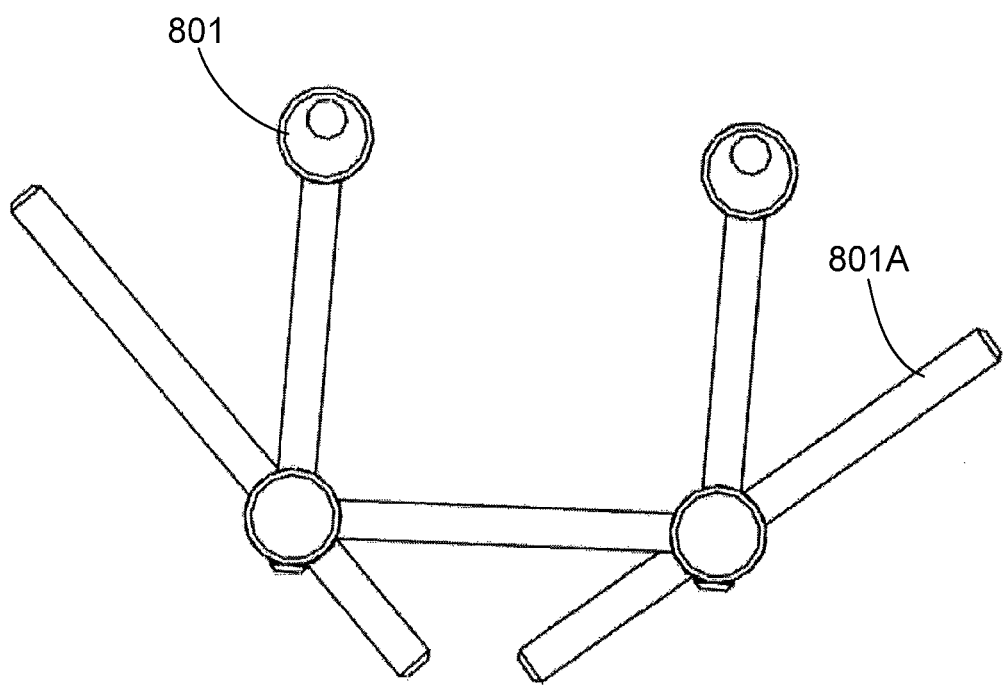
FIG. 17 shows another view of the reinforcement structures of FIG. 15.
Figure 19:
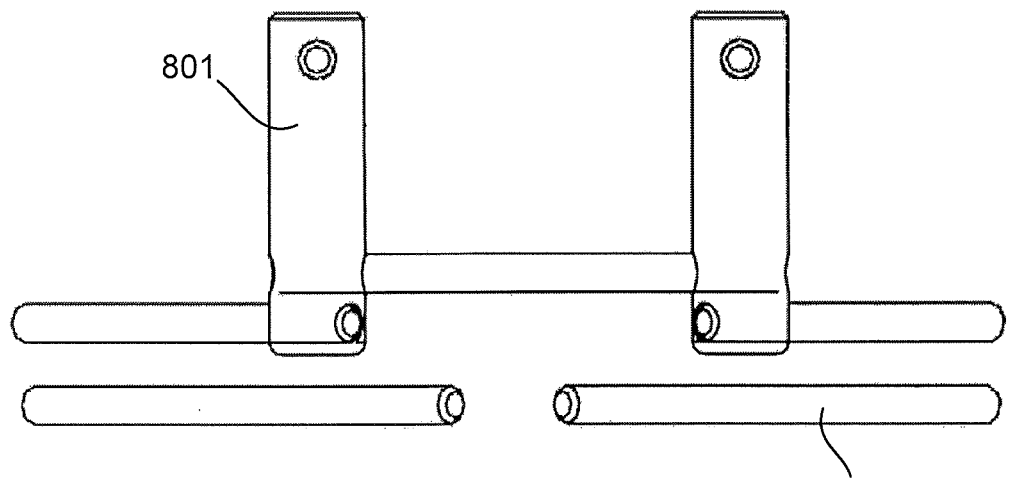
FIG. 19 shows another view of the reinforcement structures of FIG. 15.

FIGS. 15, 17 and 19 show the reinforcement members 801 and 801A from the implementation of FIG. 12. In some implementations, the reinforcement members 801 and 801A may be custom positioned depending on the patient's anatomy and other aspects of the particular patient's planned surgical procedure, whereas in other implementations, the reinforcement members 801 and 801A may have a "standardized" portion around which all of the patient-matched instruments of a particular type or size are built. In some implementations, the reinforcement members 801 and 801A may be an optional part of the patient-matched instrument, and could be included when certain other features of the patient-matched block are customized. For instance, in some implementations, the reinforcement members 801A that are positioned to extend along the wings of the patient-matched instrument may only be necessary when the guide slots are not captured at distal ends.

In the particular implementation shown in FIGS. 15, 17 and 19, the reinforcement members 801 are formed from stainless steel dowel pins, although, in other implementations, other materials could be used.

Figure 16:
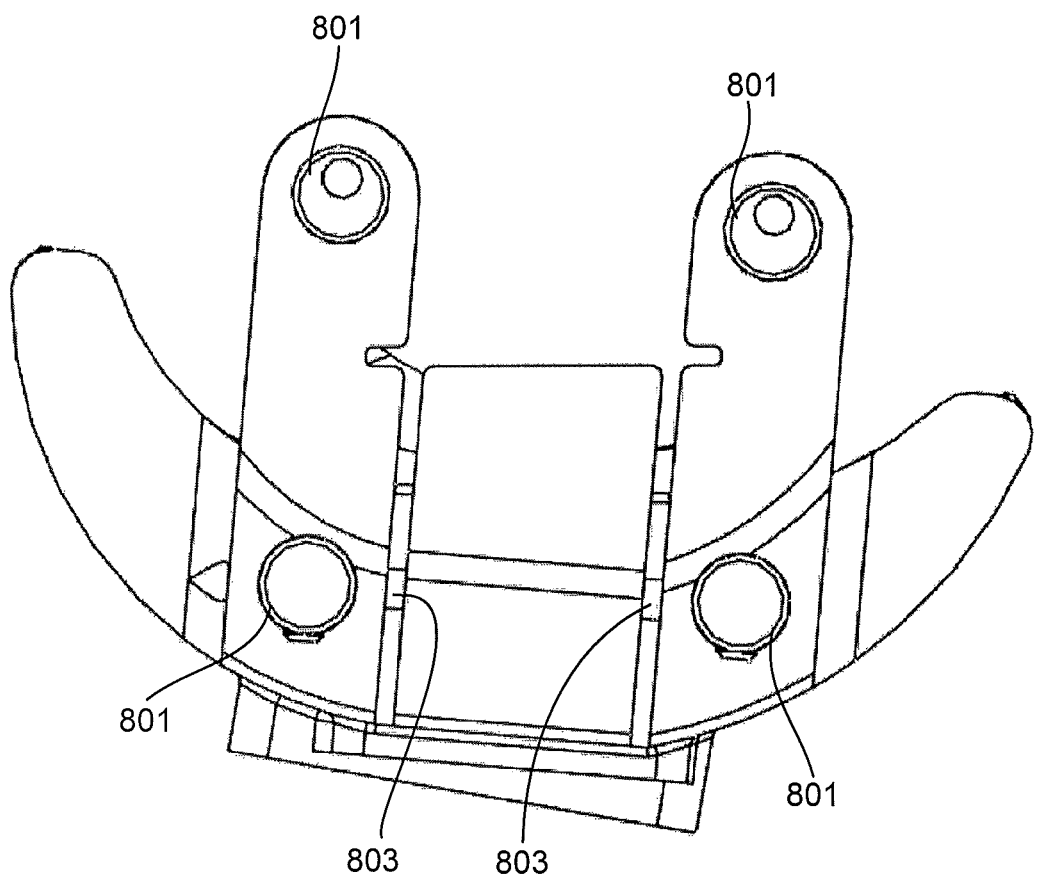
FIG. 16 shows another view of the patient-matched cutting guide of FIG. 12.
Figure 18:
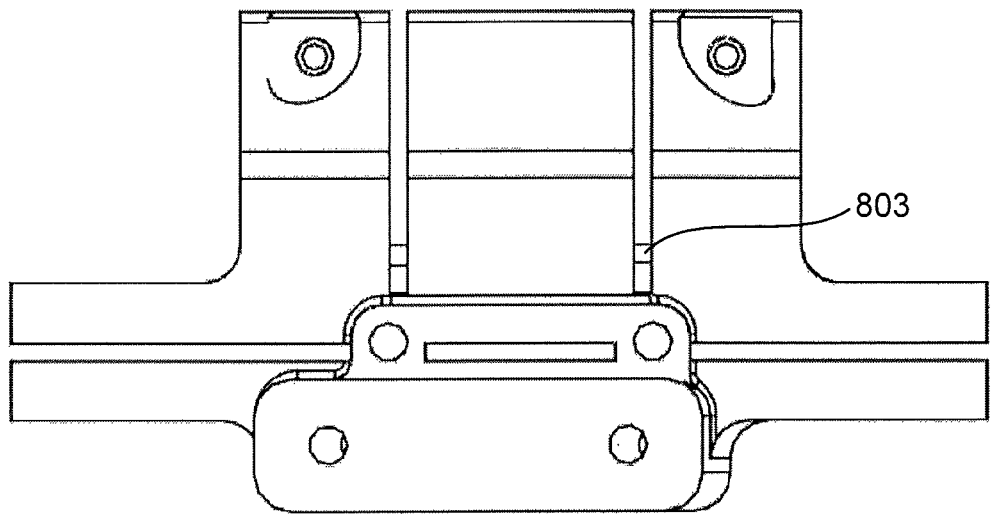
FIG. 18 shows another view of the patient-matched cutting guide of FIG. 12.

As shown by FIGS. 16 and 18, the reinforcement members 801 or materials used in some implementations of the patient-matched instruments described herein could be used for additional or alternative functions to solely providing reinforcement to the instrument. For instance, in the implementation of FIG. 16, one of the central reinforcement members 803 also functions as a horizontal stop to prevent a reciprocating saw from penetrating too deeply when making the vertical medial and lateral eminence cuts, and also to prevent a saw from advancing into the body of the patient-matched instrument. In some implementations, the central reinforcement member 803 works in conjunction with the two horizontal fixation pins to limit certain aspects of the resections. In other implementations, reinforcement members 801 can be strategically positioned in additional or alternative locations to provide stops for other cuts.

Figure 20:
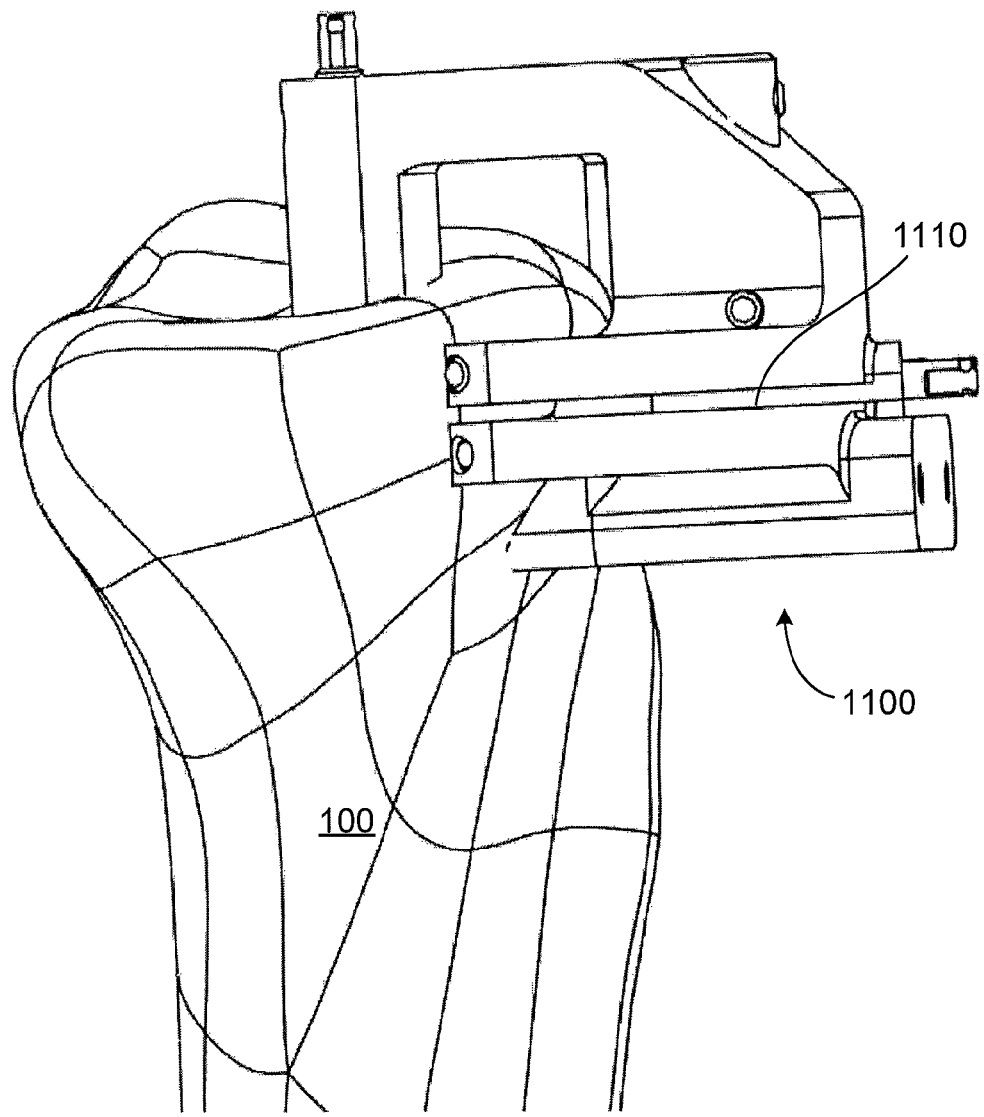
FIG. 20 shows another implementation of a patient-matched cutting guide.
Figure 21:
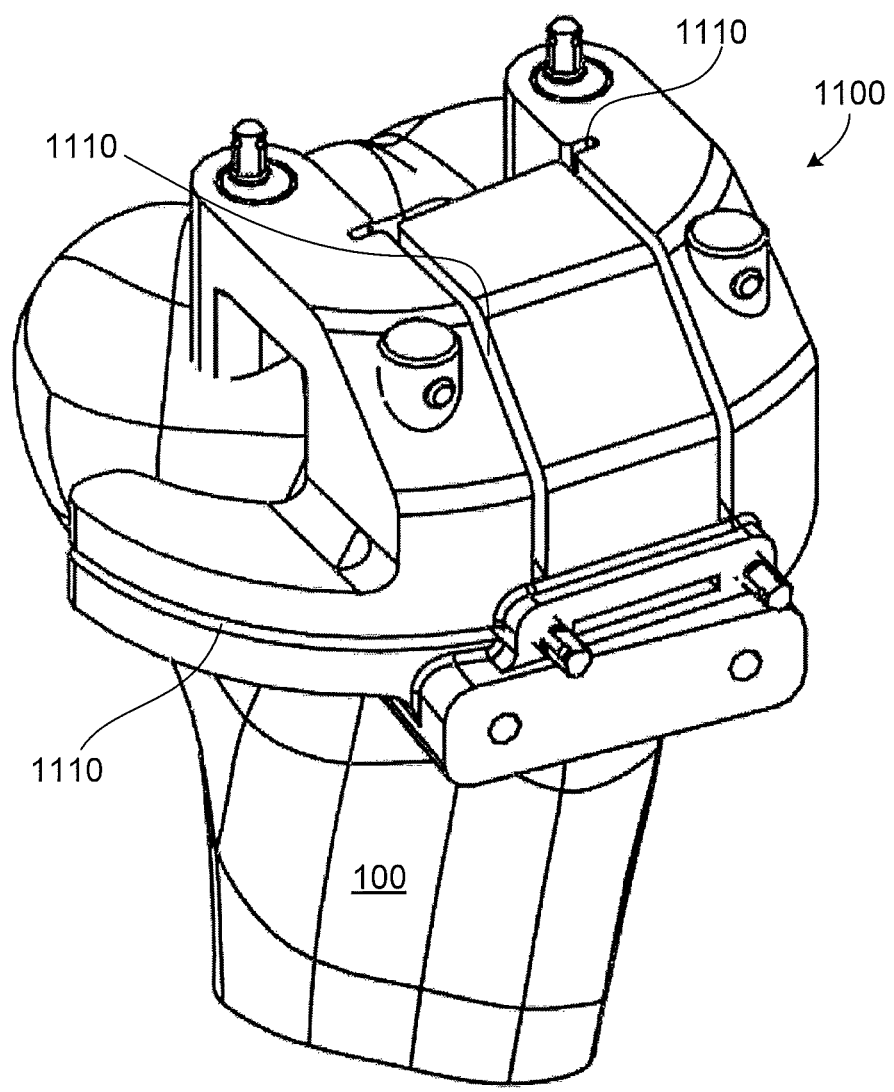
FIG. 21 shows another view of the patient-matched cutting guide of FIG. 20.
Figure 22:
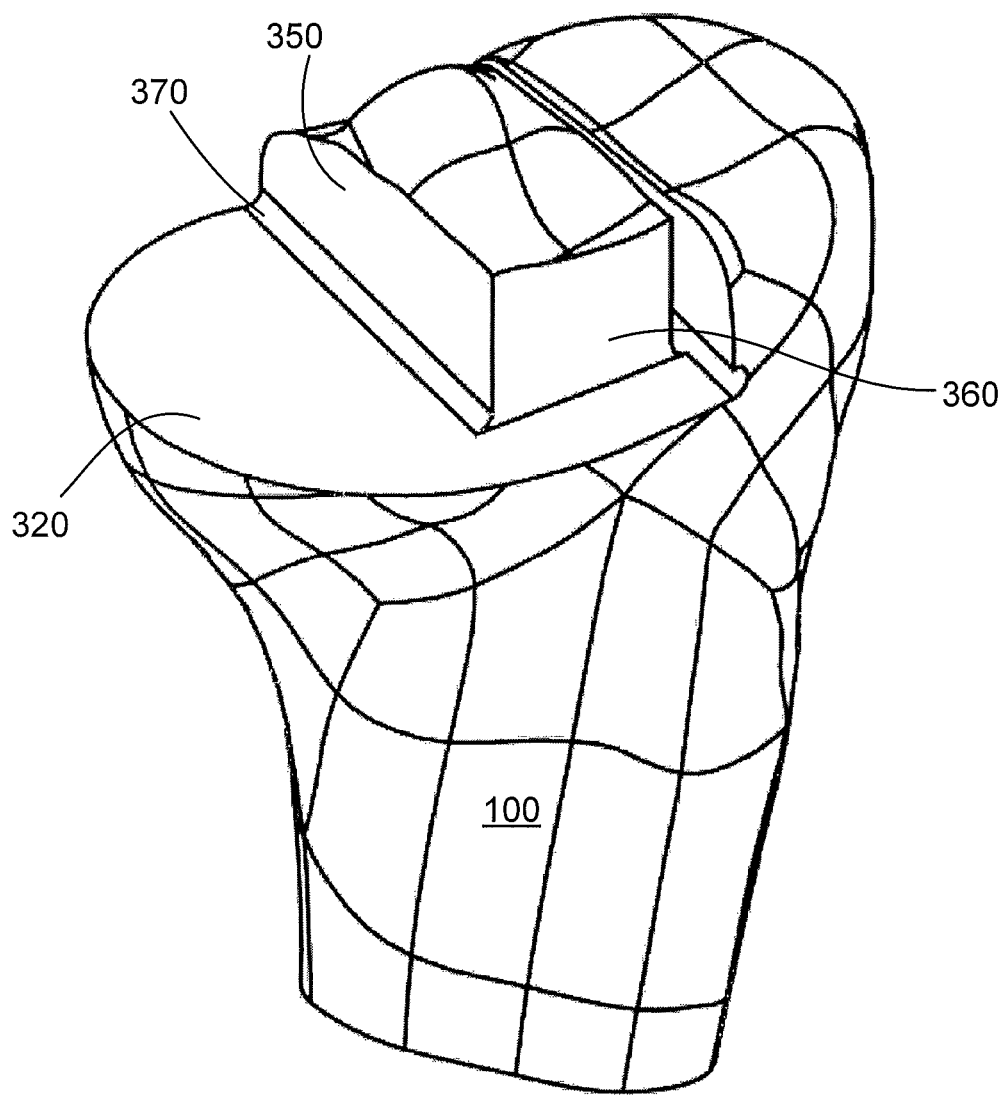
FIG. 22 shows a proximal tibia after resection.

FIGS. 20 and 21 show another implementation of a patient-matched tibial cutting guide 1100 that, like the guide 200 of FIG. 2, includes guide surfaces 1110 for medial plateau, medial and lateral eminence, and vertical and horizontal anterior eminence resections, but, unlike the guide of FIG. 2, does not include a lateral wing or guide surfaces of a lateral plateau resection. FIG. 22 shows the resections that can be made using the cutting guide of FIGS. 20 and 21, although, in some implementations, the cutting guide 1100 might be used to make only some of these resections. In some implementations, the patient-matched tibial cutting guide 1100 of FIGS. 20 and 21 could be used in combination with other patient-matched or standard instrumentation to complete the rest of the tibial resections, depending on the type of knee arthroplasty procedure. For instance, in some implementations, a standard lateral cutting guide could be used to guide the lateral plateau resection, and may include structure for referencing the existing medial plateau resection, other resections, and/or pin holes to align the lateral plateau resection to the other resections.

Figure 23:
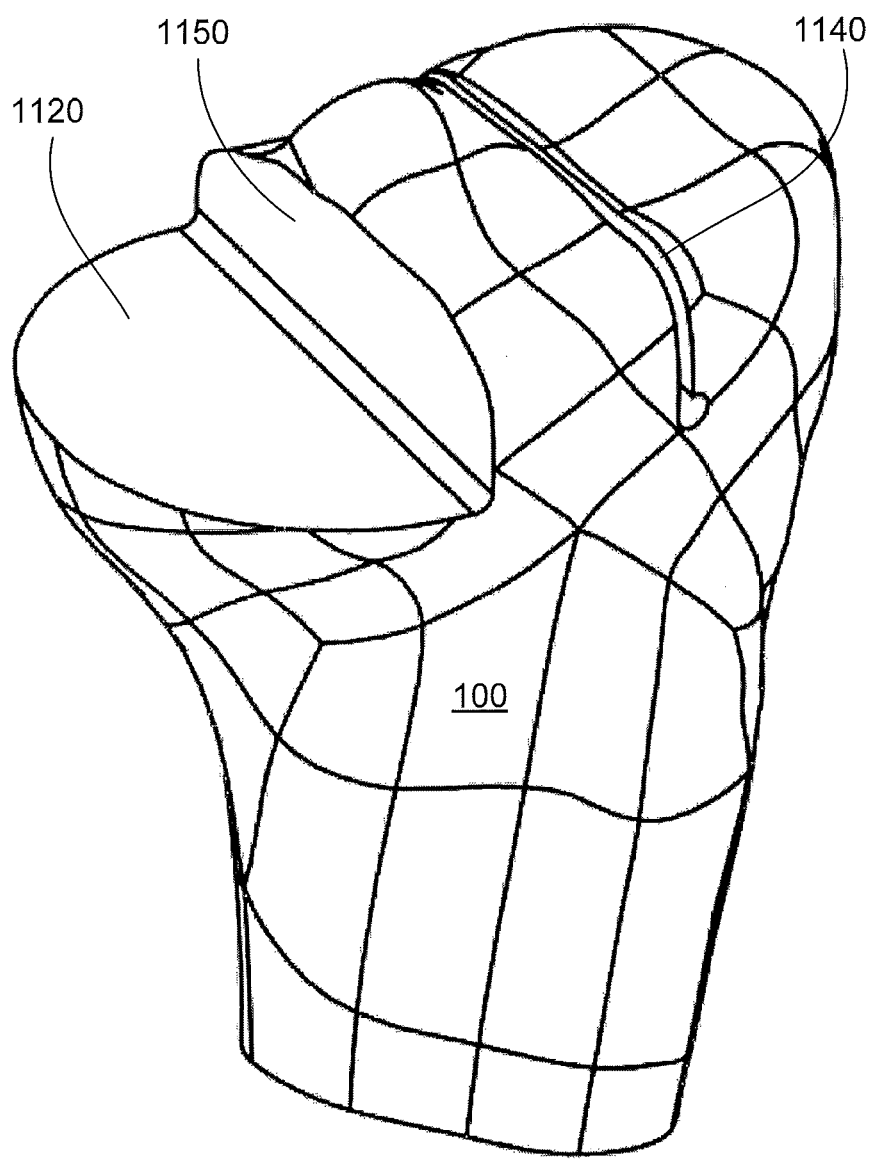
FIG. 23 shows a proximal tibia after resection.
Figure 24:
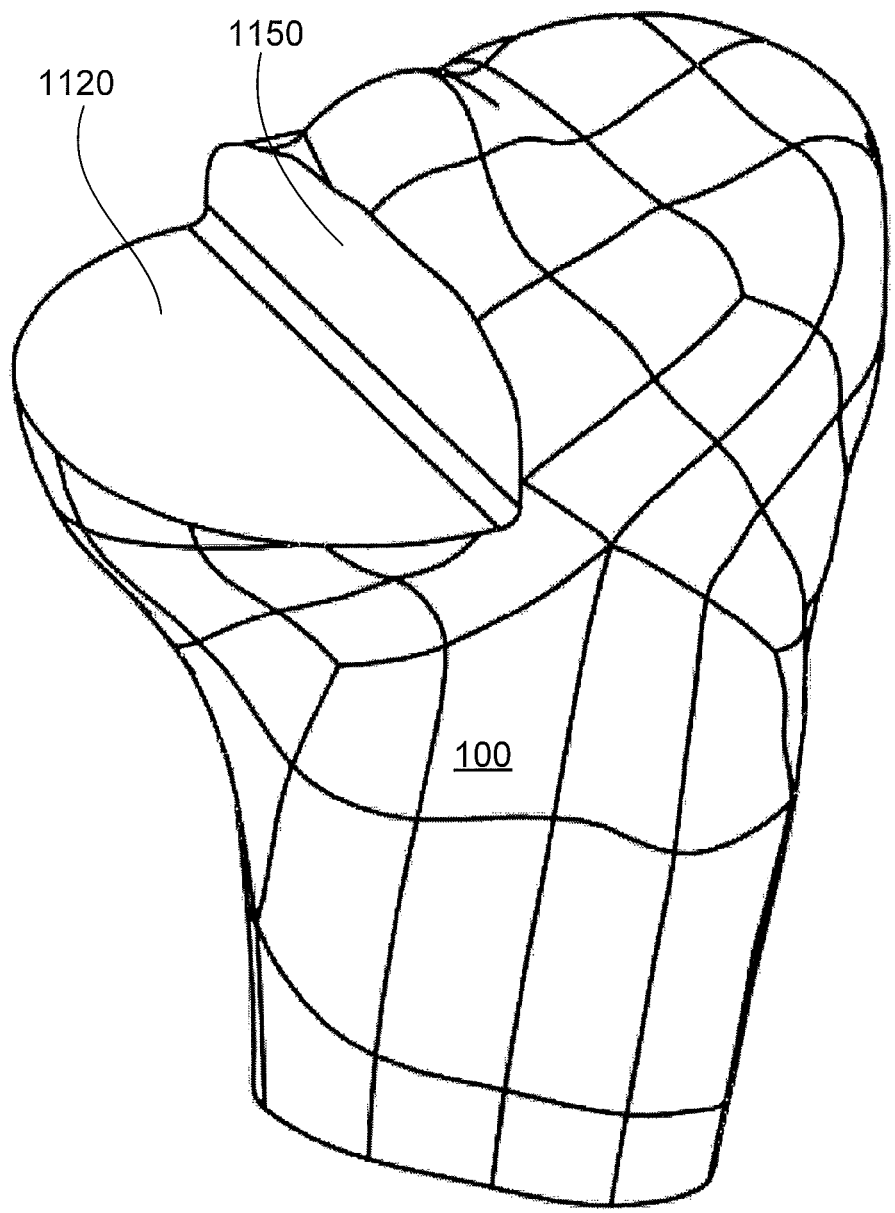
FIG. 24 shows a proximal tibia after resection.

FIG. 23 shows a proximal tibia with medial plateau 1120 and medial 1150 and lateral 1140 eminence resections, but with anterior portions of the eminence still intact. Leaving anterior portions of the eminence intact, at least in earlier stages of the procedure, may reduce in some instances the risk that the eminence could fracture or otherwise be compromised during the procedure, which may be a risk in some procedures, such as procedures in which trials and/or balancing techniques are used to evaluate the medial and/or lateral resections. FIG. 24 shows a proximal tibia 100 with only medial plateau 1120 and eminence 1150 resections, illustrating the possibility of using the patient-matched cutting guide of FIGS. 20 and 21 for a uni-condylar knee arthroplasty.

Figure 25:
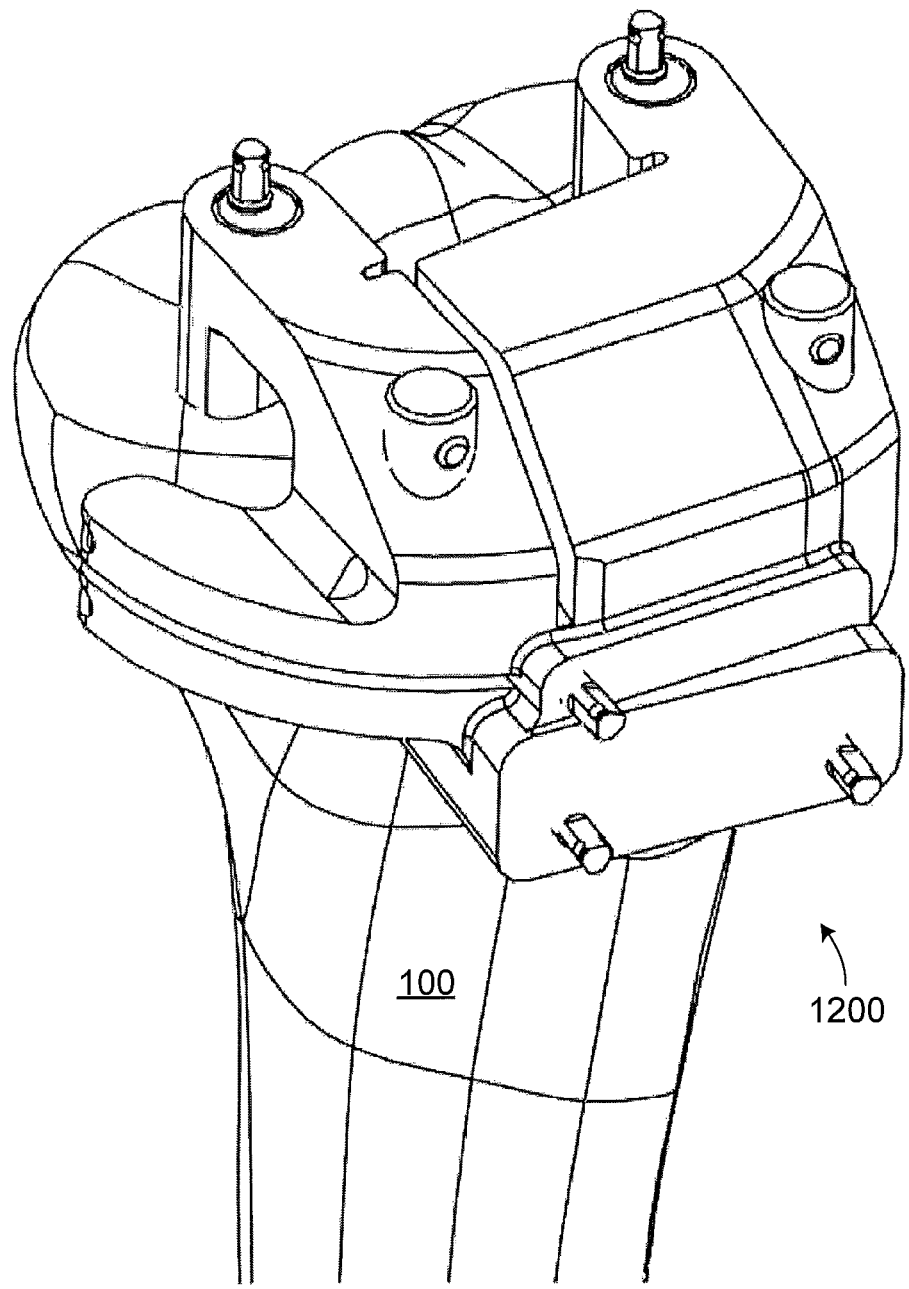
FIG. 25 shows another implementation of a patient-matched cutting guide.
Figure 26:
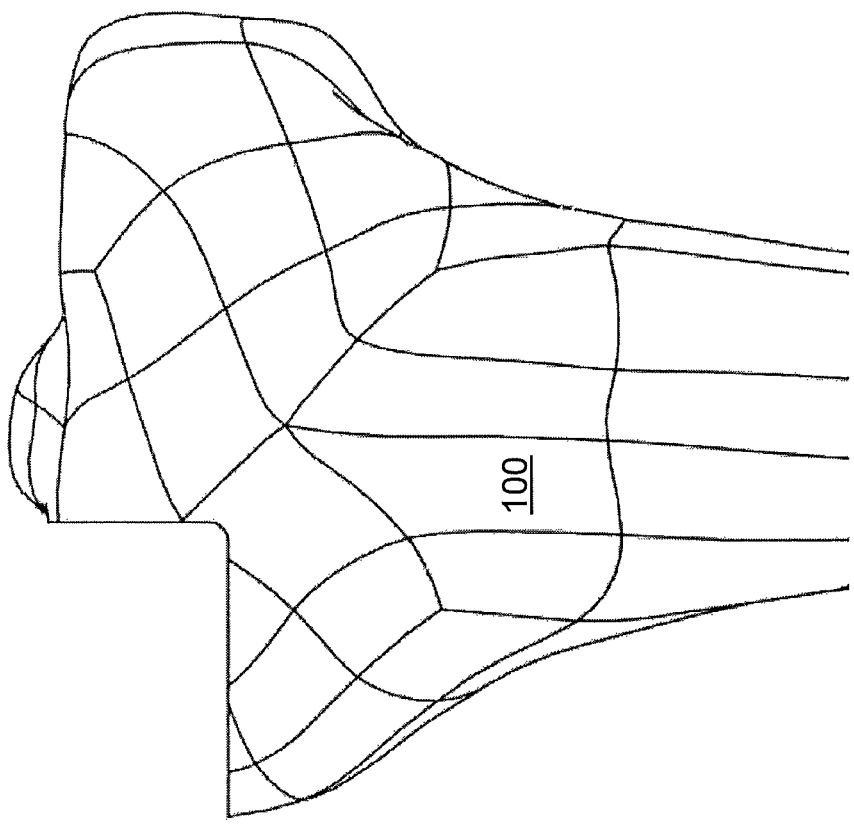
FIG. 26 shows two views of a proximal tibia after primary resections.
Figure 26:
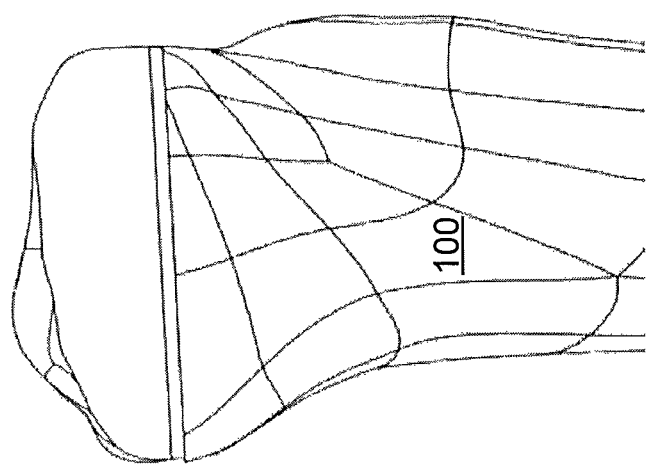
Figure 27:
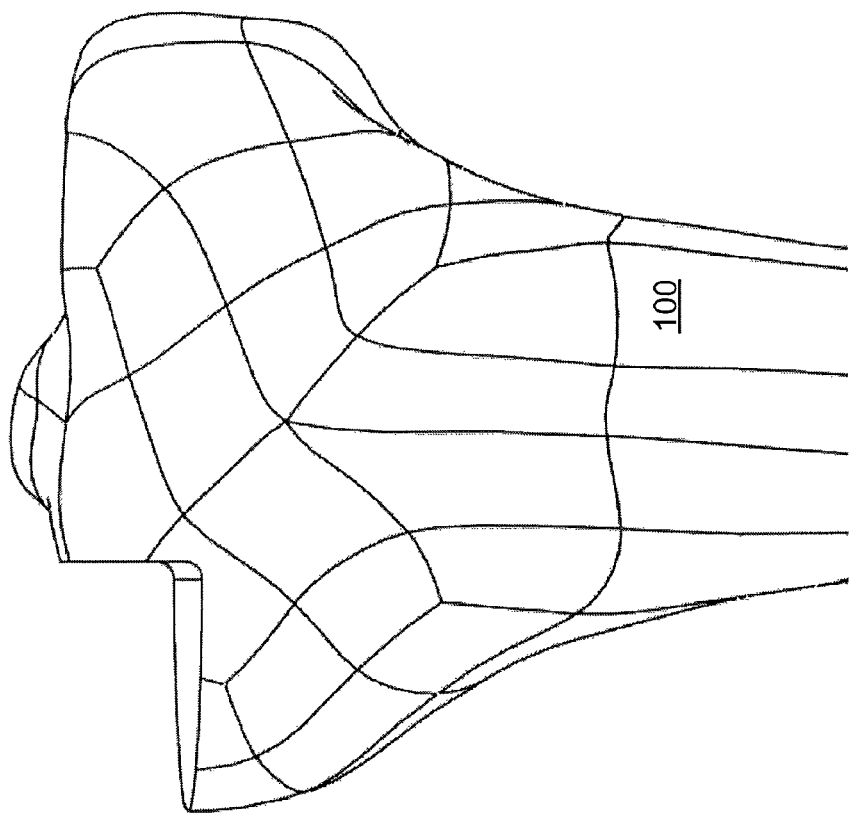
FIG. 27 shows two views of a proximal tibia after provisional resections.
Figure 27:
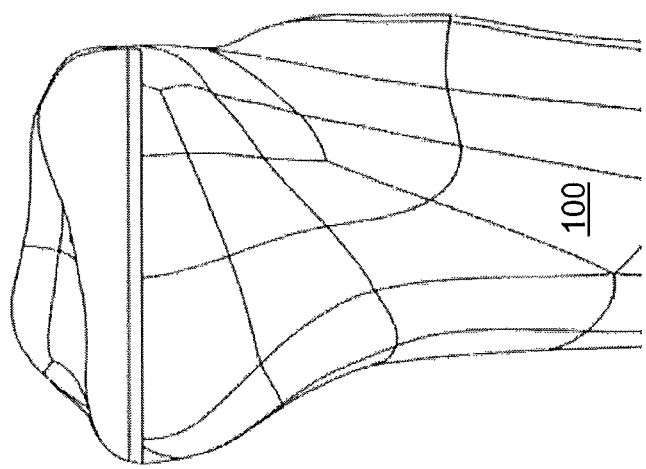
Figure 28:
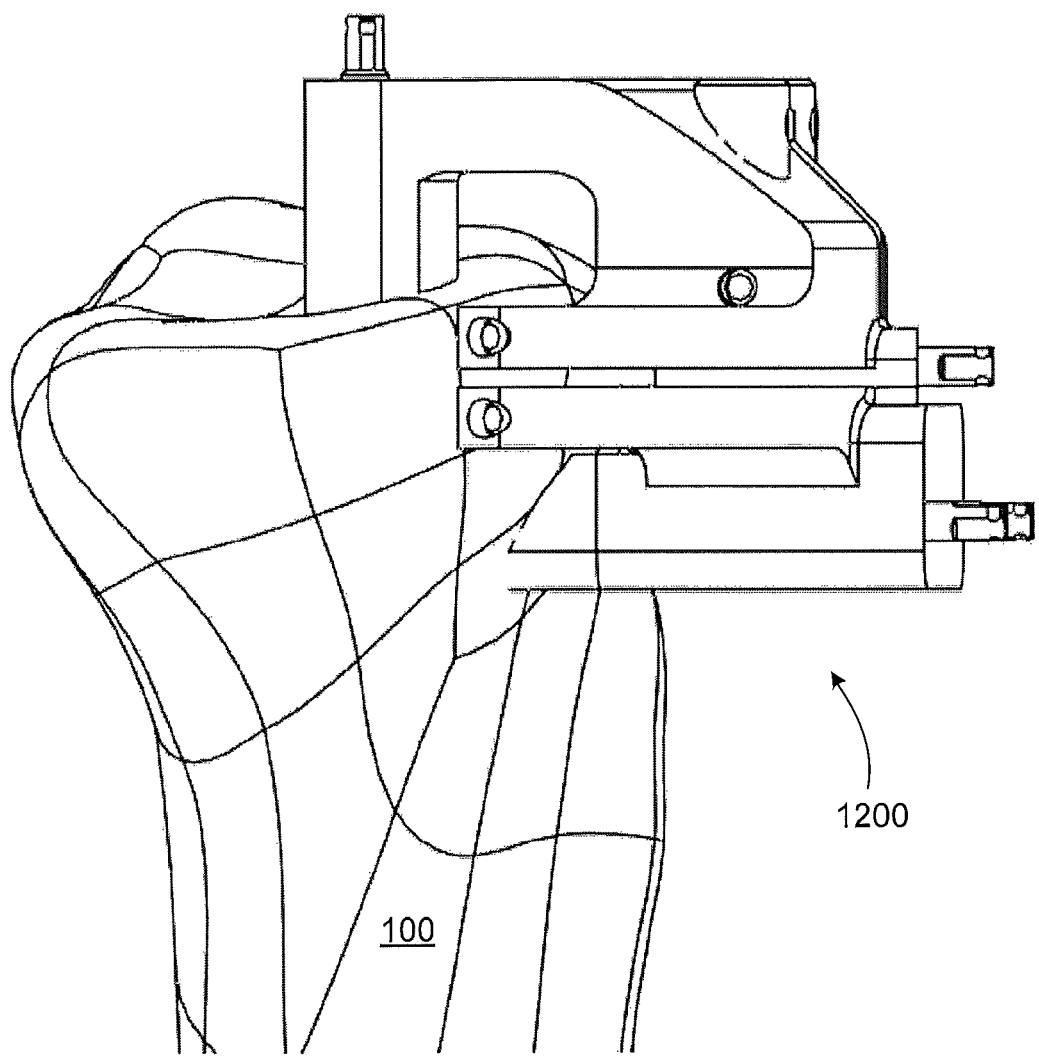
FIG. 28 shows another implementation of a patient-matched cutting guide.

FIGS. 25 and 28 show patient-matched instrumentation, in this particular implementation a patient-matched tibial cutting block 1200, for guiding provisional resections on a patient's anatomy, such as, in this particular instance, a provisional medial plateau resection and a provisional medial eminence resection. In some instances, it may be desirable to make relatively shallow provisional resections in the patient's anatomy, such as the proximal tibia 100, to afford an opportunity to evaluate certain characteristics of those provisional resections and/or possible primary resections prior to actually making one or more of those primary resections, such characteristics including, for instance, one or more of depth, medial/lateral position, anterior/posterior position, varus/valgus rotation, internal/external rotation, and/or posterior slope. As one non-limiting example, FIG. 26 illustrates primary resections made after evaluation utilizing the provisional resections of FIG. 27.

Figure 29:
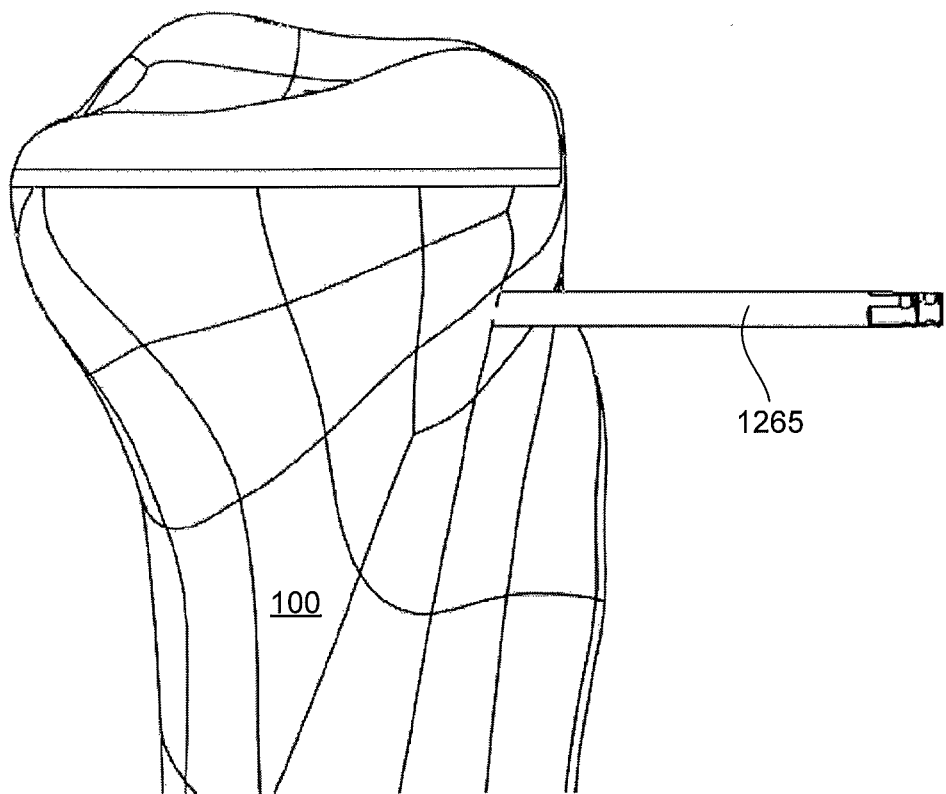
FIG. 29 shows a proximal tibia and a fixation pin.

FIG. 29 illustrates that, in some implementations, after provisional resections are made, the provisional patient-matched cutting guide can be removed, although, optionally, a pin or pins 1265 (such as a pin that had been used to temporarily secure the provisional guide to the bone) can be left in place to facilitate the positioning and/or securing of other instrumentation to the bone.

Figure 30:
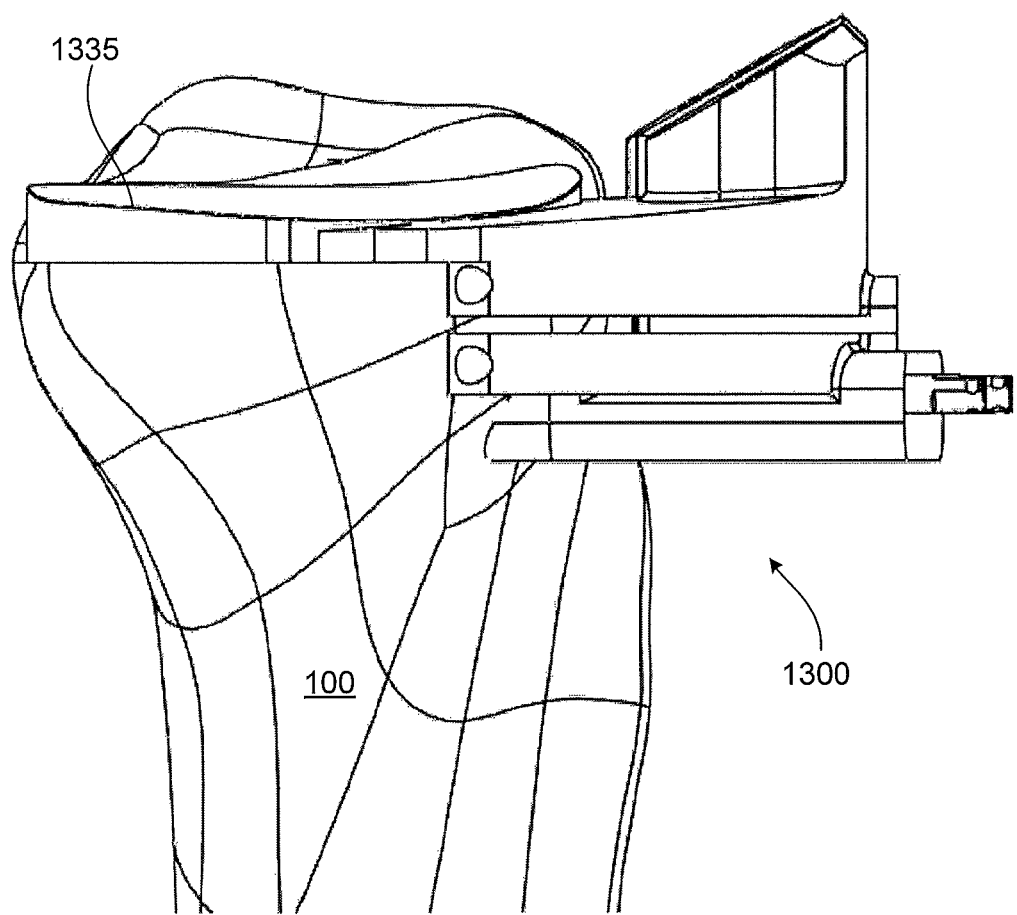
FIG. 30 shows another implementation of a patient-matched cutting guide.
Figure 31:
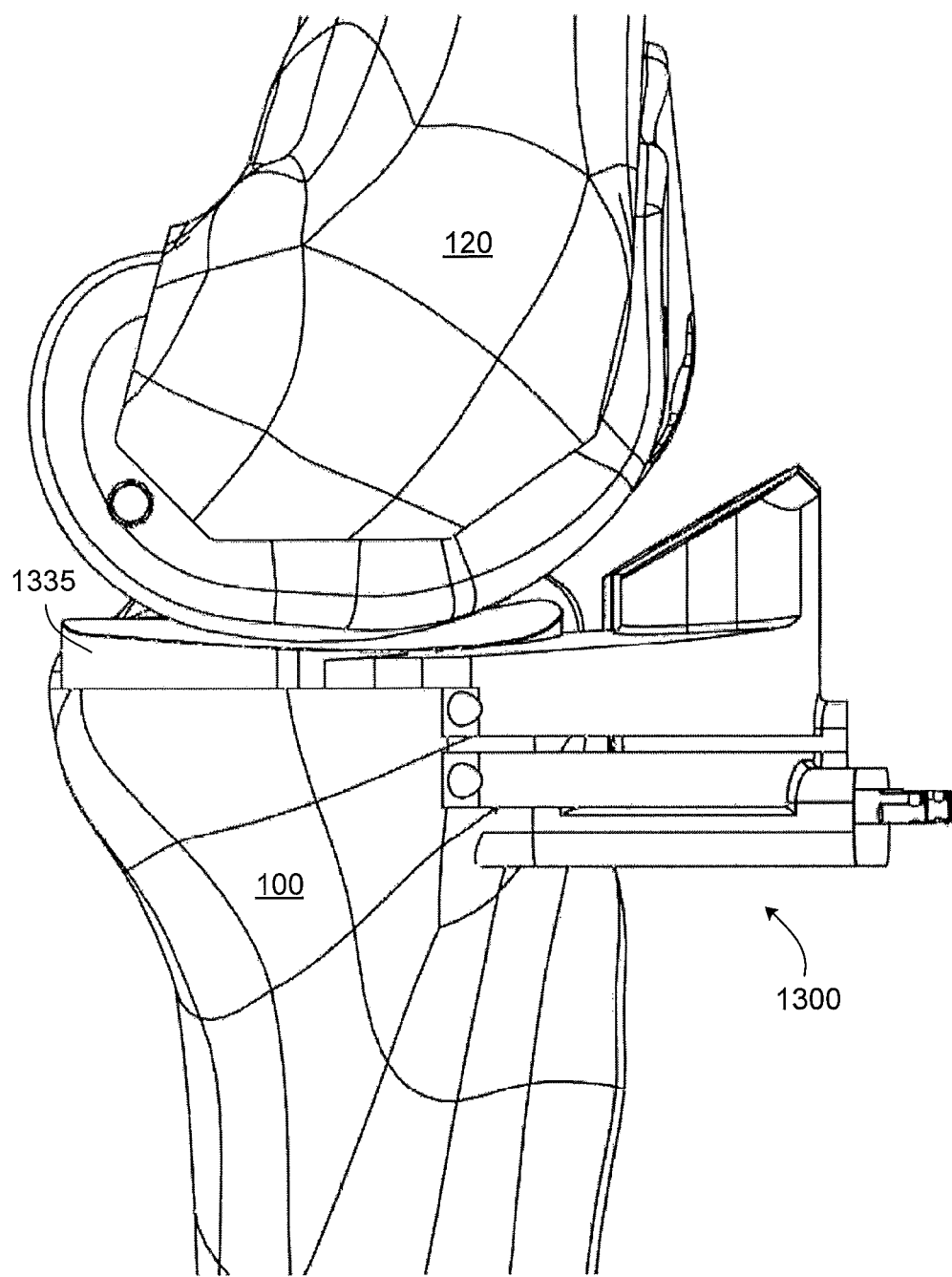
FIG. 31 shows the patient-matched cutting guide of FIG. 30 in addition to a distal portion of a femur and a femoral trial.

FIG. 30 illustrates another implementation of a patient-matched cutting guide 1300 that incorporates a trialing or balancing feature 1335 for evaluating one or more aspects of existing or possible resections to the patient's anatomy. Although FIG. 30 illustrates a patient-matched instrument, standardized cutting guides incorporating similar features are also possible. In the particular implementation illustrated in FIG. 30, the trialing/balancing feature 1335 is a trial articular surface for articulation with a femoral trial 120 (see, e.g. FIG. 31) to facilitate evaluating and/or predicting balance, tightness, biomechanics and/or other aspects of the knee if the primary resection is made using the cutting guide(s) incorporated into the instrument of FIG. 30. In this particular implementation, the trial articular surface replicates or at least substantially replicates the expected final position and orientation of at least the medial portion of a tibial implant implanted onto the primary resections defined by the instrument of FIG. 30.

Figure 32:
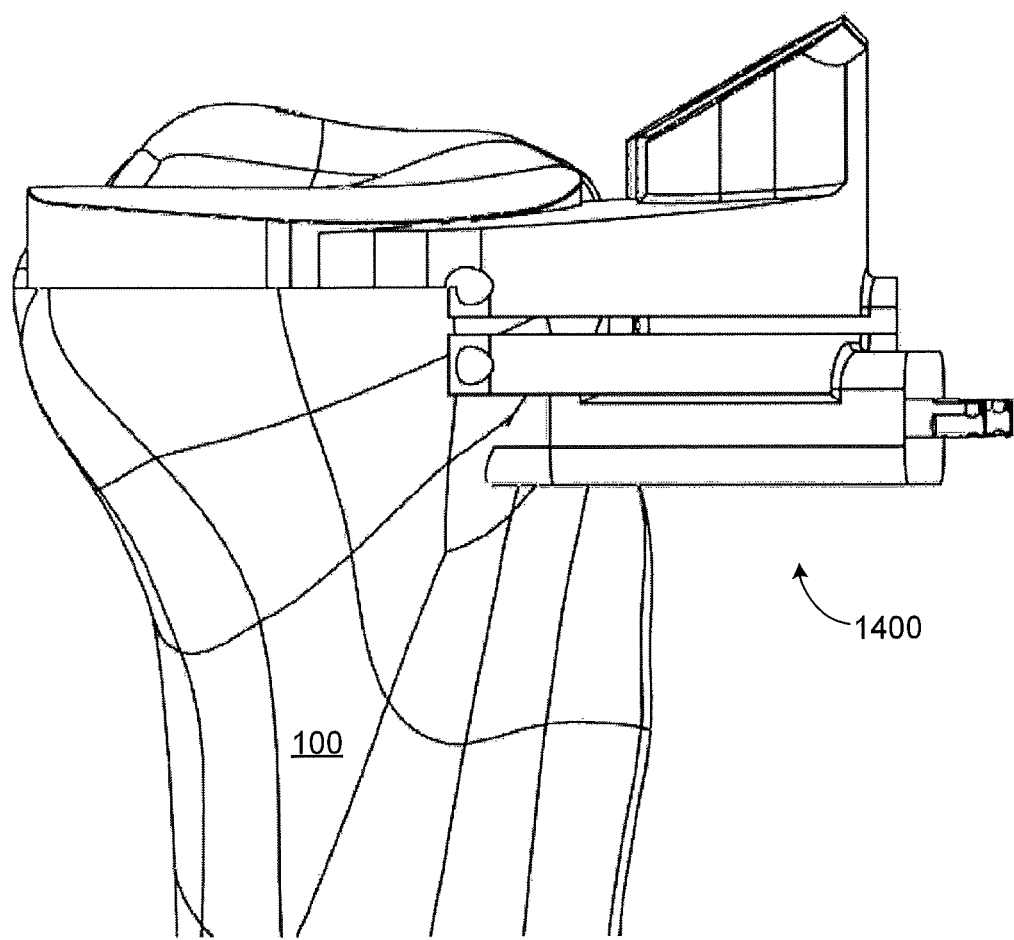
FIGS. 32 through 35 show additional implementations of patient-matched cutting guides.
Figure 33:
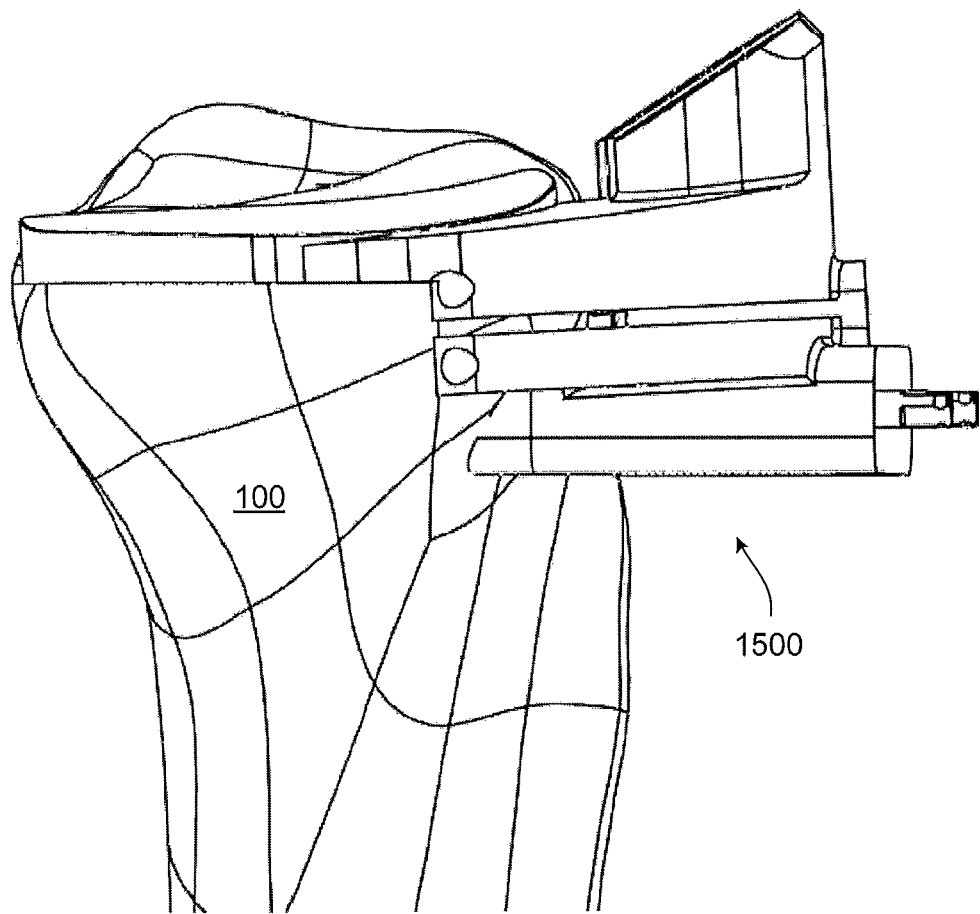

In some implementations, the instrument 1300 of FIG. 30 may be one of a kit of instruments for evaluating possible primary resections of different characteristics, such as different depths and/or posterior slopes. For instance, the instrument of FIG. 30 provides trialing and cutting guides for a primary resection of 0 degrees of posterior slope that adds −2 mm of depth to a standard resection depth; whereas FIG. 32 illustrates an instrument 1400 providing a 0 degree, 0 mm primary resection and FIG. 33 illustrates an instrument 1500 providing a −3 degree, 0 mm primary resection. Other variables could also be incorporated into such a kit. For instance, in some implementations, the set of instruments could additionally or alternatively include various varus/valgus rotations, internal/external rotations, medial/lateral positions, and/or other variables. In some implementations, a kit could be custom made for a particular surgeon and/or patient, and, in some implementations, may include only a subset of certain desired balancing/trialing options.

Figure 34:
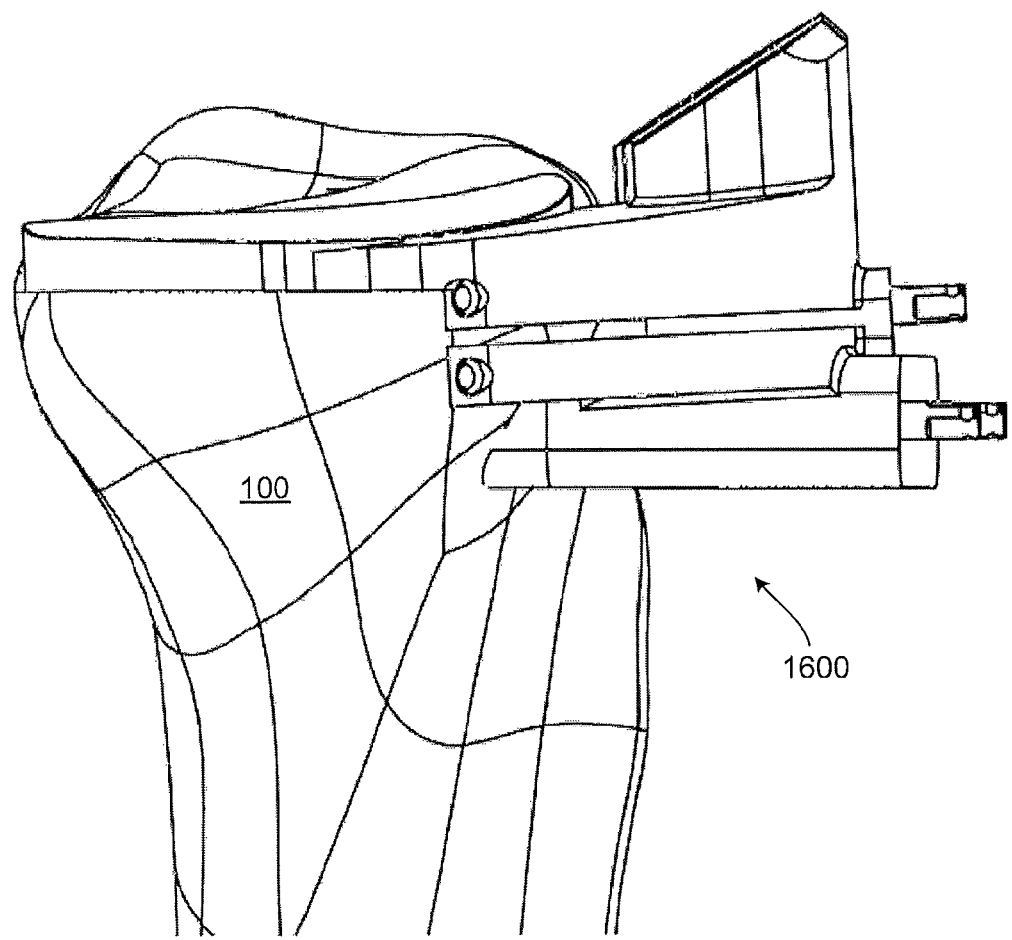
Figure 35:
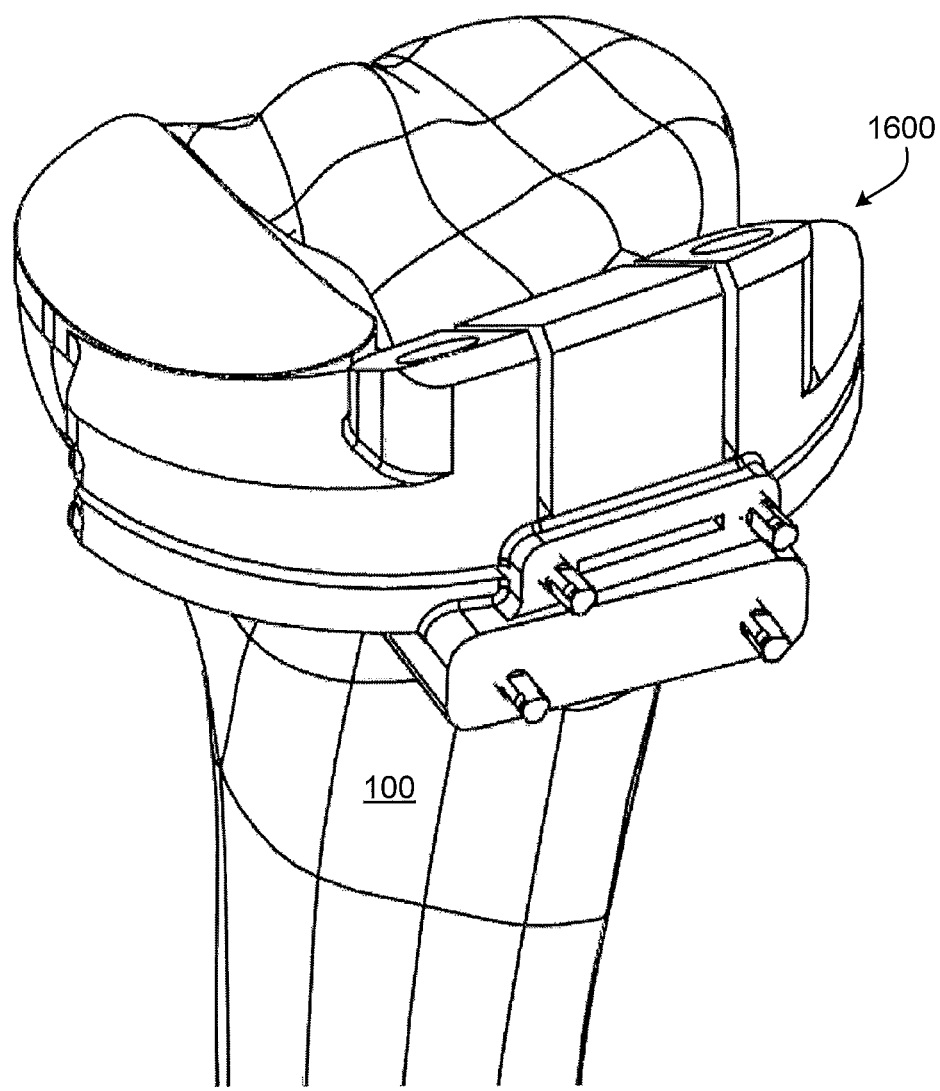
Figure 36:
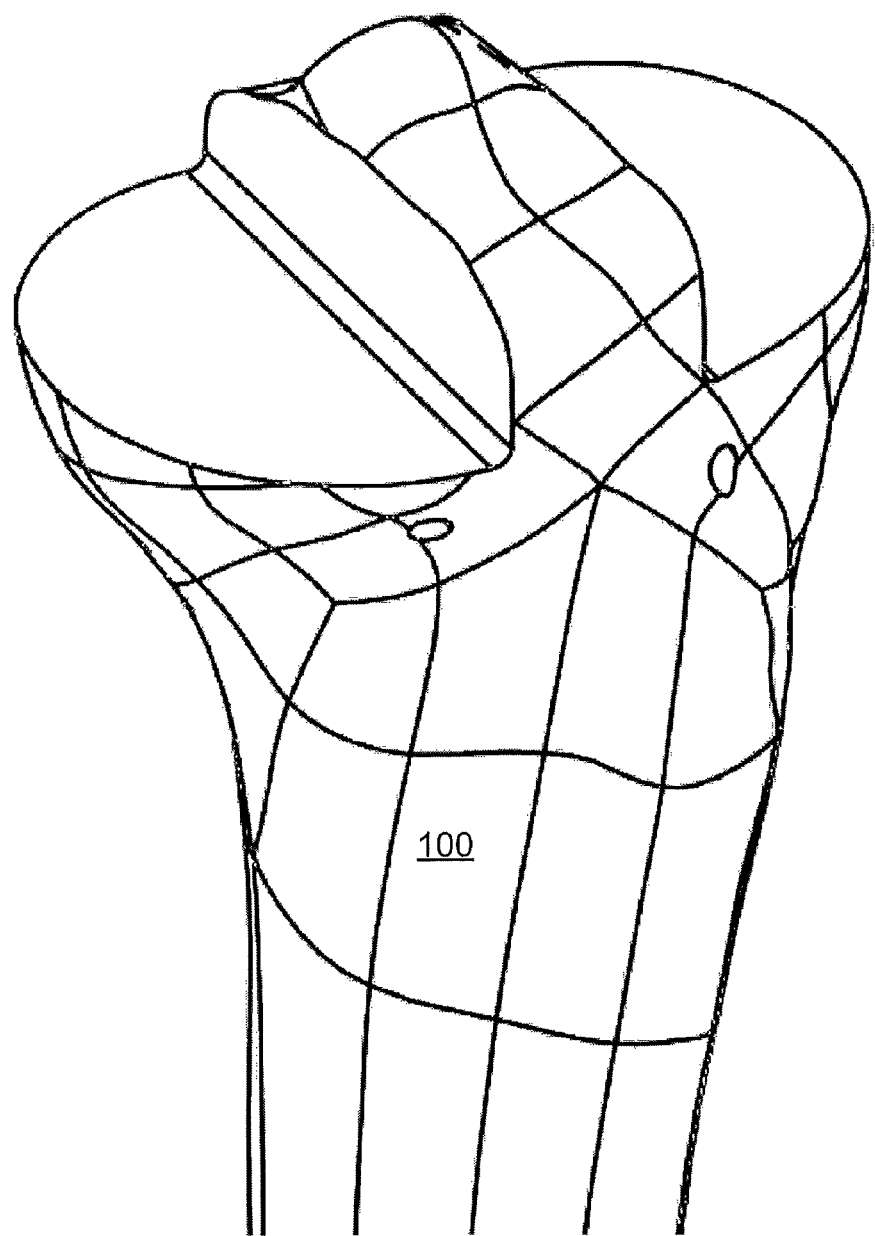
FIG. 36 shows a proximal tibia after resection.

FIGS. 34-36 illustrate an implementation 1600 in which, after balancing/trialing and once an acceptable instrument is identified, the selected instrument can be further pinned to the proximal tibia, if desired, and one or more resections can be made using that instrument. In the particular implementation shown in FIG. 36, lateral resections have also been performed, which, as mentioned above, could be accomplished with the same instrument used for the medial resections or a different instrument, one or both of which may or may not be matched to the particular patient.

Figure 37:
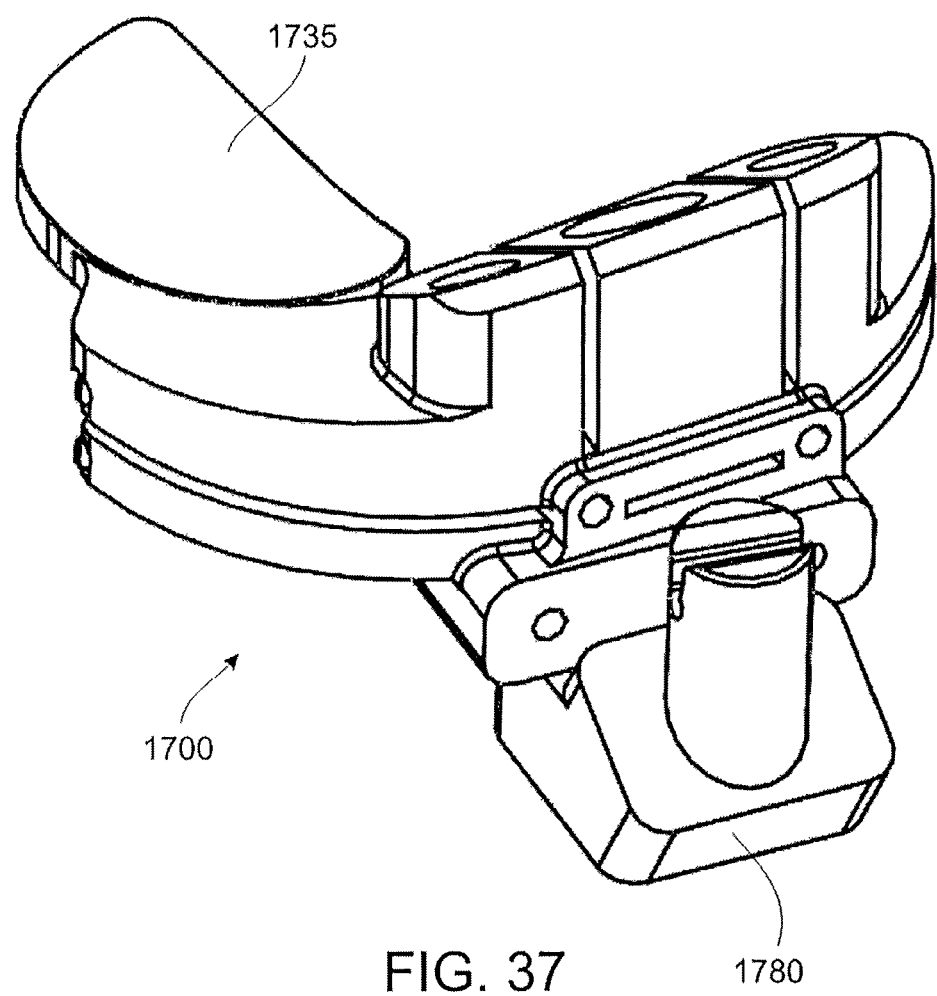
FIG. 37 shows another implementation of a patient-matched cutting guide.
Figure 38:
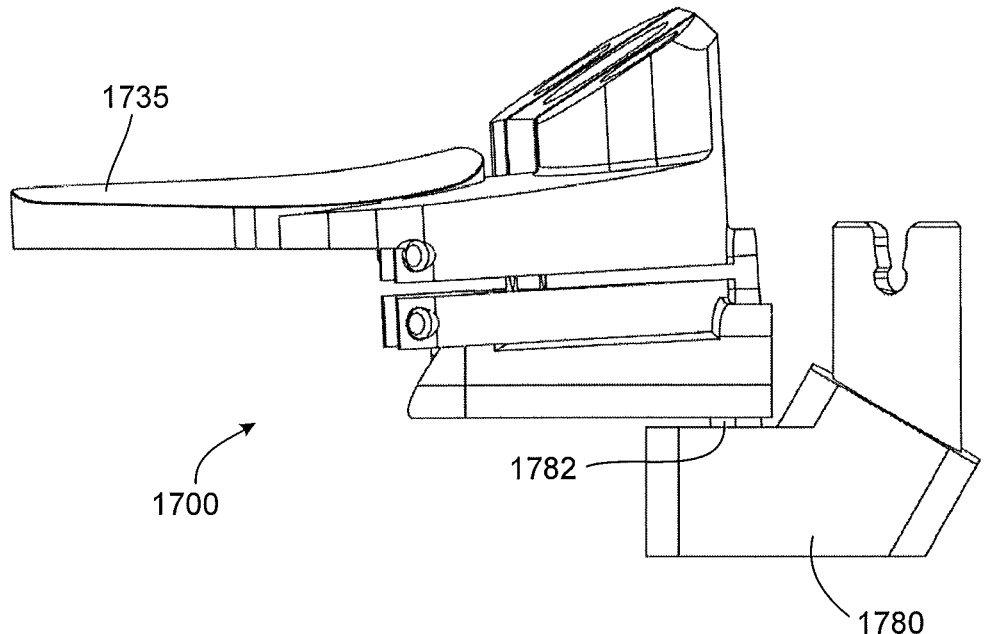
FIGS. 38 through 42 show additional views of the patient-matched cutting guide of FIG. 37.
Figure 39:
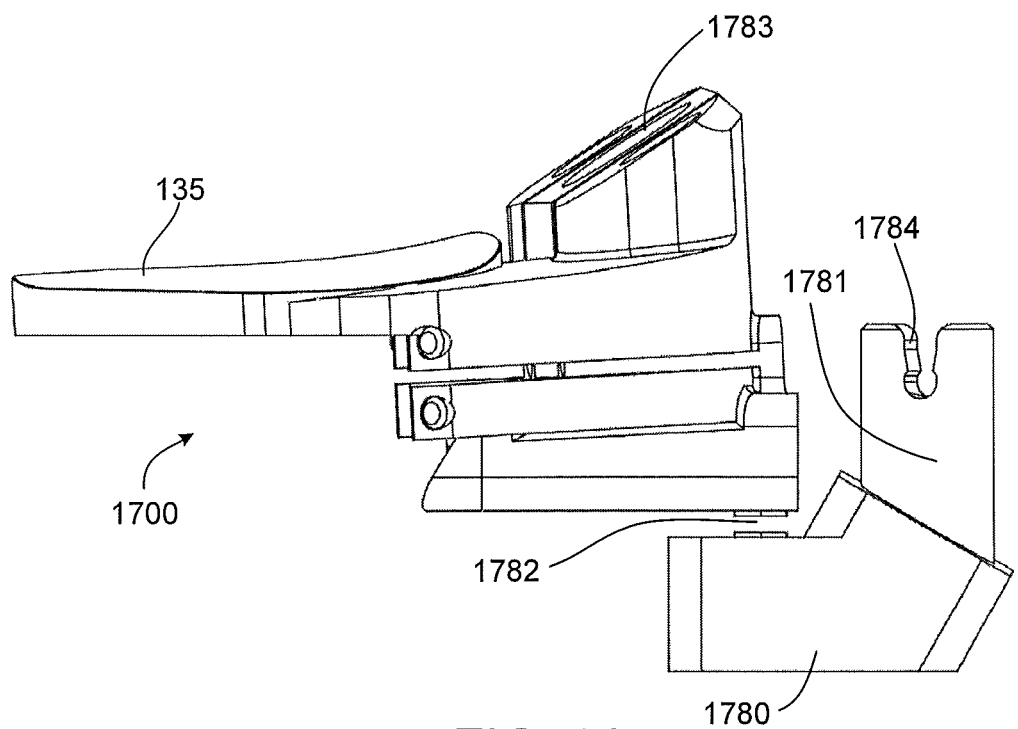
Figure 40:
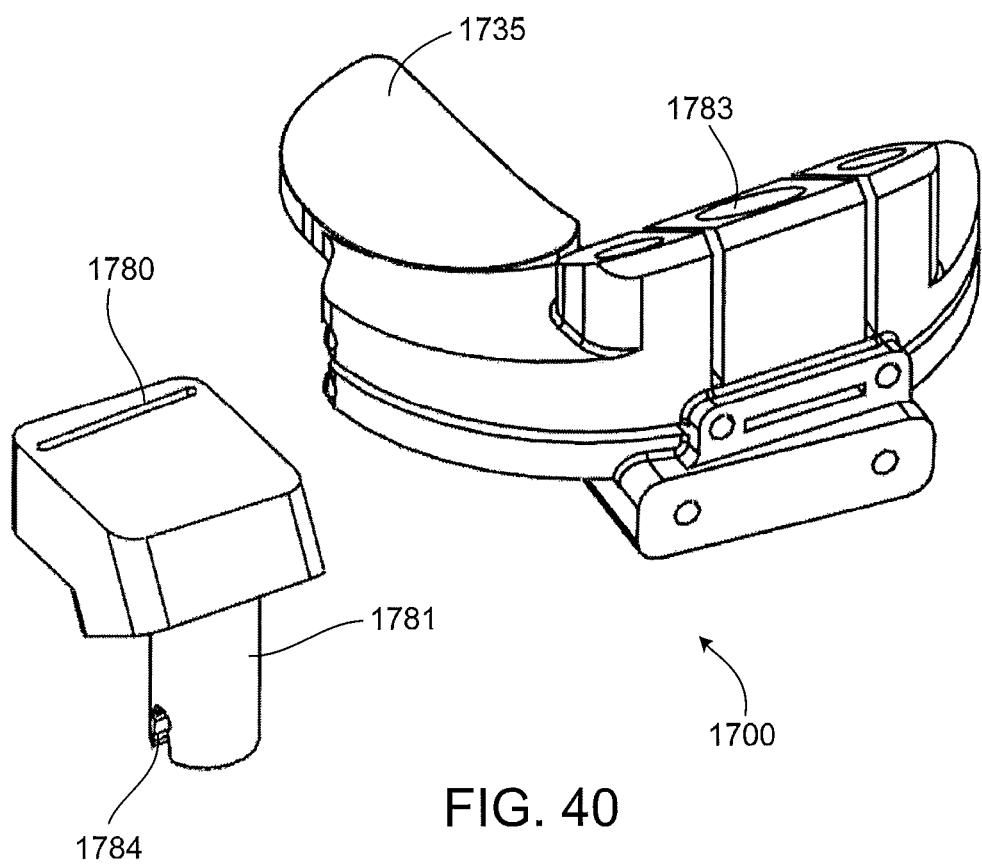

FIG. 37 illustrates an implementation 1700 similar to the instrument shown in FIG. 30, but that also includes a detachable component 1780. The detachable component 1780 is an anterior eminence resection guide, which, initially is not positioned for use but is positioned to avoid interfering with the trialing/balancing process that, in some implementations, may occur prior to resection of anterior portions of the eminence. For instance, in some implementations, when positioned for use, the anterior eminence resection guide 1780 might be prone to interfering with portions of the femoral trial component 1735. In this particular implementation, the anterior eminence resection guide 1780 is initially positioned where it is not prone to interfering with the trialing/balancing process, and, once that process is completed, can be detached (e.g. through frangible connections or other suitable structures or mechanisms) and reconnected to the instrument in the proper position and orientation for use. FIGS. 38 through 42 illustrate the anterior eminence resection guide 1780 as it is first attached, and then subsequently detached at a frangible connection points, and then subsequently placed into a position and orientation for guiding the resection of anterior portions of the eminence.

In the particular implementation of FIGS. 38 through 42, a frangible connection 1782 between the anterior eminence resection guide 1780 and the rest of the instrument includes a series of breakable pins (see, e.g., FIG. 44, which shows the pins after breaking), although other frangible or non-frangible mechanisms are also possible. For instance, in some implementations, the connection is not designed to be breakable, but otherwise allows the component to be moved from a first position to a second position (e.g. a hinge or other mechanism).

Figure 41:
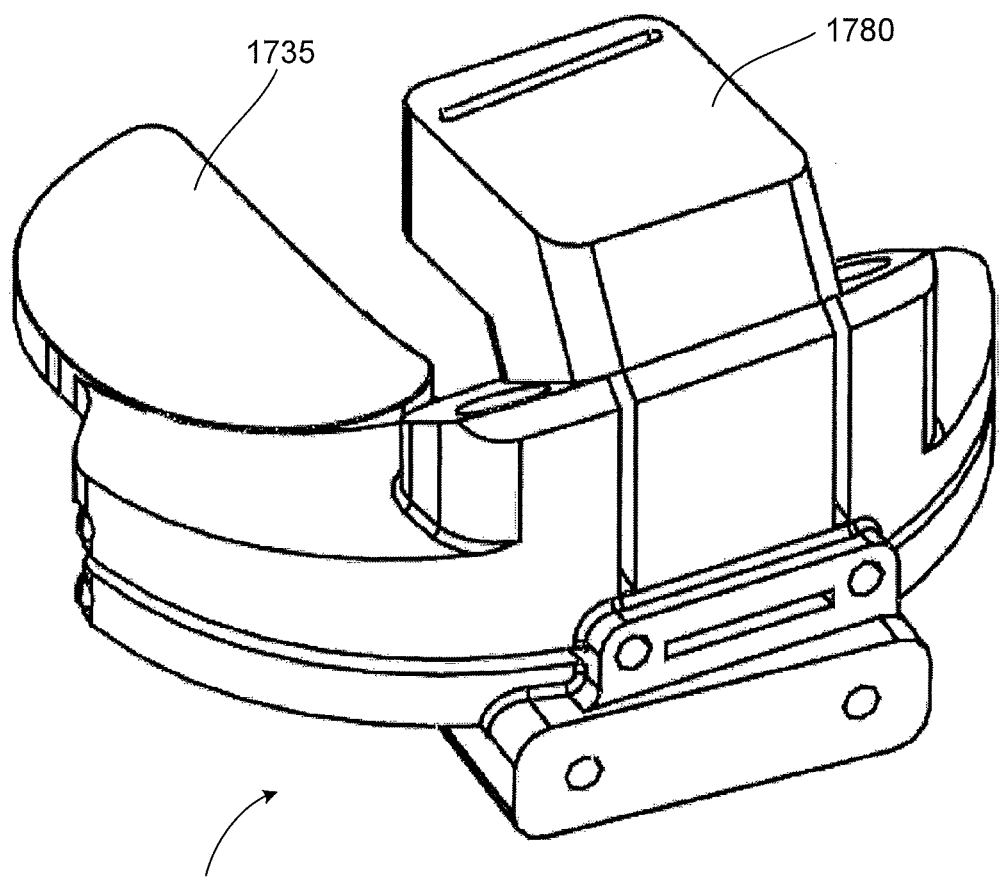
Figure 42:
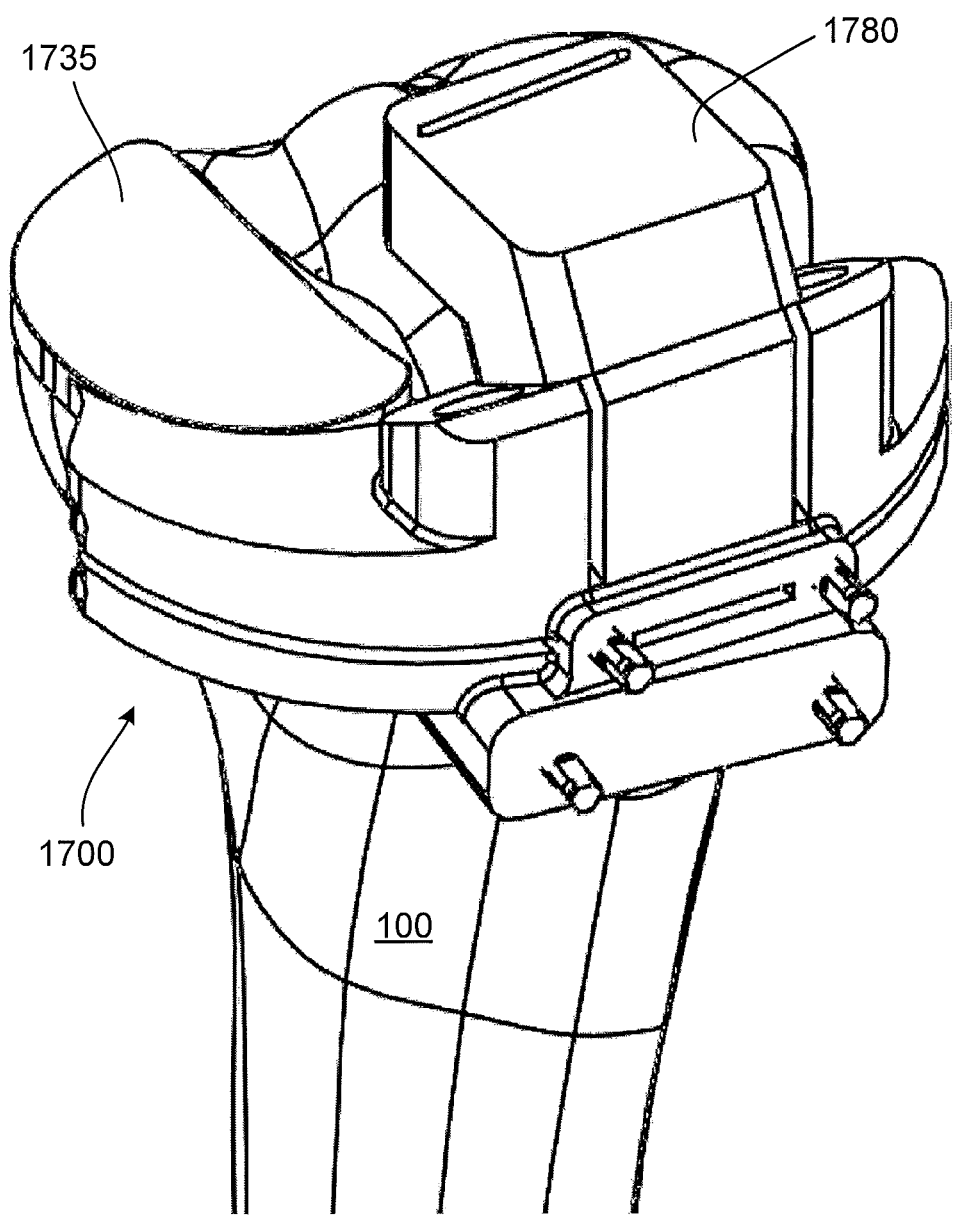
Figure 43:
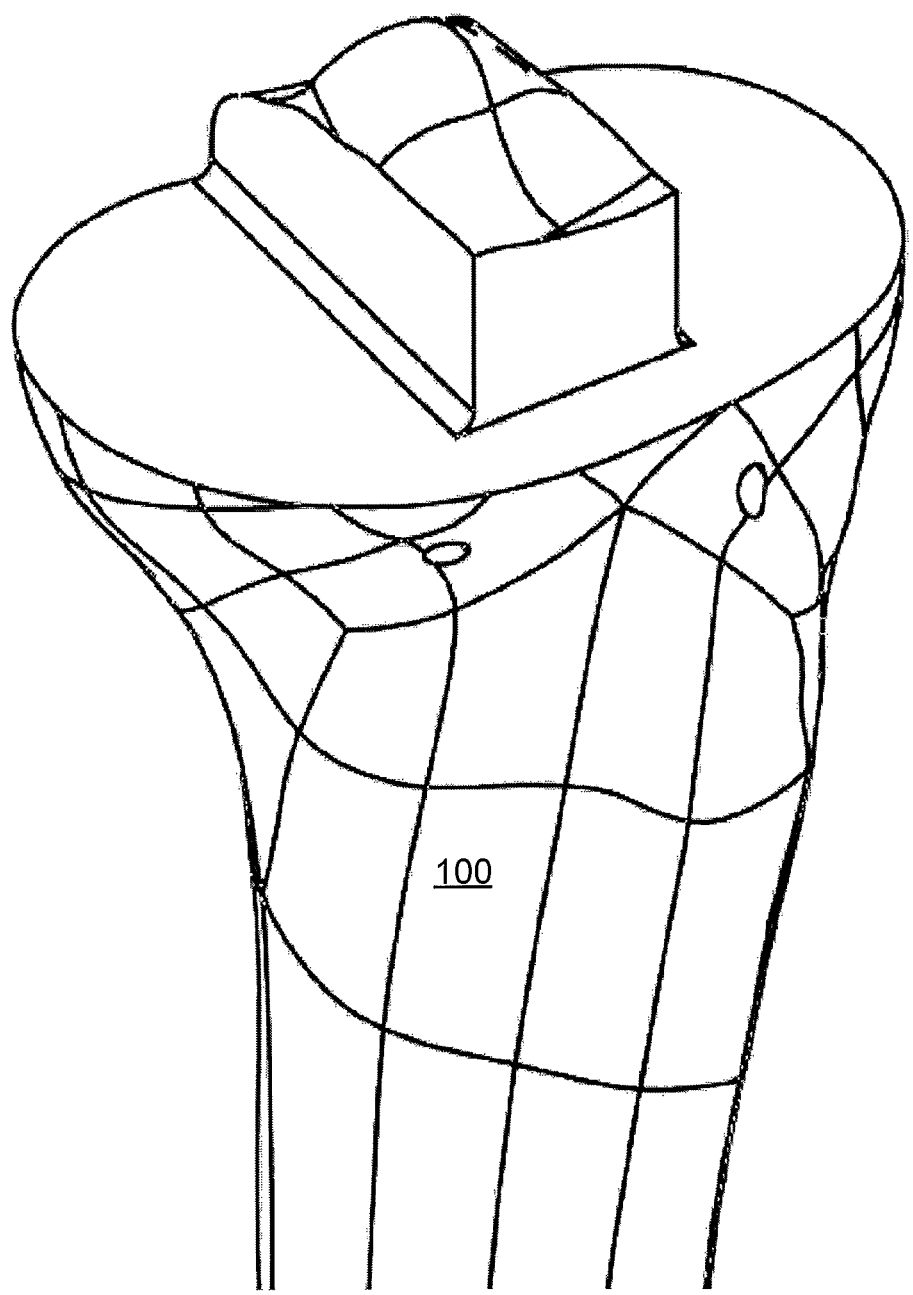
FIG. 43 shows a proximal tibia after resection.

In the particular implementation of FIGS. 38 through 42, the anterior eminence resection guide 1780 is connected and properly positioned and oriented for use by inserting the post 1781 of the anterior eminence resection guide 1780 into a cylindrical hole 1783 and snapping the resilient groove 1784 onto one of the horizontal reinforcement members discussed above, a portion of which may extend through the cylindrical hole (FIG. 41). Once in position, the instrument 1700 may be placed on the tibia for use (FIG. 42). The connection between the groove and horizontal member, in some implementations, may function to both secure the two structures together as well as properly orient them with respect to one another. Other connection and orienting mechanisms are also possible. FIG. 43 illustrates the proximal tibia 100 after resection using the instrument shown in FIGS. 38 through 42.

Figure 44:
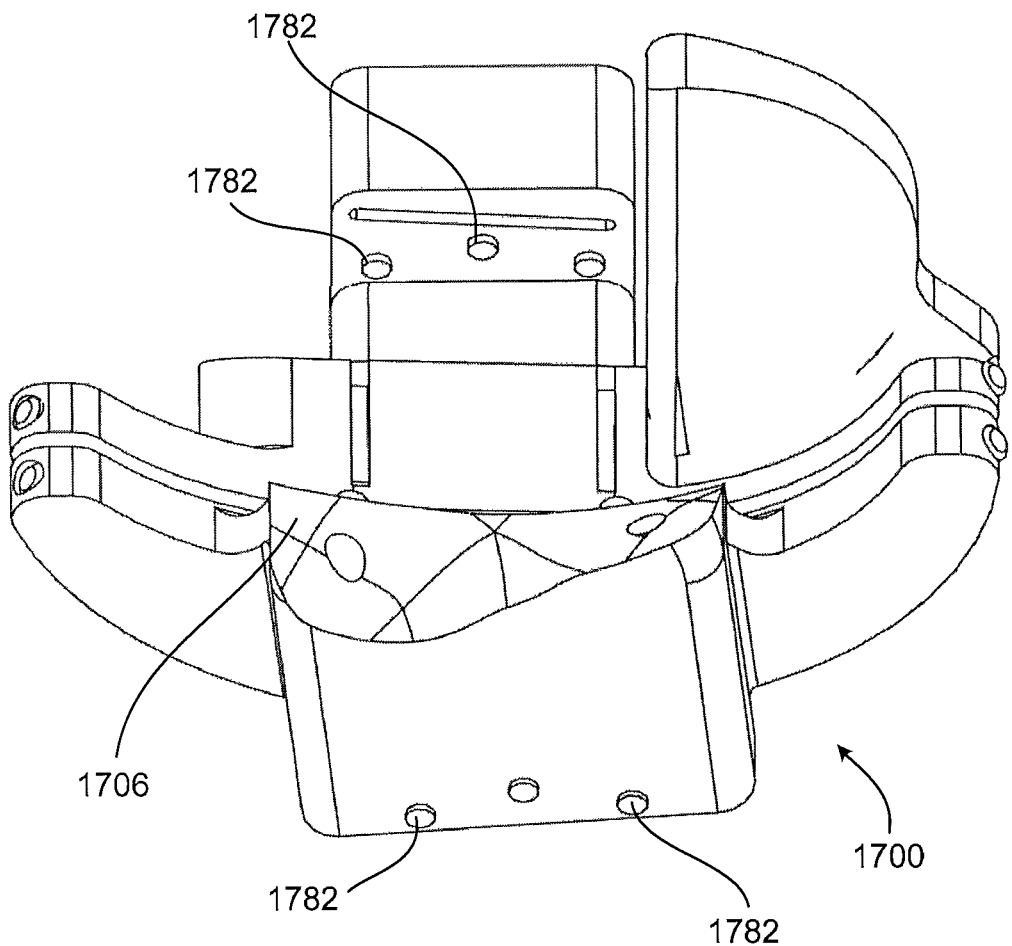
FIG. 44 shows another view of the patient-matched cutting guide of FIG. 37.

FIG. 44 shows an interior (bone facing) side of the patient-matched instrument 1700 of FIG. 37. As shown in this particular implementation, the instrument 1700 includes a patient-matched surface 1706 that conforms to or references the unique geometry of the patient's anatomy to ensure that the instrument 1700 is properly positioned and oriented with respect to the particular patient's anatomy.

These and other patient-matched surfaces can be included to contact various portions of the bony or other anatomy of the patient to facilitate positioning and orienting the instrument on the particular patient's anatomy. For instance, in the implementation shown in FIG. 2, the instrument additionally includes patient-matched surfaces on the undersides of at least portions of the outriggers extending from the main body of the instrument. Other numbers, locations and orientations of patient-matched surfaces are also possible. Other implementations may include point contact surfaces.

Figure 45:
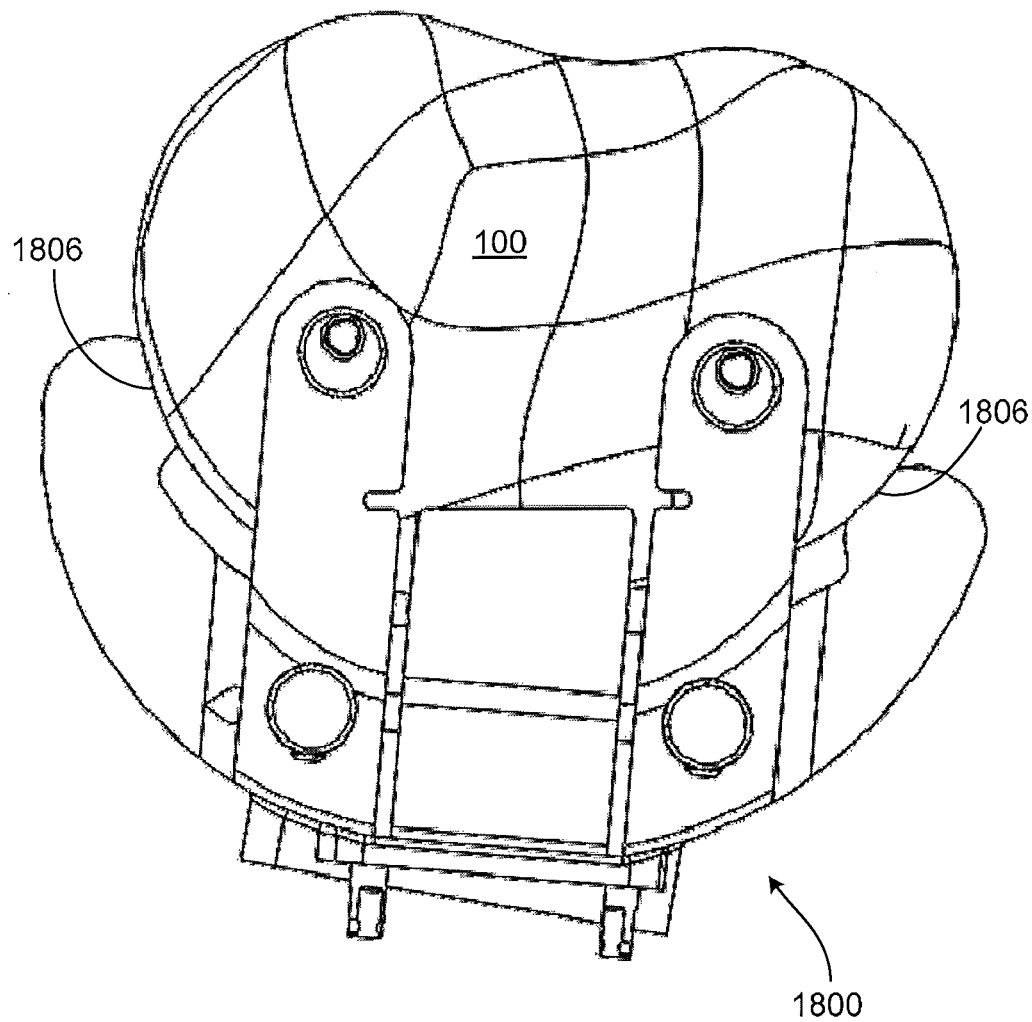
FIGS. 45 and 46 show another implementation of a patient-matched cutting guide.
Figure 46:
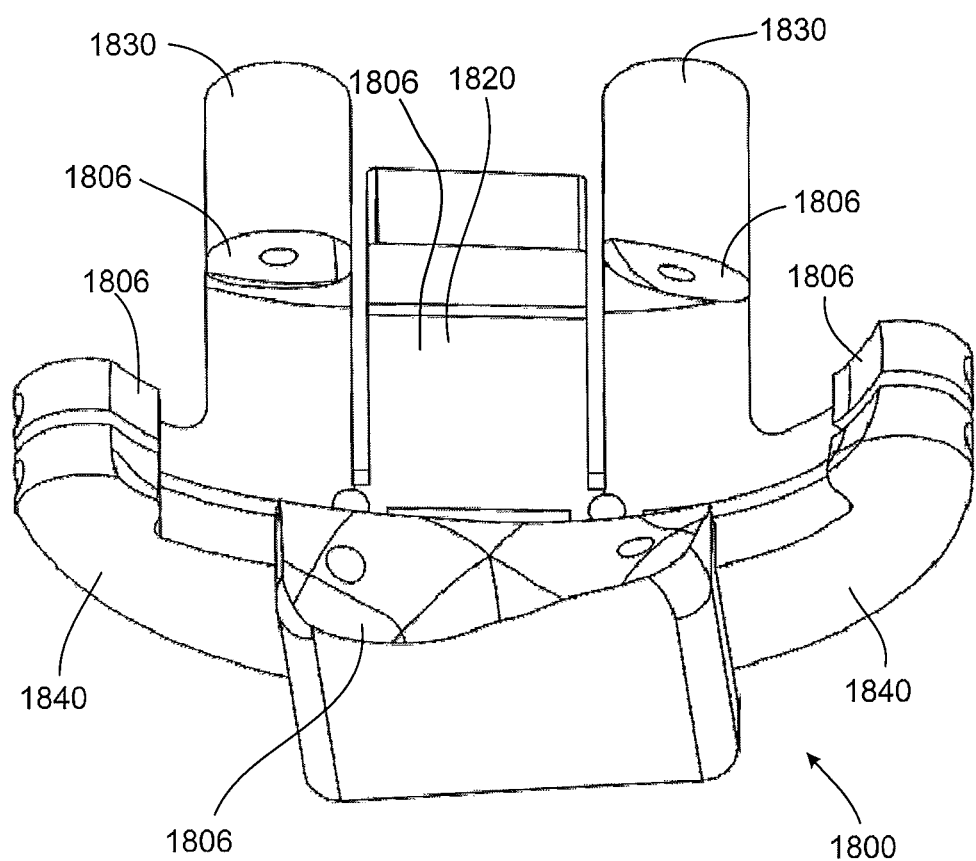
Figure 47:
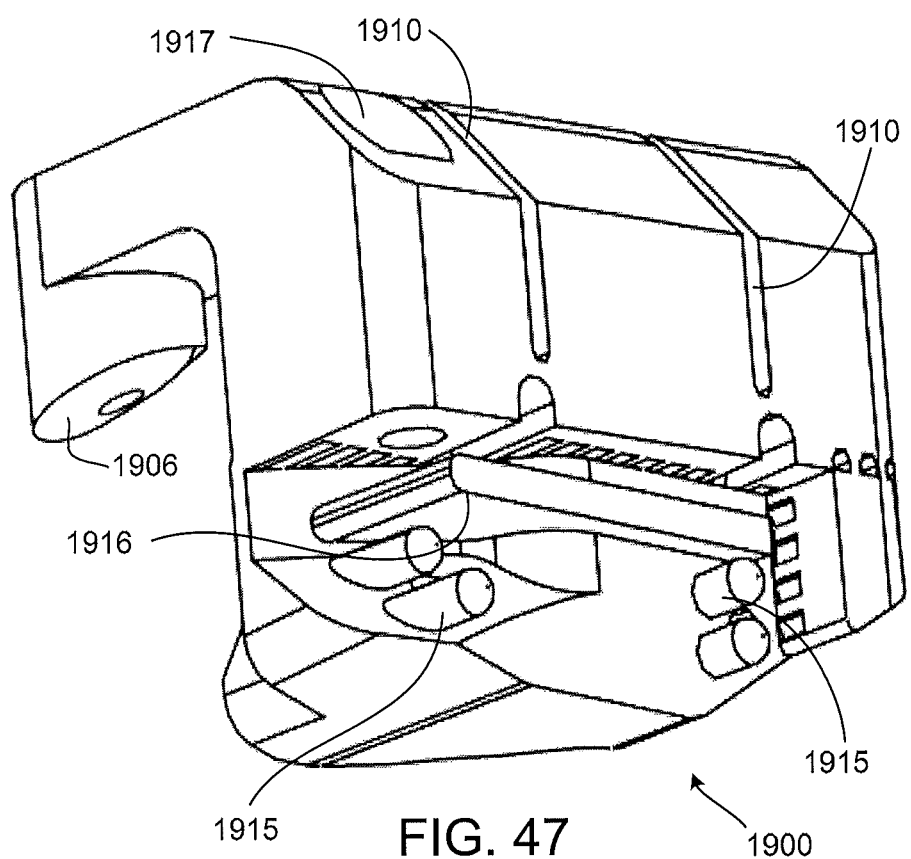
FIGS. 47 through 50 show another implementation of a patient-matched instrument.
Figure 48:
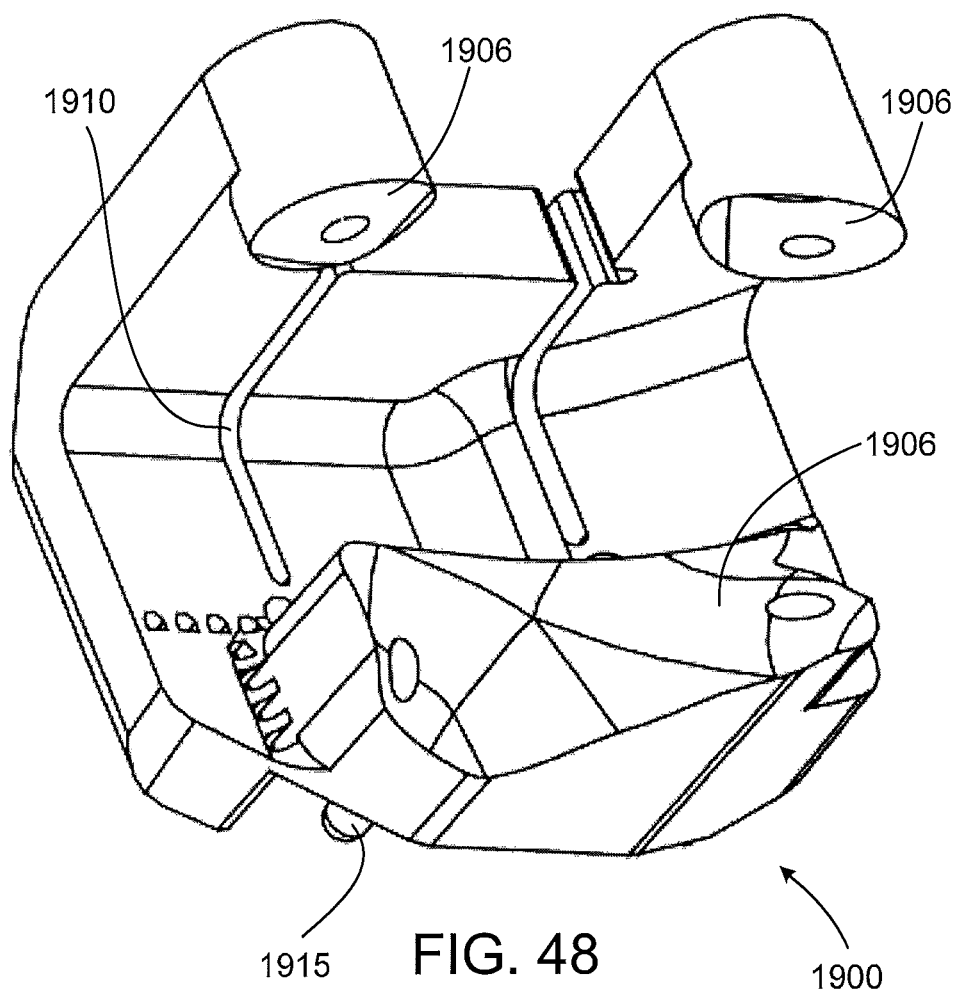
Figure 49:
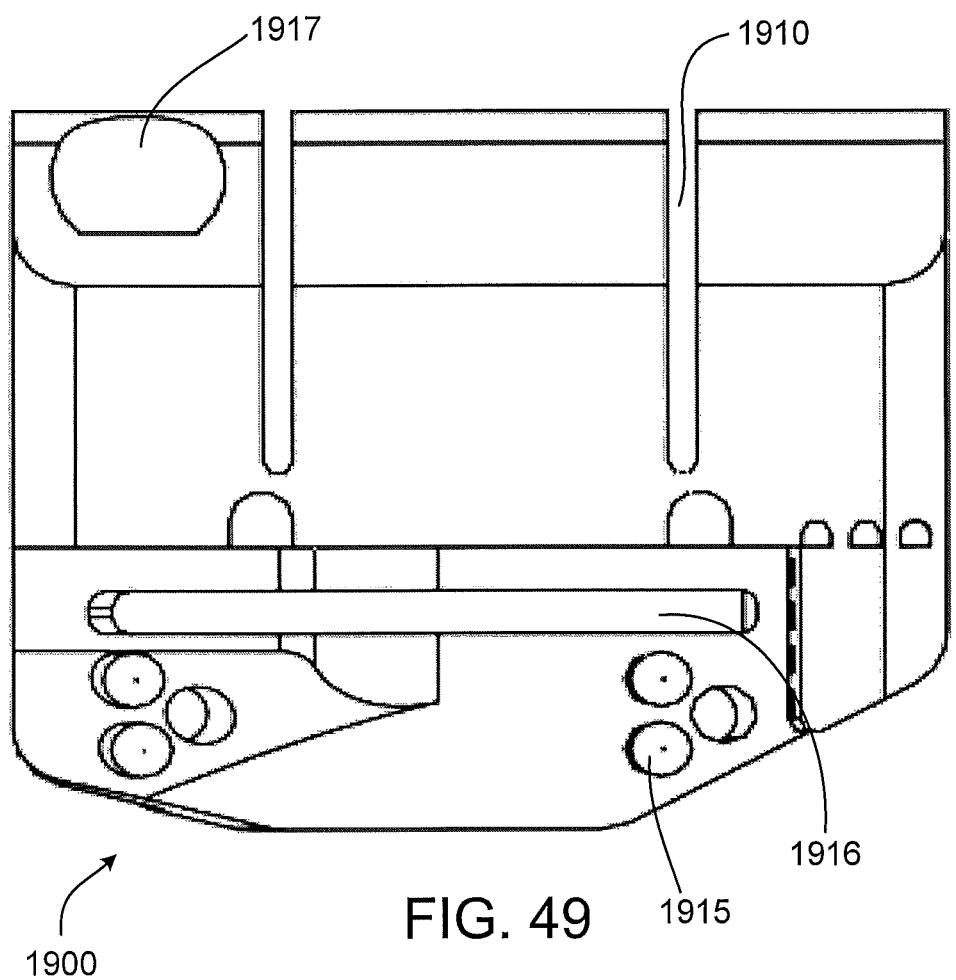
Figure 50:
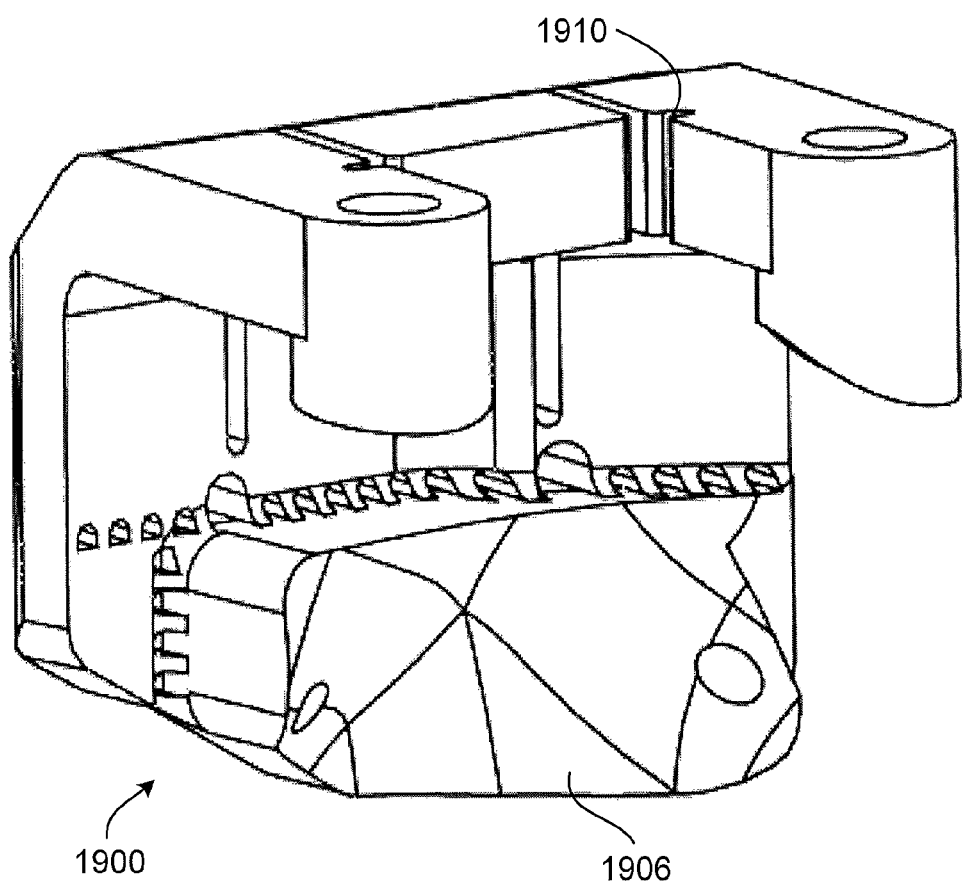

FIGS. 45 and 46 show another implementation in which the patient-matched instrument 1800 includes patient-matched surfaces 1806 on the main body 1820, the outriggers 1830 and the wings 1840 of the instrument. Other implementations may include point contact surfaces.

FIGS. 47 through 79 illustrate alternative implementations of patient-matched instruments and non-patient-matched, standard, instruments that can be used together. FIGS. 47 through 50 illustrate an implementation of a patient-matched instrument 1900 that includes guide features 1910 (such as cutting guides) as well as mounting features 1915, 1916 for attachment of additional components, such as standard instrumentation. The patient-matched instrument shown in FIGS. 47 through 50 includes patient-matched surfaces 1906 on the main body and outriggers that are customized to a particular patient's anatomy, to facilitate correctly positioning and orienting the instrument on the patient's anatomy. In the particular implementation shown in FIGS. 47 through 50, the patient-matched surfaces 1906 of the instrument 1900 are sufficient to position and orient the instrument in all of the degrees of freedom relevant to the tibial resections of a bi-cruciate retaining knee arthroplasty procedures, although, in other implementations, these surfaces or point contact surfaces and or other attributes of the instrument may only be relevant to establishing some of the degrees of freedom relevant to such a procedure or other procedures.

The patient-matched instrument 1900 shown also includes guide slots 1910 for guiding a saw blade or blades. In this particular implementation, the guide slots 1910 guide the two vertical eminence resections and the vertical anterior eminence resection of a bi-cruciate retaining arthroplasty procedure, although, in other implementations, other numbers, positions, orientations and other types of guide features 1910 could be included in the patient-matched instrument 1900 for facilitating bi-cruciate retaining knee arthroplasty procedures or other types of knee, hip, or other orthopaedic procedures on other anatomy or joints. In still other implementations, the patient-matched instrument 1900 does not include any guide features 1910, but rather simply serves as a mount for securing and/or positioning a standard instrument or instruments that are mounted or otherwise associated with the patient-matched instrument.

Figure 51:
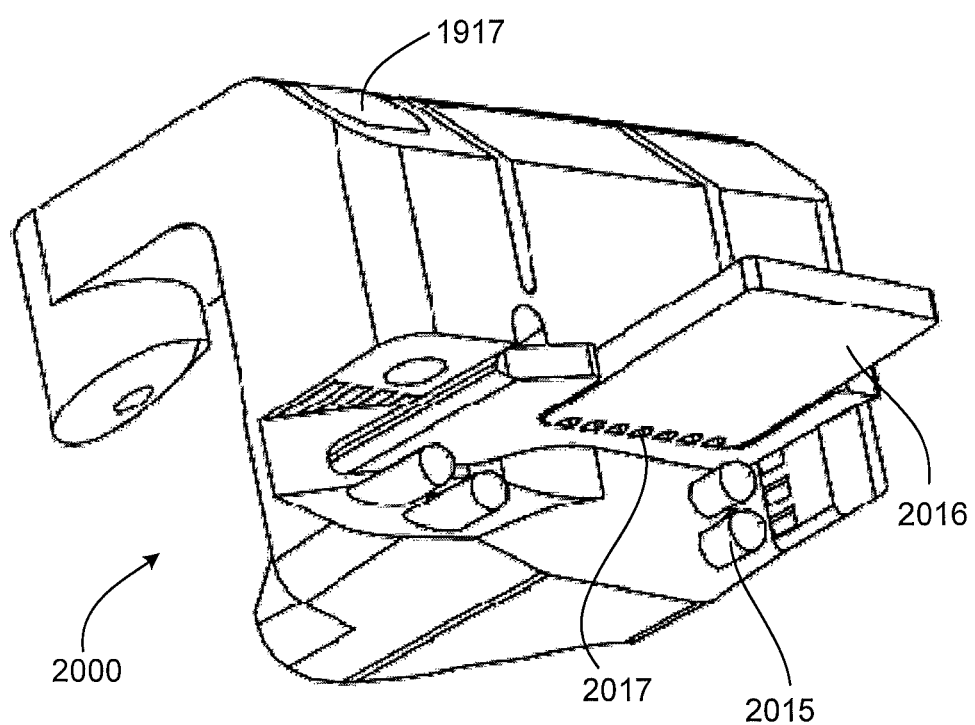
FIG. 51 shows another implementation of a patient-matched instrument.

The patient-matched instrument shown in FIGS. 47 through 50 includes mounting features 1915, 1916 for facilitating the association of additional components with the patient-matched instrument 1900. The particular instrument shown in FIGS. 47 through 50 includes several protrusions that are positioned, oriented and shaped to interact with structures of the additional component, the protrusions including several cylindrical pins 1915 as well as a substantially planar protrusion 1916. FIG. 51 shows an alternative implementation where the planar protrusion 2016 is an elongated tongue that includes a frangible portion 2017. In some implementations, the frangible protrusion or tongue 2016, when attached, may facilitate positioning and orienting a first instrument with respect to the patient-matched instrument, and, after removal, the remaining portion of the tongue 2016 may facilitate positioning and orienting a second instrument. As shown in FIGS. 47 through 51, other portions of the patient-matched instrument 1900 can also be frangible. The patient-matched instruments 1900, 2000 of FIGS. 47 through 51 also include a vertical aperture 1917 for receiving a mounting bolt, as described further below. The patient-matched instruments 1900, 2000 of FIGS. 47 through 51 also include apertures for receiving pins or other devices for fastening the patient-matched instrument to the patient's anatomy.

FIGS. 52 through 60 illustrate an implementation of a standard, non-patient-matched instrument 2100 that may be used in conjunction with the patient matched instruments of FIGS. 47 through 51. The standard instrument of FIGS. 52 through 60 includes a slot 2118 (FIG. 55) and several apertures 2119 extending at least partially through the body of the instrument that are sized, positioned and oriented to interact with the various protrusions of the patient-matched instruments 1900, 2000 of FIGS. 47 through 51 to facilitate securing, or at least positioning and orienting, the standard instrument with respect to the patient-matched instrument. In the particular implementation shown, the standard instrument 2100 can only be mounted to the patient-matched instrument in a single position and orientation such that the position and orientation of the patient-matched instrument 2100 (when placed on the patient's anatomy) establishes the position and orientation of the standard instrument 2100 (with respect to the patient's anatomy). In other implementations, the position and/or orientation of the standard instrument 2100 can be adjusted in at least some degrees of freedom with respect to the patient-matched instrument, even when the standard instrument 2100 is mounted to the patient-matched instrument. For instance, in some implementations, the standard instrument 2100 may be able to pivot and slide to at least some extent on the tongue of the patient-matched instrument, and the connection between the two components could function as a planar joint. In other implementations, the multiple apertures in the standard instrument 2100 may provide several discrete different positions and/or orientations in which to mount the standard instrument 2100 on the patient-matched instrument. In still other implementations, the position and/or orientation of the standard instrument 2100 with respect to the patient-matched instrument could be adjusted in other ways.

The standard instrument 2100 of FIGS. 52 through 60 also includes a locking mechanism 2103 for securing components positioned in the slot 2118 of the instrument, such as a tongue or other protrusion extending from the patient-matched instrument, or a feature of other patient-matched or non-patient-matched instrumentation. In the particular implementation of FIGS. 52 through 60, the standard instrument 2100 includes a cam mechanism that is actuated by moving a paddle arm 2108 from an unlocked position (see FIG. 57) to a locked position (see FIG. 58). The standard instrument 2100 of FIGS. 52 through 60 also includes a threaded aperture 2109 for receiving a mounting bolt as a mechanism for further or alternatively securing the standard instrument to a patient-matched instrument and/or other component.

The standard instrument 2100 of FIGS. 52 through 60 includes several cylindrical openings 2116 for receiving bone pins to secure the instrument to the patient's anatomy. In the particular implementation shown, the instrument includes multiple pairs of parallel openings extending from an anterior face of the instrument to a posterior face of the instrument, which may facilitate discrete adjustment of the instrument with respect to the patient's anatomy (e.g. allowing for discrete adjustment of superior/inferior positioning of the instrument to adjust depth of cut or for other adjustments or purposes). The instrument of FIGS. 52 through 60 also includes an oblique opening 2117, also for receiving a bone pin, to further secure the instrument onto the patient's anatomy. As stated above, in some implementations, some or all of these openings can be used for other purposes, such as receiving cylindrical protrusions on the patient-matched instrument to facilitate the positioning and orienting of the standard instrument with respect to the patient-matched instrument.

The standard instrument of FIGS. 52 through 60 includes a planar superior face 2102, which, in some implementations, may function as a resection guide for guiding a planar cutting device such as an oscillating saw blade. In the particular implementation shown, the planar face is sized, positioned and oriented on the instrument to facilitate a planar medial resection of the proximal tibia, although other configurations are also possible for guiding other resections. In the particular implementation shown, the standard instrument 2100 of FIGS. 52 through 60 can be used in conjunction with the additional component 2400 shown in FIGS. 61 through 67 to further limit the movement of the saw blade to a single plane.

The standard instrument 2100 of FIGS. 52 through 60 also includes an attachment 2112 site for securing an alignment rod to the instrument. In the particular implementation shown, the instrument includes a channel 2112 that can slidingly receive the alignment rod, and a knurled bolt 2113 for securing the alignment rod into the channel. Other structures and mechanisms could also be used to secure an alignment rod to the instrument if desired. In some implementations, the alignment rod can be used at appropriate points in the surgical procedure to confirm alignment of the instrumentation with respect to the patient's anatomy, such as the anatomic and/or mechanical axes of the patient's femur and/or tibia.

FIGS. 61 through 71 illustrate a non-limiting example of a method of using the patient-matched and standard instruments of FIGS. 47 through 67 to perform some of the steps of a bi-cruciate retaining arthroplasty procedure, although, in other implementations, instrumentation having some or all of the features of the described implementations could be used for other joint arthroplasty or other types of orthopaedic procedures.

Figure 61:
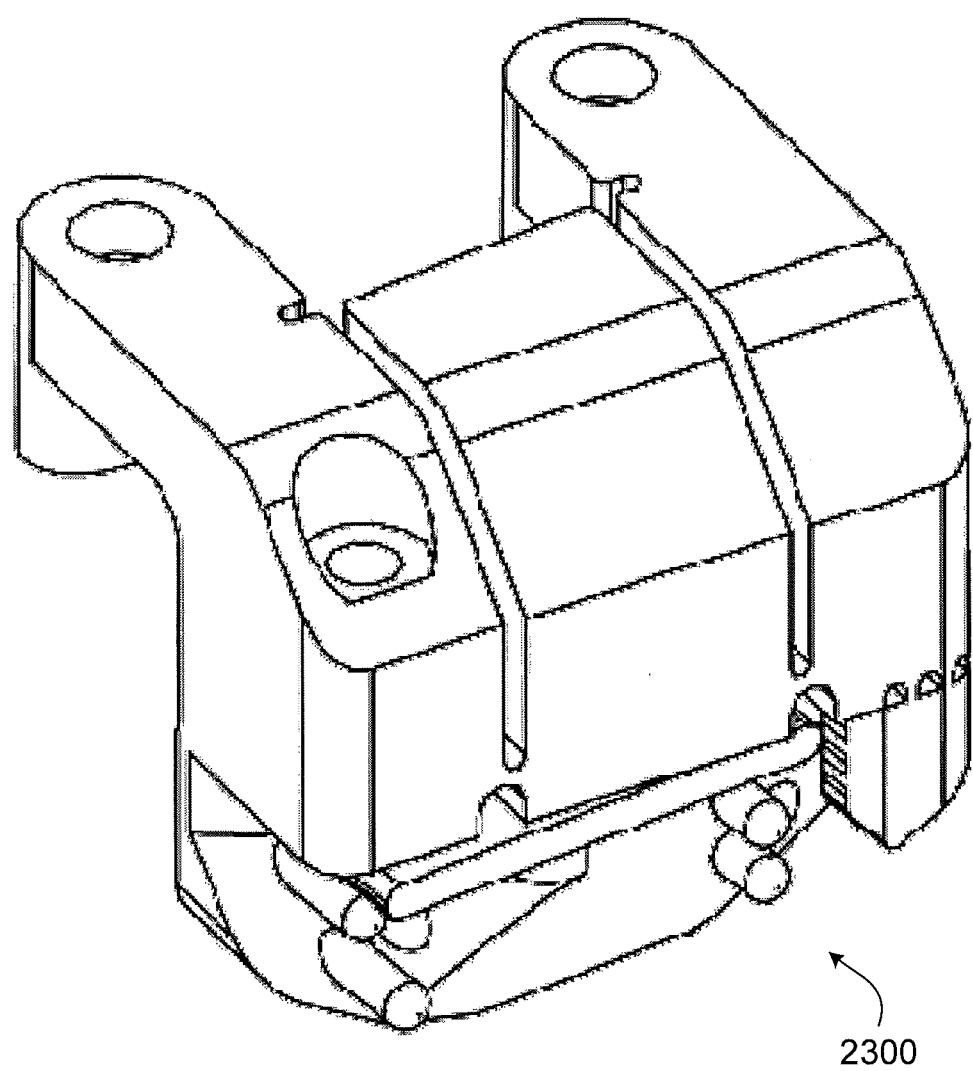
FIGS. 61 through 72 illustrate some of the steps of one example of an arthroplasty procedure using the instrumentation shown in FIGS. 47 through 67.

FIG. 61 shows a patient-matched instrument 2300 that has been customized to the anatomy of a specific patient such that the instrument conforms to or references the patient's anatomy (in this implementation, the right, proximal tibia) to establish a desired position and orientation of the instrument with respect to the patient's anatomy. In the particular implementation shown, the patient-matched instrument includes patient-matched contact surfaces on the anatomy facing surfaces on the instrument (not shown in this particular figure) that were established using MRI data and pre-selected positions and orientations of the desired resections to the bone (or desired final position and orientation of the tibial implant(s)) and was manufactured using selective laser sintering technologies, although, in other implementations, other data collection, processing, and manufacturing methods could be used to customize the instrument to the patient's anatomy.

Figure 52:
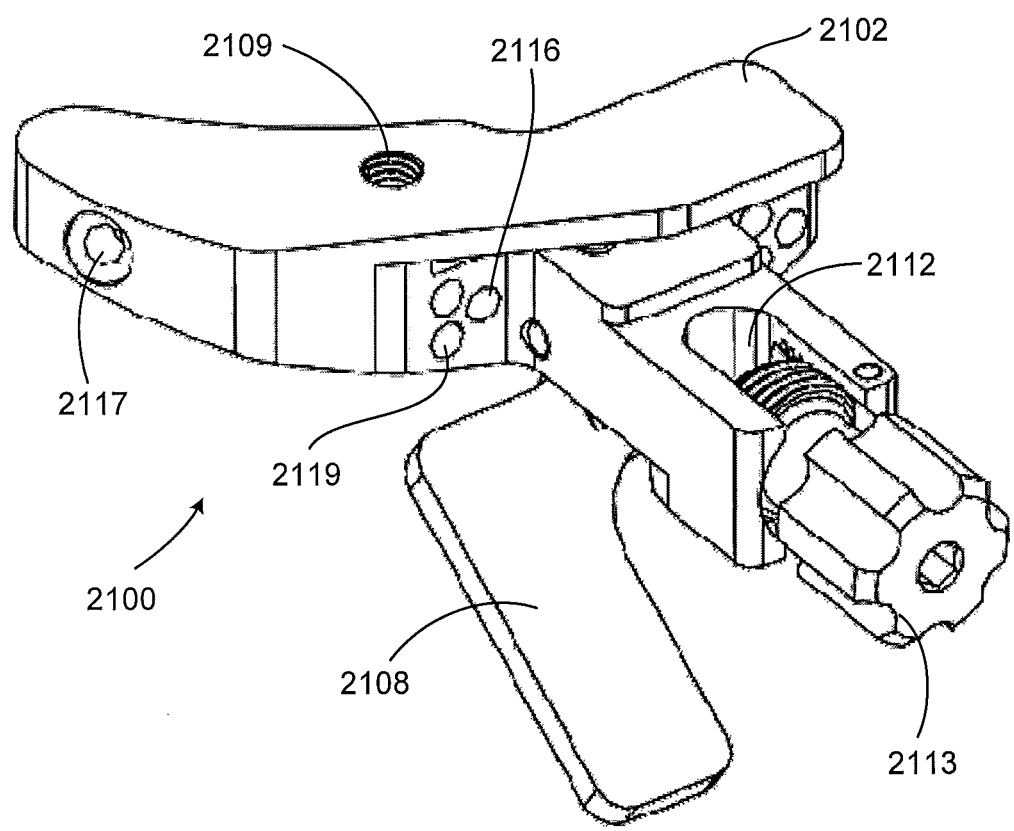
FIGS. 52 through 60 show various views of a standard, non-patient-matched instrument that can be used in conjunction with the patient-matched instruments of FIGS. 47 through 51.
Figure 53:
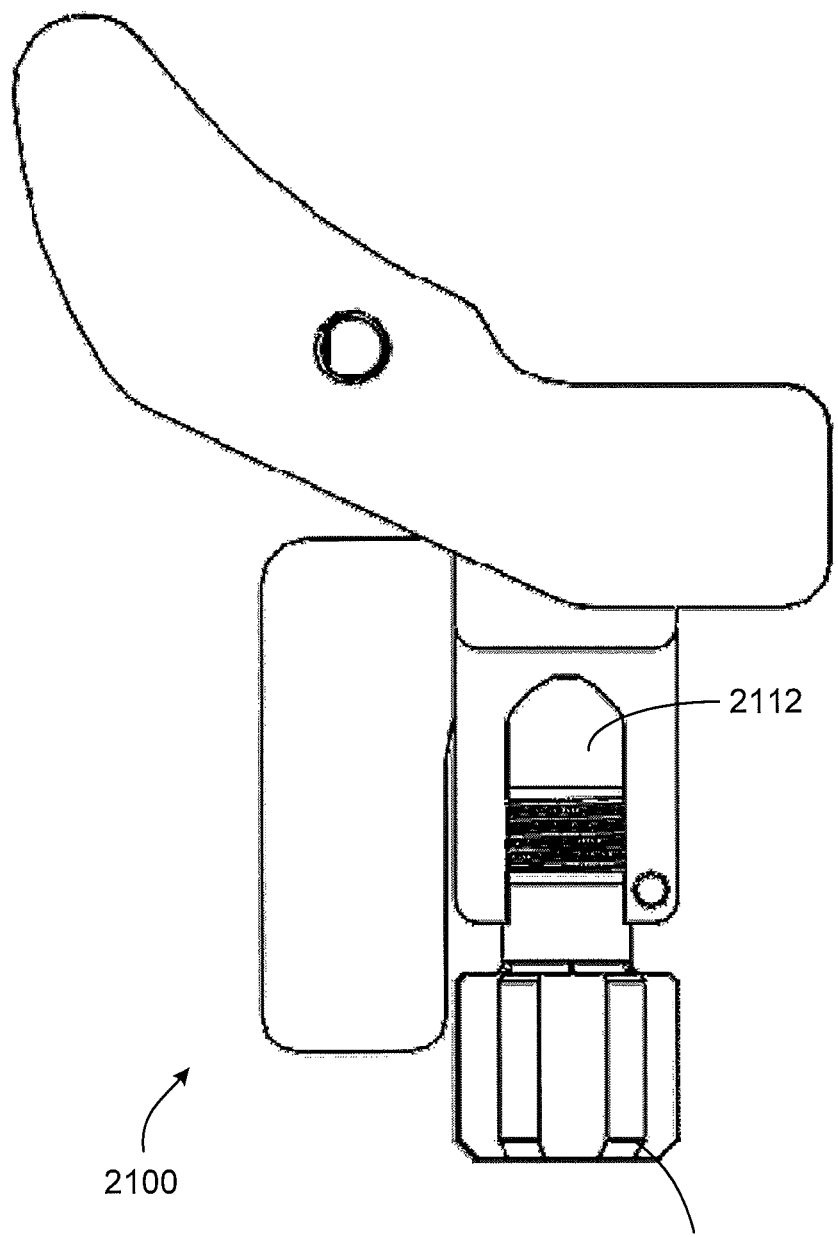
Figure 54:
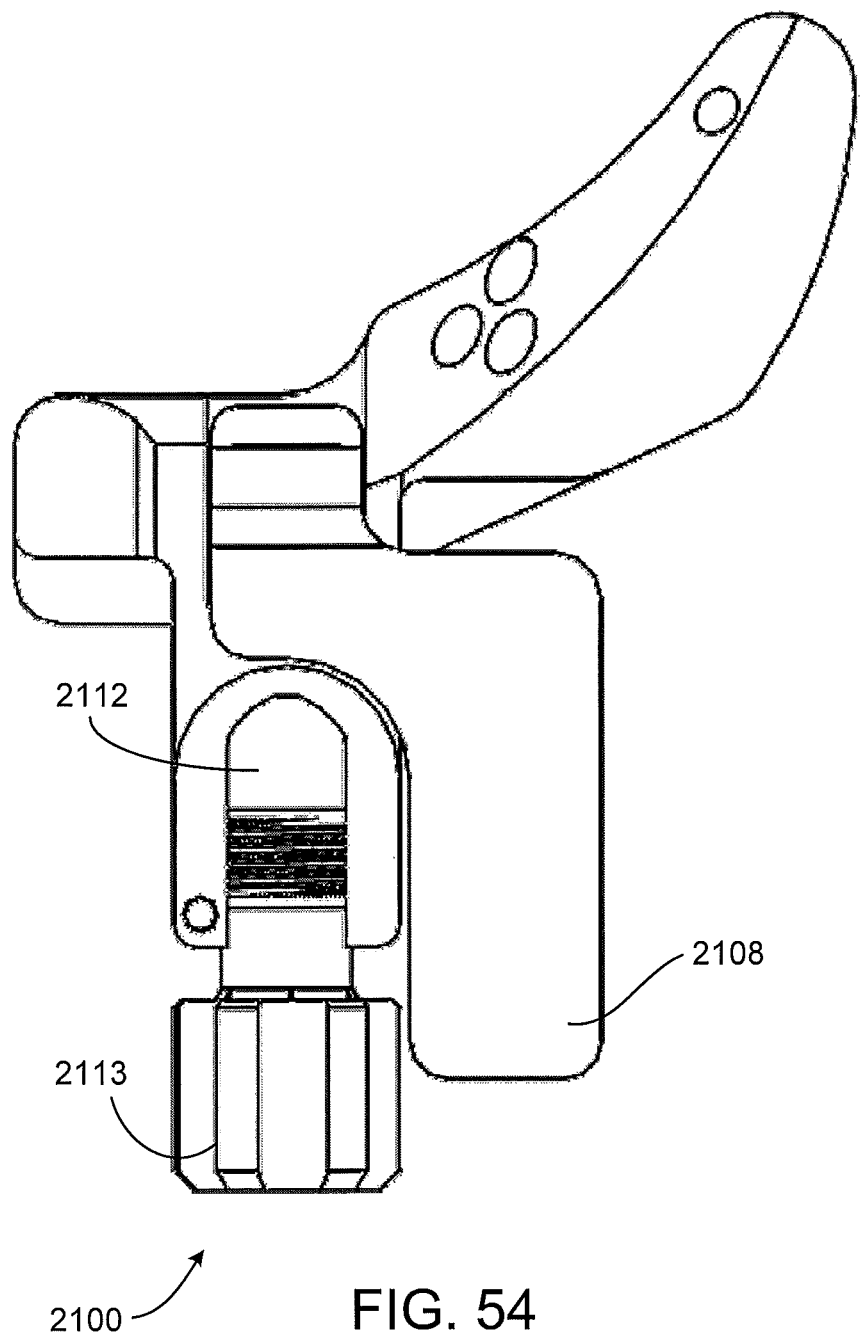
Figure 55:
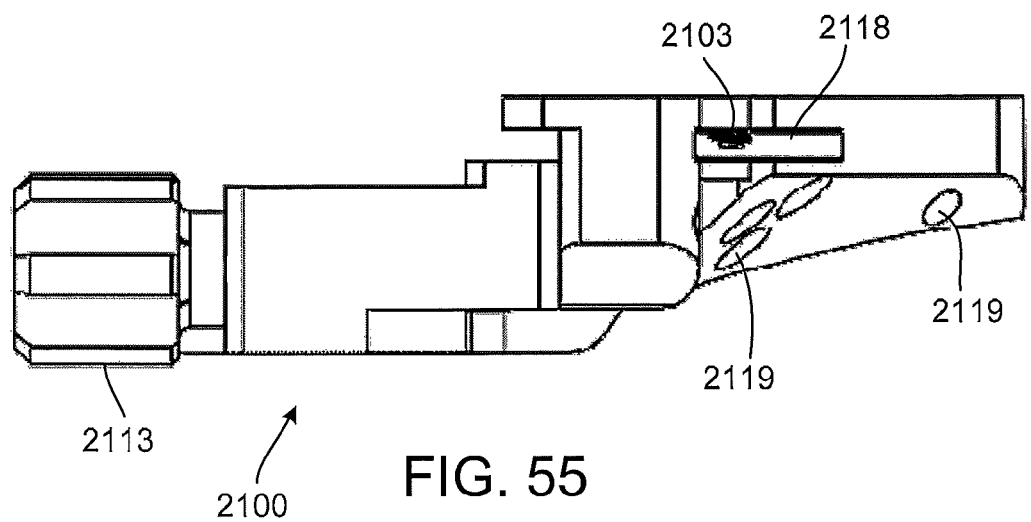
Figure 56:
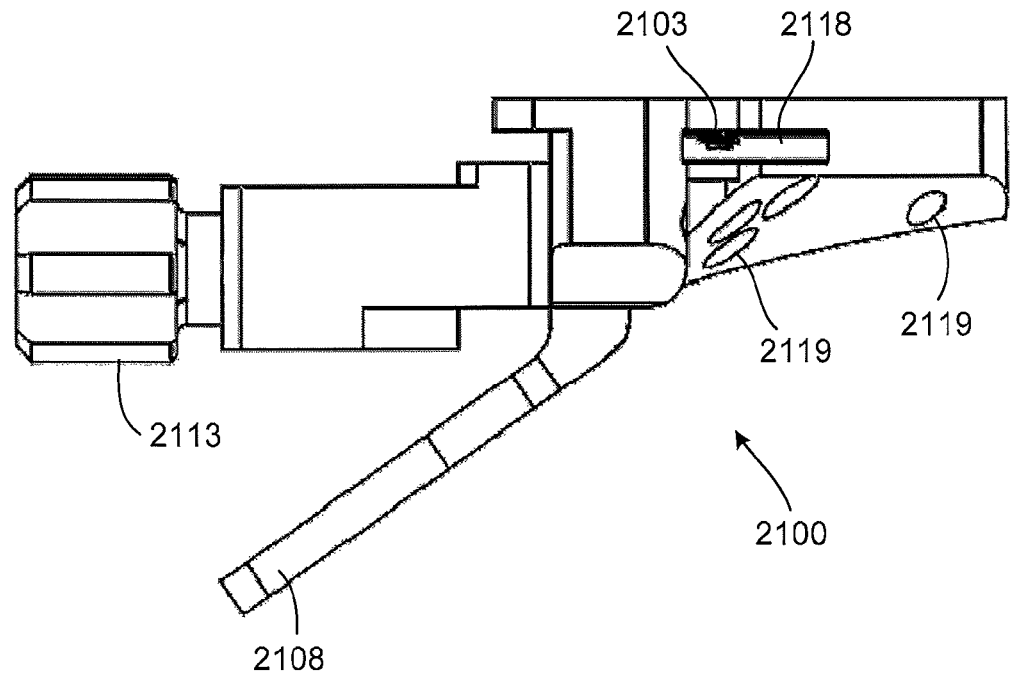
Figure 57:
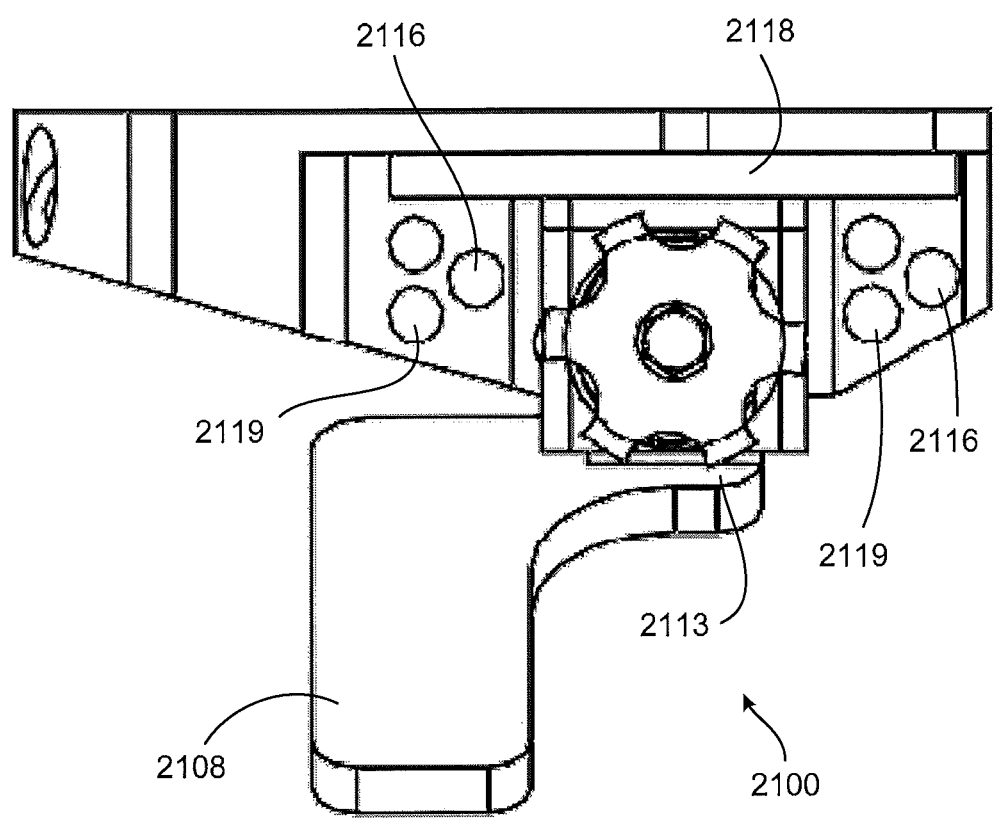
Figure 58:
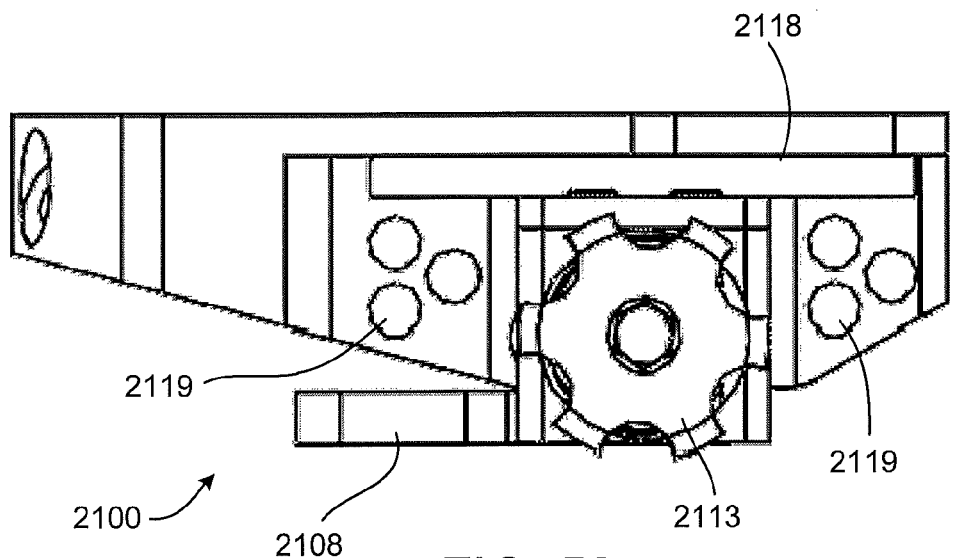
Figure 59:
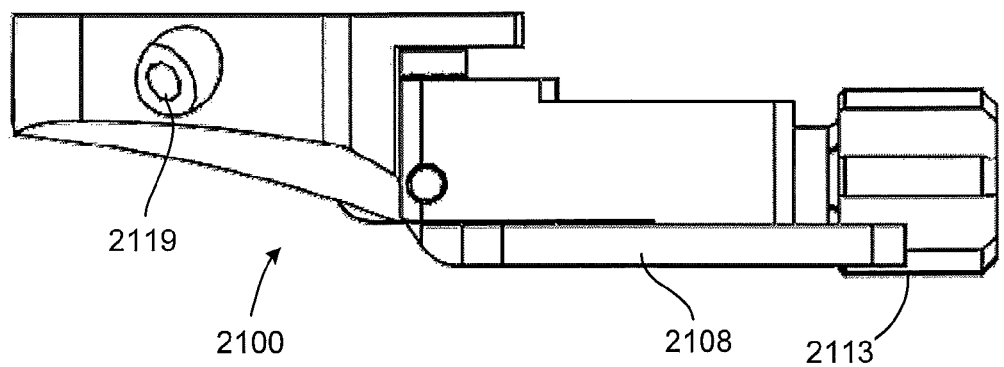
Figure 60:
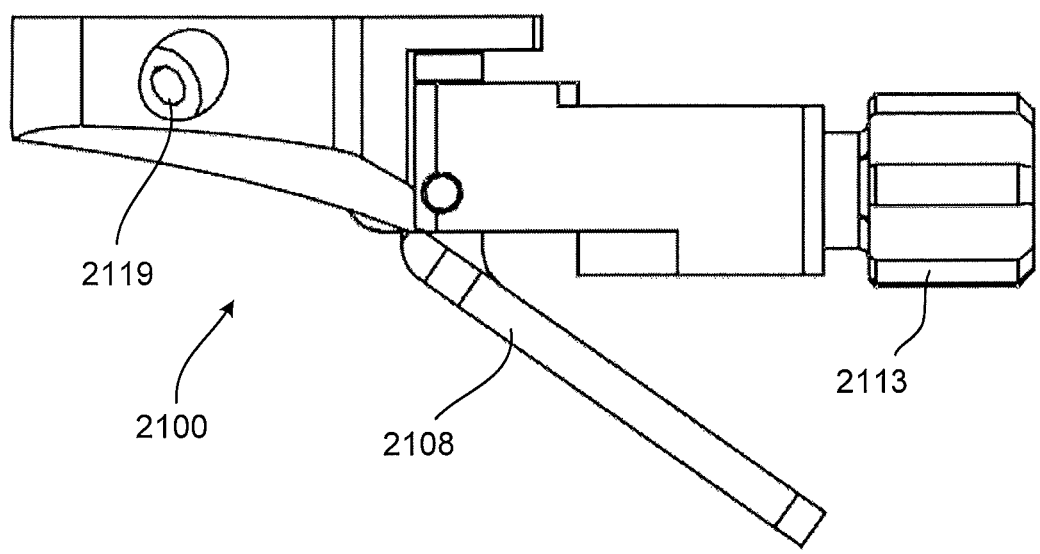
Figure 62:
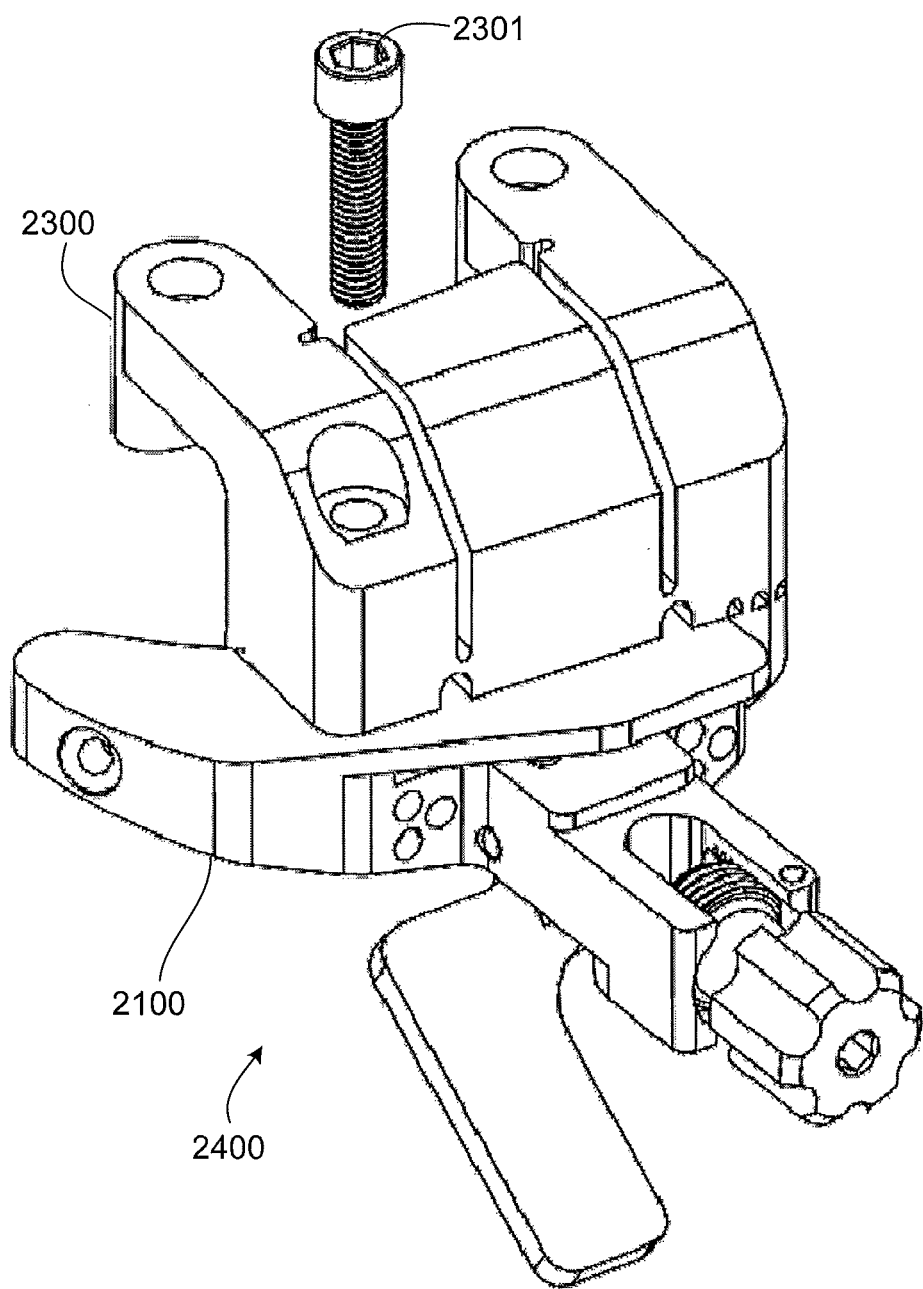
Figure 63:
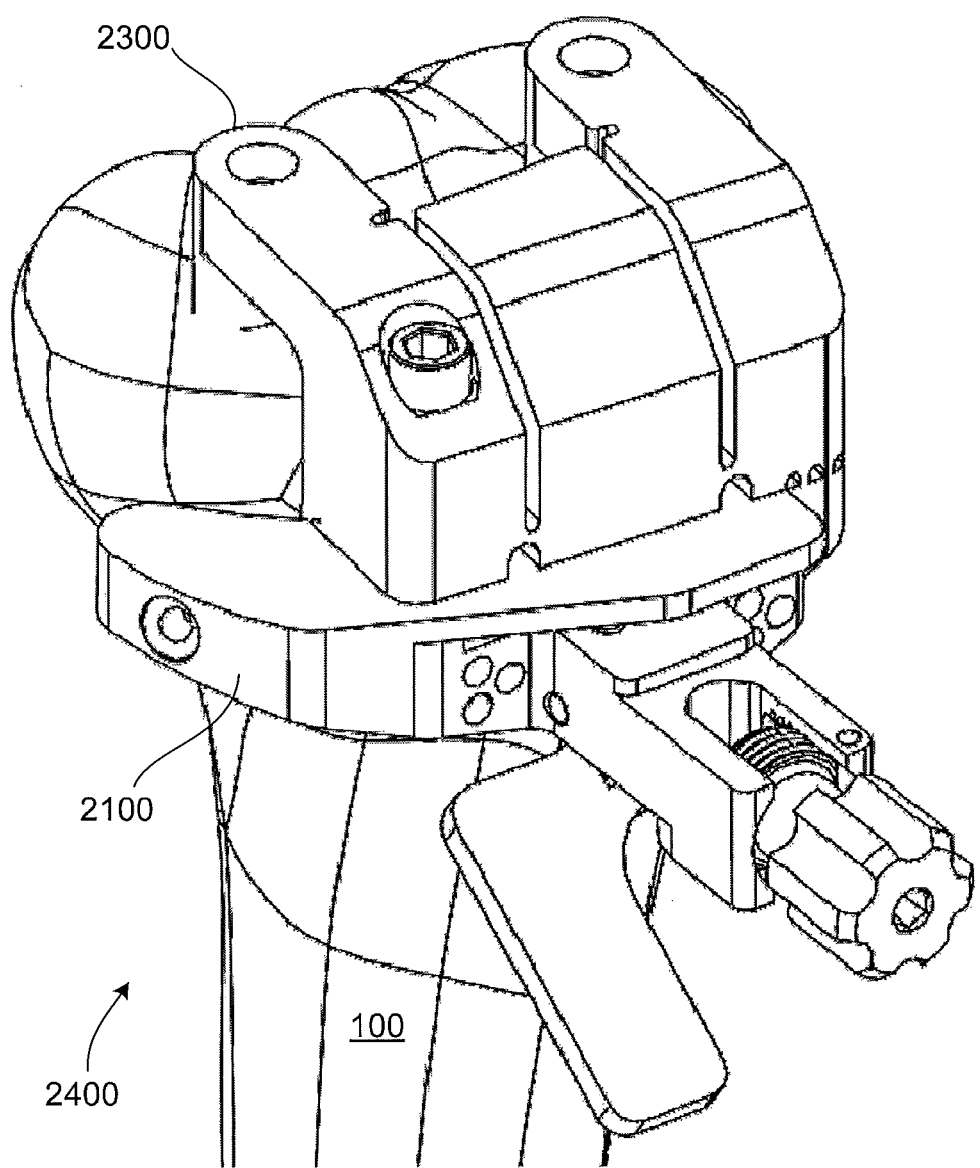

FIG. 62 shows the connection of the standard instrument 2100 of FIG. 52 to the patient-matched instrument 2300 of FIG. 61 using a mounting bolt 2301. In the particular implementation shown, the standard instrument 2100 is connected to the patient-matched instrument before positioning the construct on the patient's anatomy, although, in other implementations, the patient-matched instrument could be positioned on the anatomy before the standard instrument is connected. FIG. 63 illustrates the patient-matched instrument/standard instrument construct 2400 positioned on the patient's proximal tibia 100, using the conforming surfaces and/or point contact features on the bone-facing side of the patient-matched instrument to establish the proper position and orientation of the construct with respect to the patient's anatomy. If desired, the surgeon may confirm the proper position and orientation of the construct on the patient's tibia 100 at this point by attaching an alignment rod to the construct and checking alignment relative to the mechanical and/or anatomic axes of the patient's tibia and/or femur.

Figure 64:
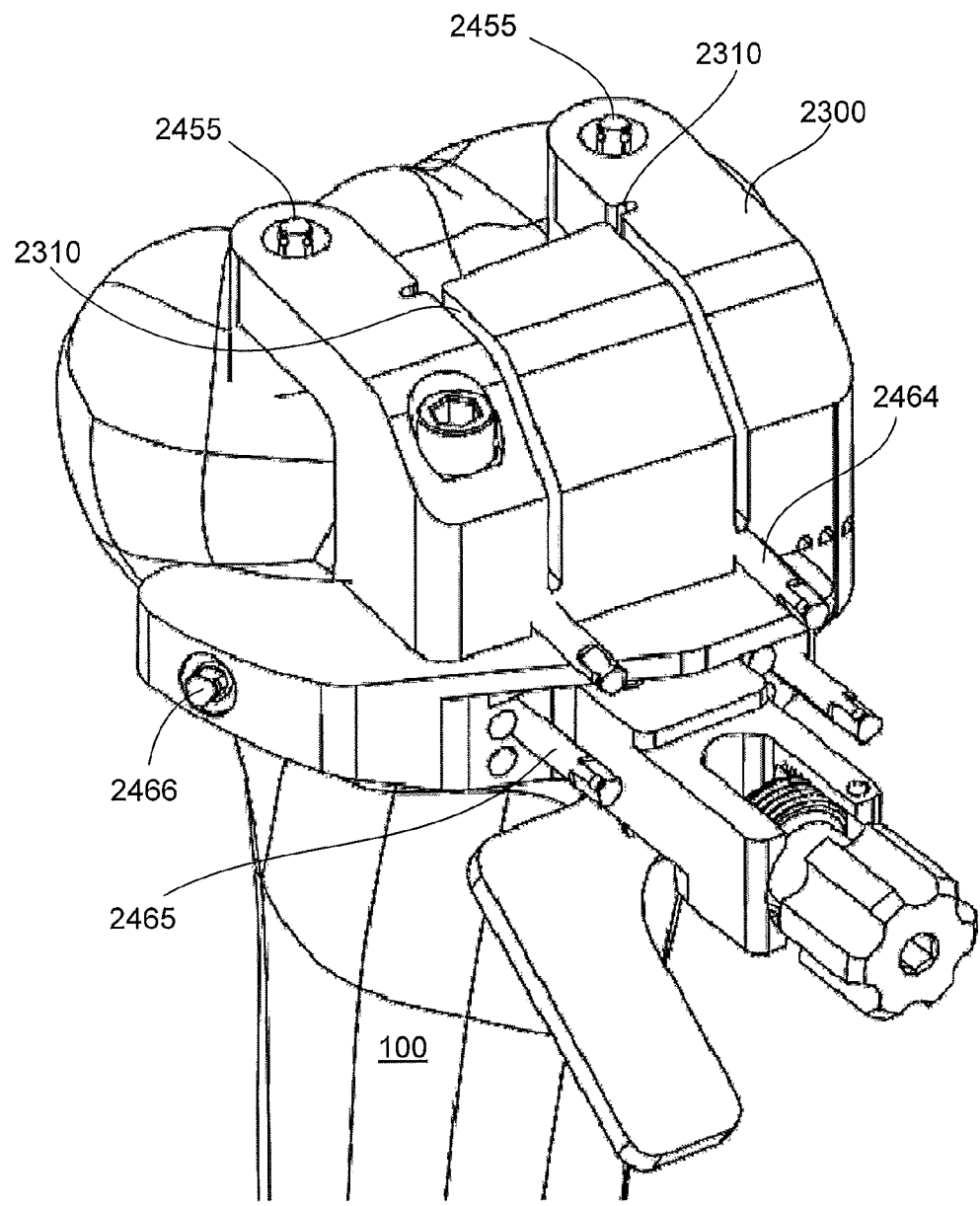

FIG. 64 shows the patient-matched/standard instrument 2400 construct secured to the patient's anatomy using several bone pins 2464, 2465. In this particular implementation, there are two vertical pins 2455 associated with the outriggers of the patient-matched instrument, two horizontal pins 2464 passing through the main body of the patient-matched instrument, two horizontal parallel pins 2465 passing first through standard instrument and second through the patient matched instrument (the reverse is an alternative implementation), and one oblique pin 2466 passing through the standard instrument. In other implementations, other combinations of pins or other fastening devices could be used to secure the construct to the patient's anatomy.

Figure 65:
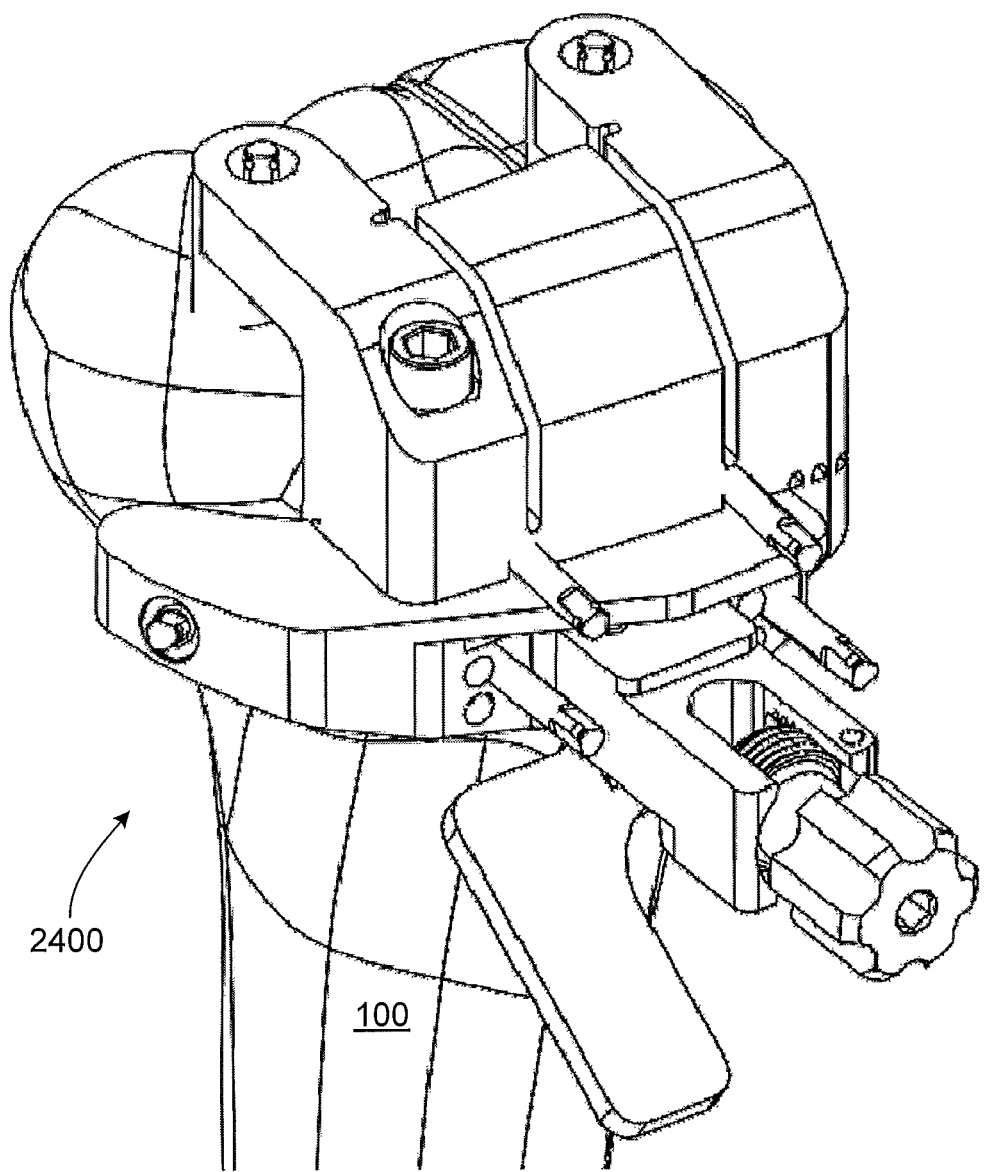
Figure 66:
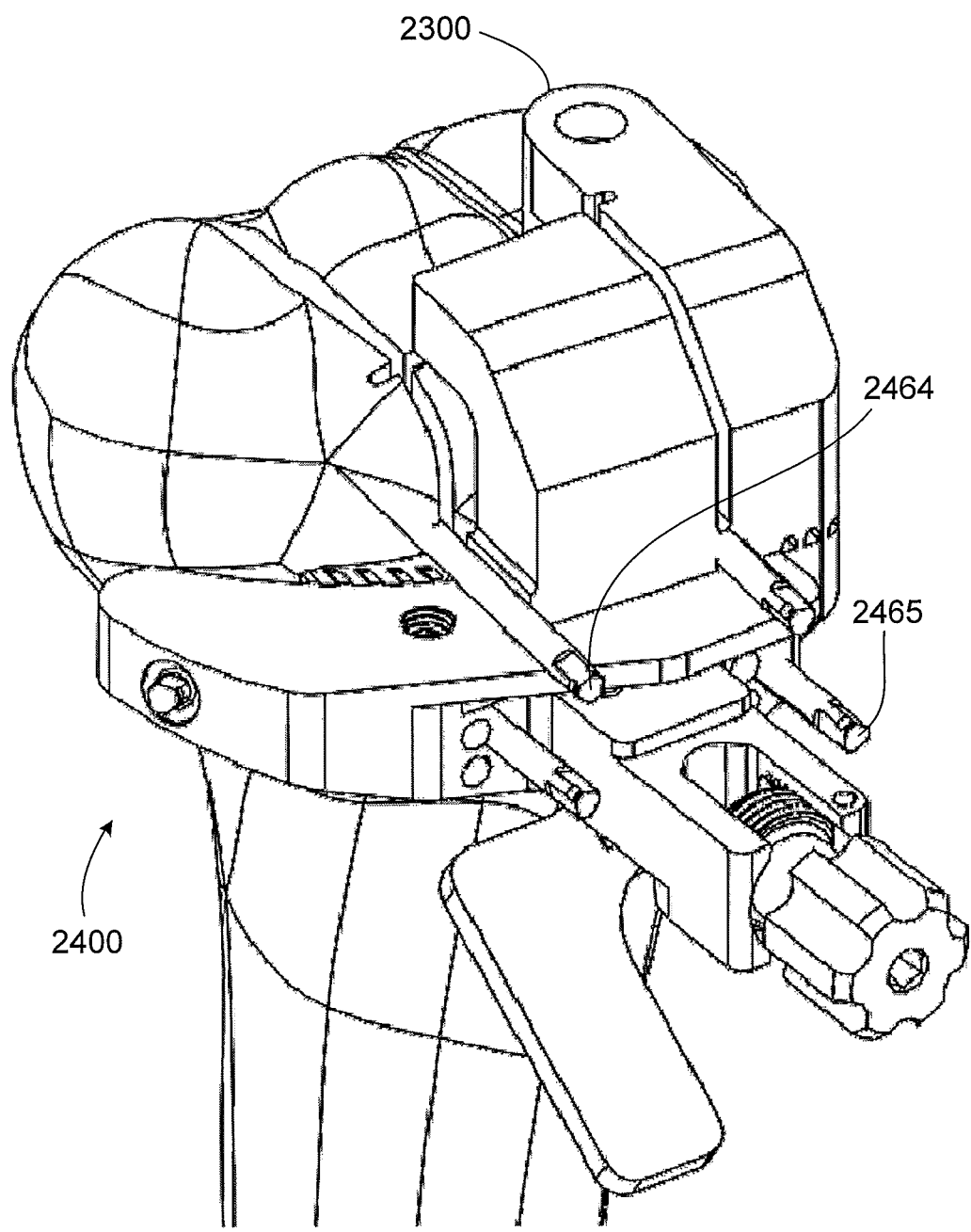
Figure 67:
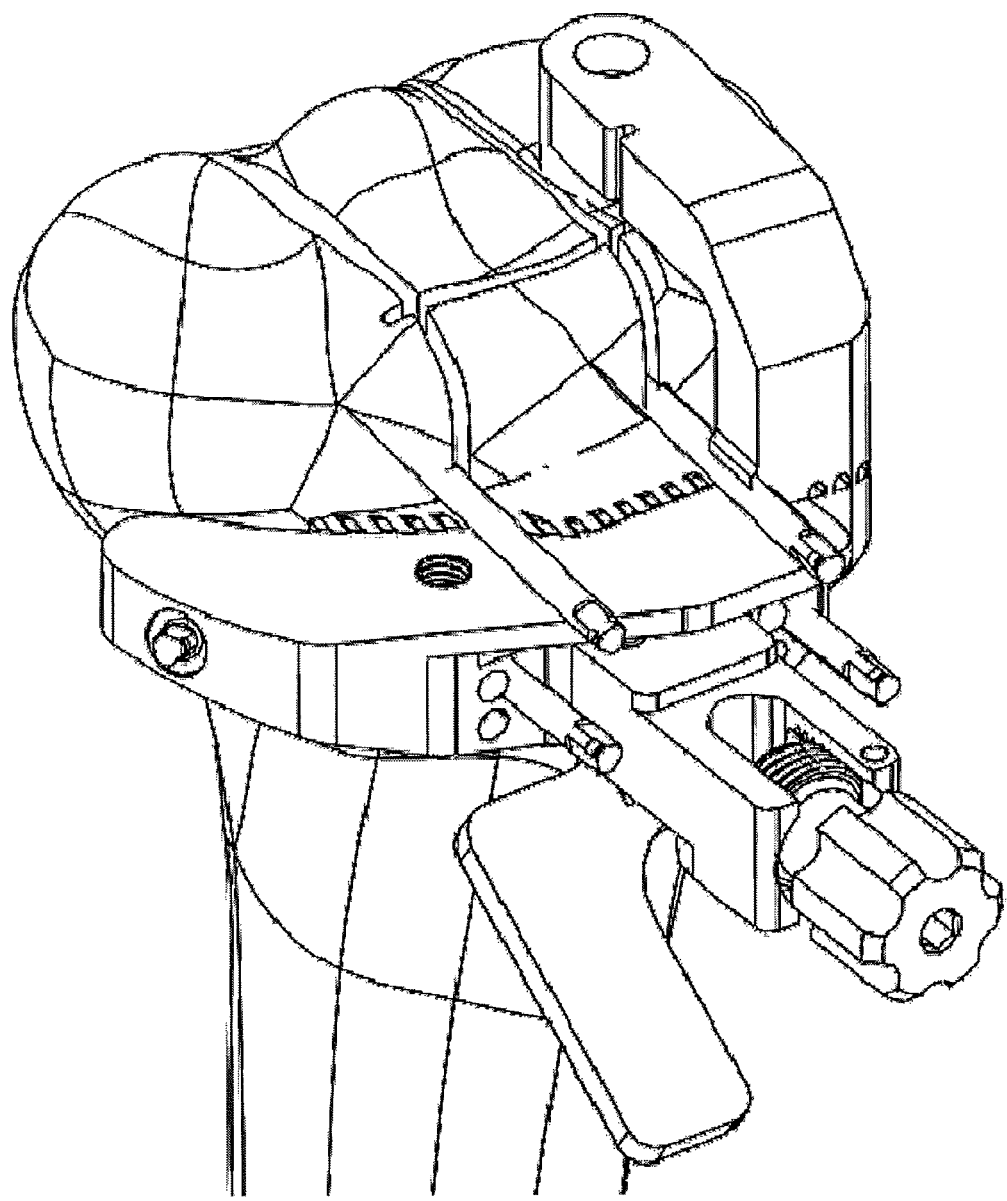
Figure 68:
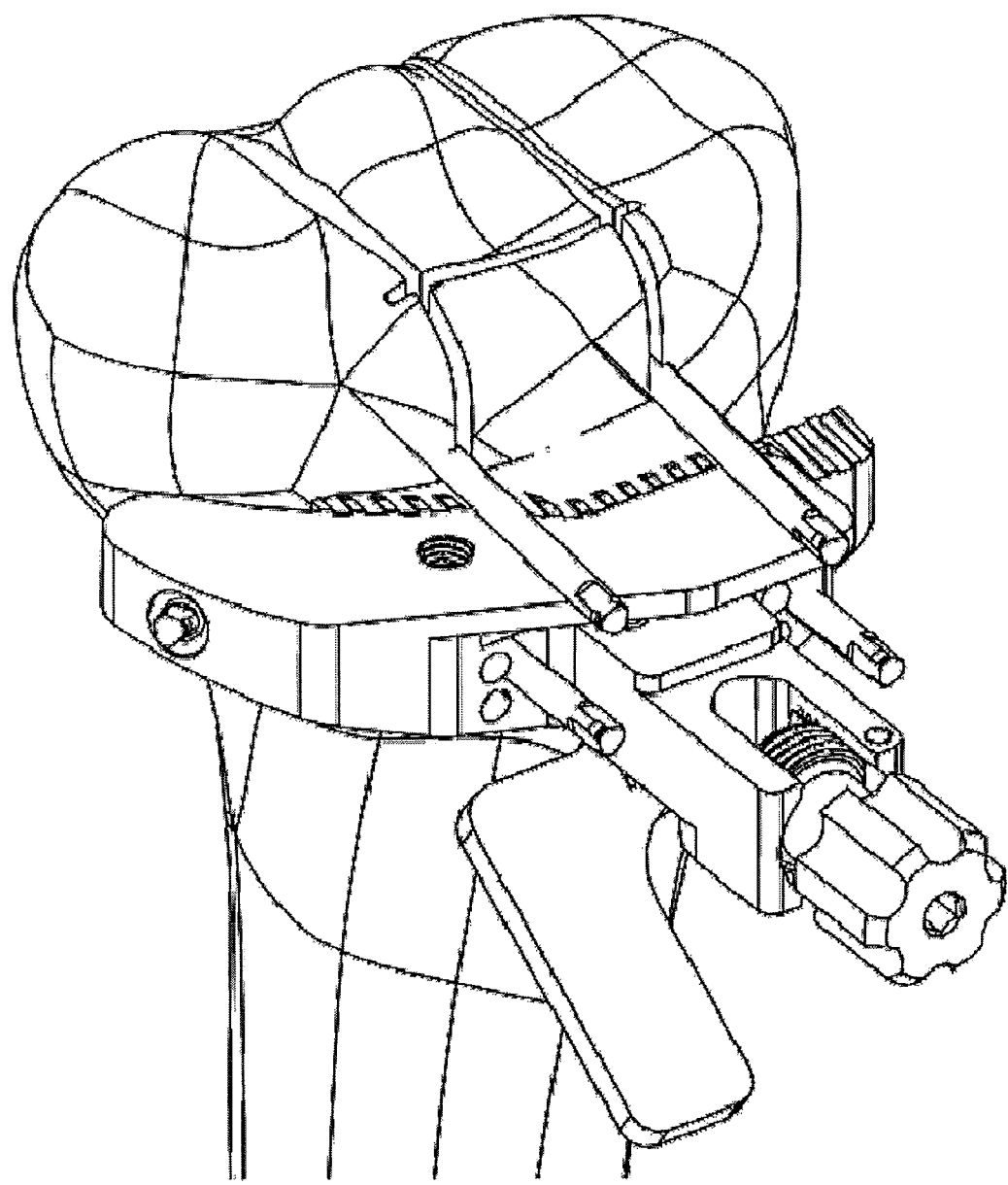
Figure 69:
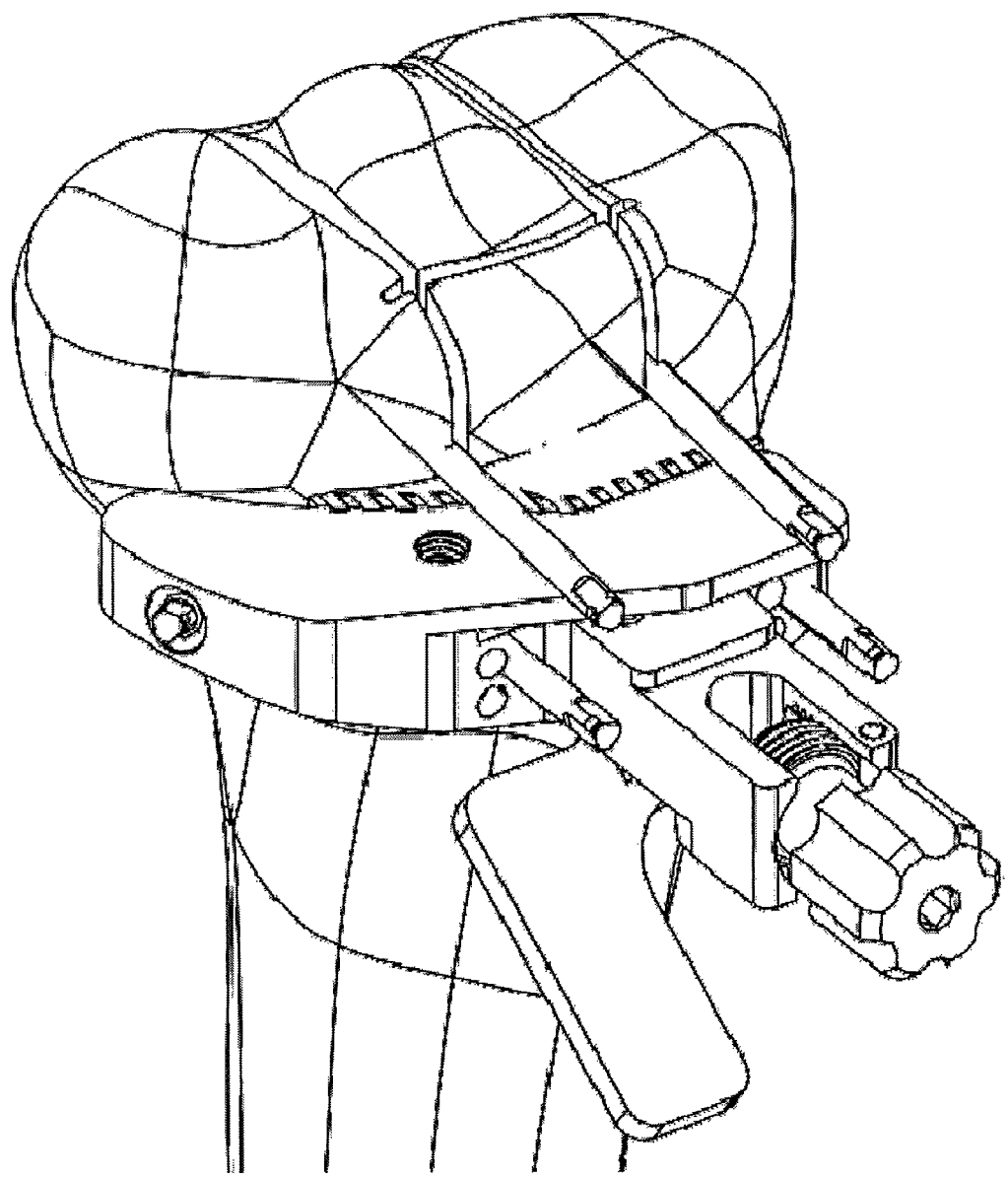

In the particular implementation shown, after the patient-matched/standard instrument construct is secured the proximal tibia 100, the guides 2310 incorporated into the patient-matched instrument 2300 are used to guide the vertical eminence resections and the anterior eminence vertical resection. In some implementations, a reciprocating saw is used for the vertical eminence resections and a chisel is used for the vertical anterior eminence resection. In the particular implementation shown, the horizontal pins 2464 that secure the patient-matched instrument to the tibia also function to limit the depth of cut of these resections. FIG. 65 illustrates the proximal tibia 100 and patient-matched/standard instrument construct 2400 after these resections have been completed.

As shown in FIGS. 66 through 69, after these resections are completed, the patient-matched instrument 2300 can be unbolted from the standard instrument and portions of the patient-matched instrument 2300 that are no longer needed could be broken away along frangible connections. In other implementations, the patient-matched instrument need not be frangible, and could be designed to be partially or totally removed from the construct 2400 in other manners. For instance, in some implementations, the bone pins 2464, 2465 could function as place holders to allow the entire patient-matched/standard instrument construct 2400 to be removed from the anatomy, disassembled, and only the standard instrument replaced onto the anatomy. In still other implementations, the patient-matched instrument could first be positioned on the anatomy without the standard instrument, and could be used to make the initial resections and position the bone pins, and then removed from the patient's anatomy and replaced with the standard instrument.

Figure 70:
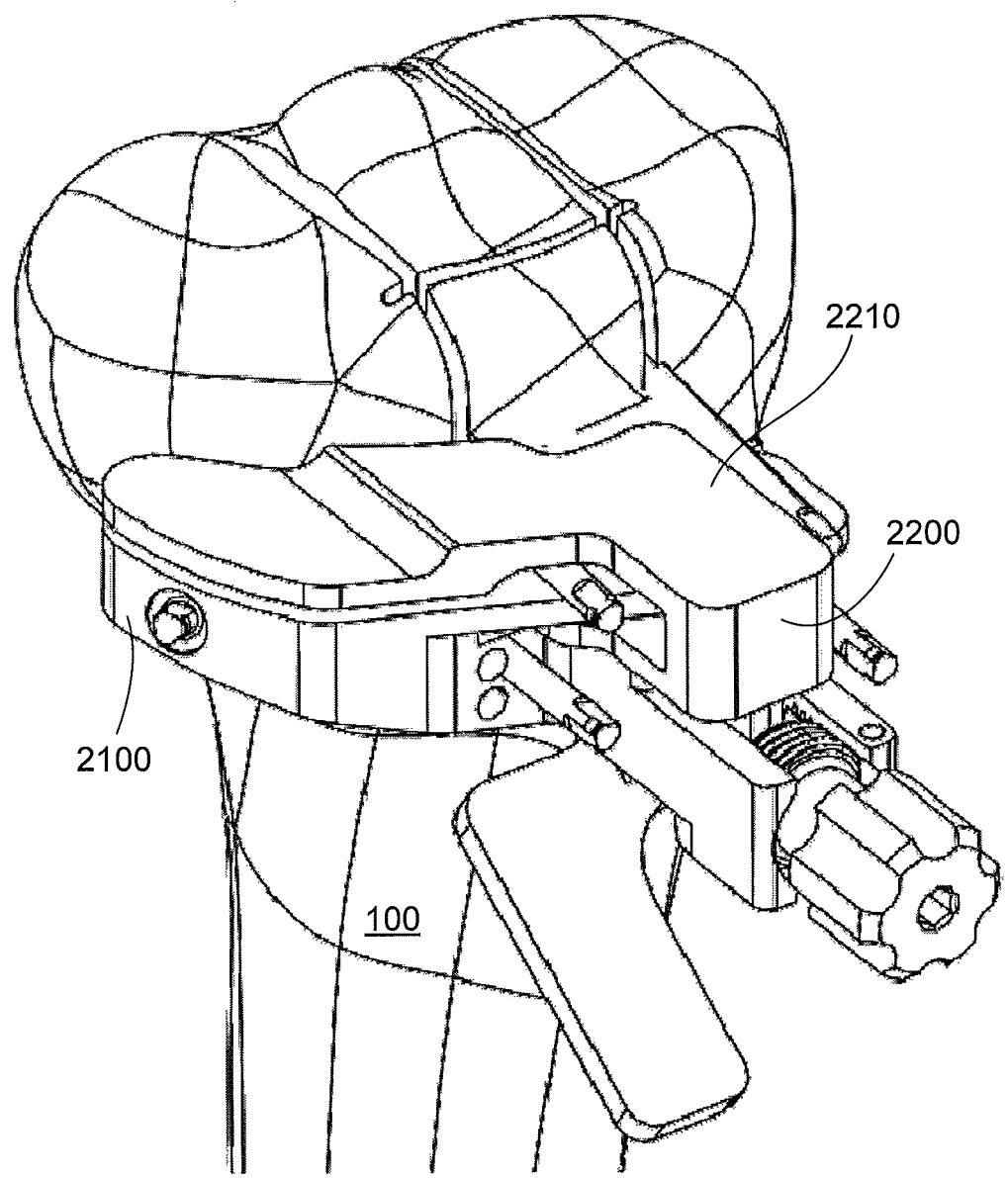
Figure 71:
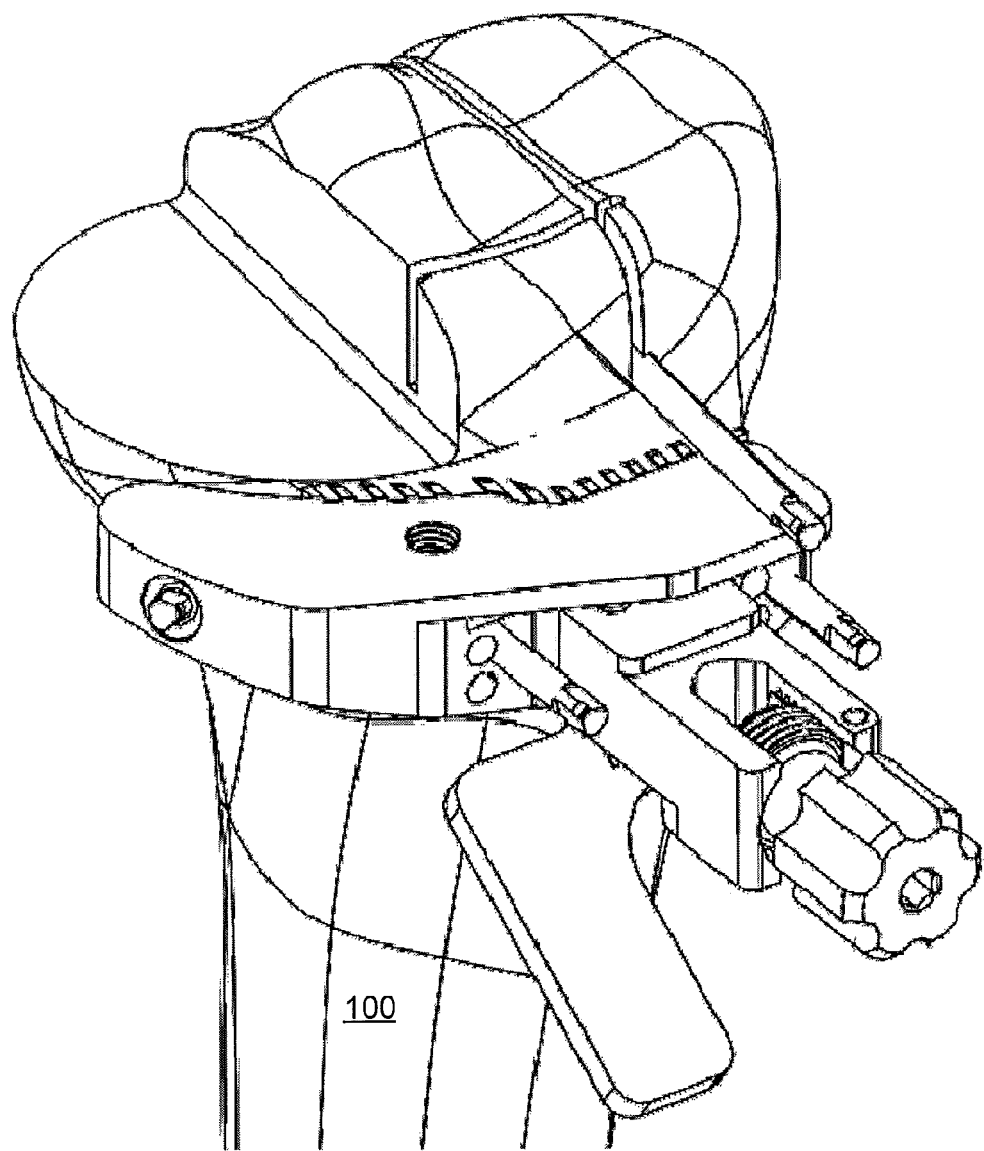

In some implementations, removal of portions of the patient-matched instrument facilitates access to other features and/or functionality of one or both of the patient-matched or standard instruments. For instance, in the particular implementation illustrated, particularly FIG. 70, removal of portions of the patient-matched instrument allows the supplemental component 2200 (FIG. 73) to be secured to the standard instrument 2100. As shown in FIG. 70, the supplemental component 2200 is configured to accommodate the medial horizontal pin while also defining a planar surface 2210 that interfaces with a superior surface on the cutting blade to help guide the horizontal plateau resection. In the particular implementation shown, the planar superior surface 2210 of the standard instrument 2200 (in conjunction with the planar inferior surface of the supplemental component) control the depth and posterior slope of the resection and the horizontal pin controls the medial extent and internal/external rotation of the resection. Other guide structures and techniques are also possible. For instance, in some implementations, the medial plateau resection could be performed without the use of the supplemental component. FIG. 71 shows the tibia 100 after the medial plateau resection.

Figure 72:
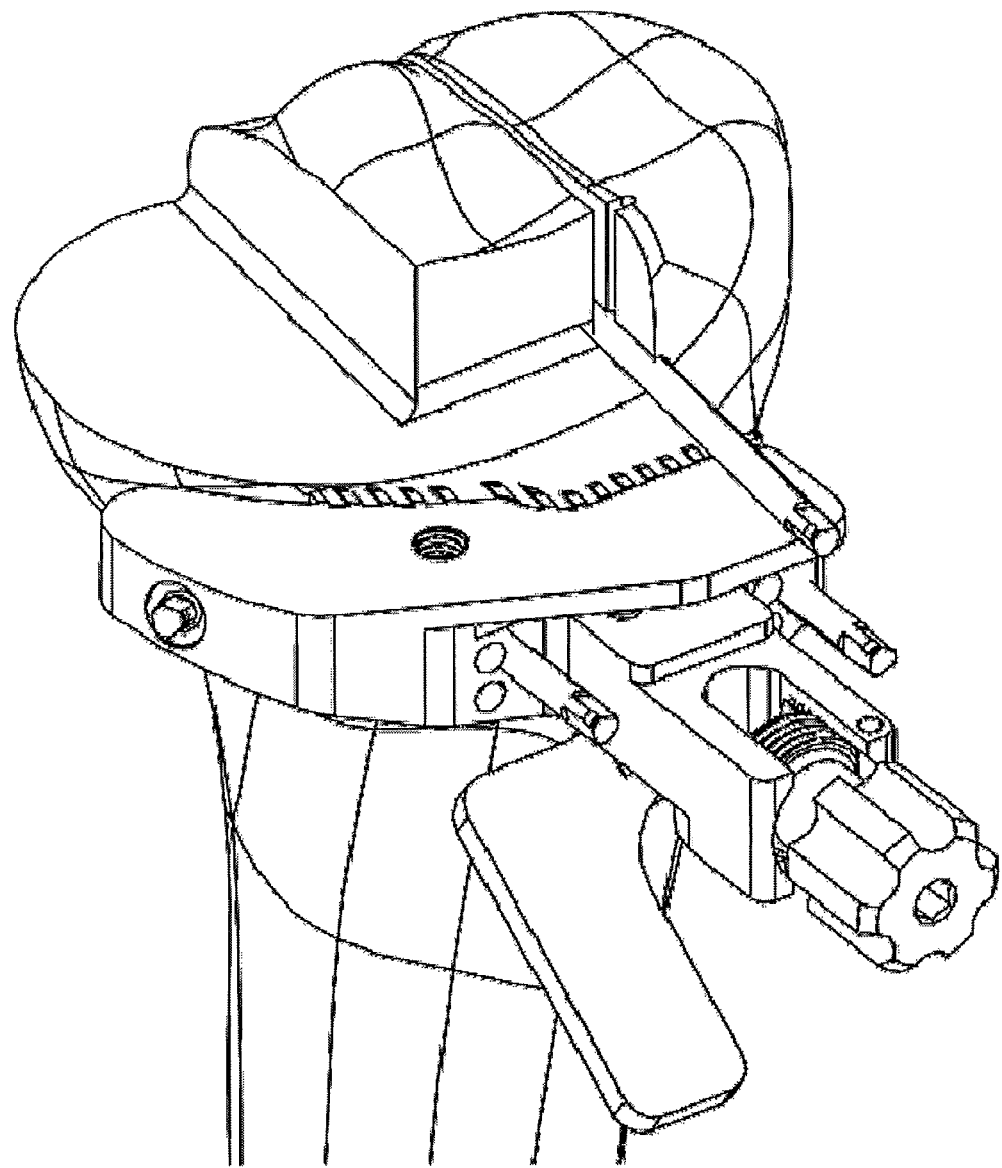
Figure 73:
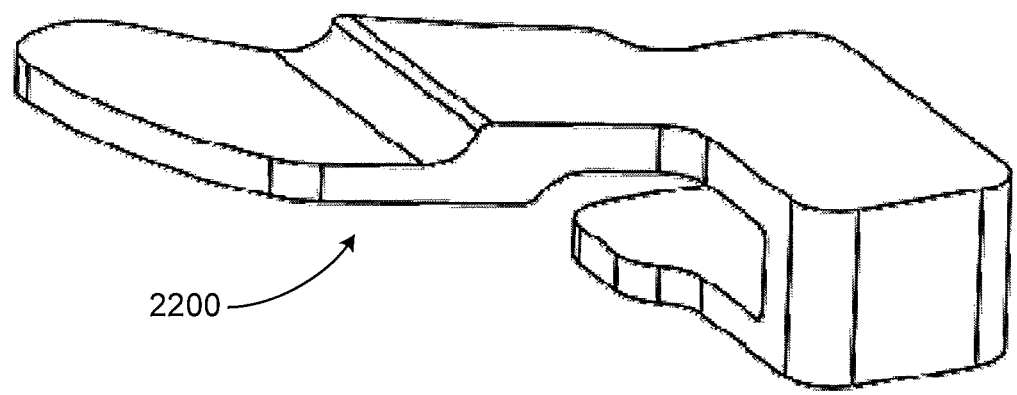
FIG. 73 shows a view of a supplemental instrument that can be used in conjunction with the standard instrument of FIGS. 52 through 60.

As shown in FIG. 72, the standard component, particularly the planar superior surface of the standard component, may be used in some implementations to also guide the horizontal anterior eminence resection. In some implementations, the vertical and/or horizontal anterior eminence resections are not performed until after the medial resections have been evaluated and/or balanced.

FIGS. 61 through 72 only show some of the steps of a bi-cruciate retaining knee arthroplasty procedure, and the remainder of the procedure may be completed using these or other standard and/or patient-matched instrumentation.

Additions, deletions, substitutions, modifications and other changes may be made to the non-limiting implementations described herein without departing from the scope or spirit of the present disclosure.

What is claimed is:

1. A patient matched tibial cutting block comprising:
a surface or point contact feature adapted to at least partially conform to or reference a patient specific anatomy wherein the patient specific surface is established in presurgical planning based on imaging data of the patient's anatomy;
a plurality of eminence-preserving guide slots configured for guiding the movement of cutting tools relative to the patient specific anatomy;
a plurality of plateau guide slots configured for guiding the movement of cutting tools relative to the patient specific anatomy;
further comprising one or more apertures configured to guide the placement of provisional fixation pins, and wherein the apertures contain position control elements configured to control the depth of the provisional fixation pins; and
wherein the plurality of guide slots include surfaces that facilitate horizontal medial and lateral plateau resections and medial and lateral vertical eminence resections of a proximal tibia.

2. The patient matched tibial cutting block of claim 1, further comprising retractor features detachably coupled to the cutting block and configured to retain soft tissue away from the guide slots.

3. A patient specific tibial cutting guide comprising:
a central portion configured to at least partially overlay anterior and superior portions of the proximal tibia;
a plurality of outrigger portions extending from the central portion and configured to at least partially overlay medial and lateral articulation surfaces of the proximal tibia; and a plurality of wing portions extending medially and laterally from the central portion and configured to extend at least partially around medial and lateral sides of an anterior face of the proximal tibia, wherein the central portion and the plurality of outrigger portions define guides configured for guiding a cutting tool to form vertical and anterior eminence-preserving resections of the proximal tibia and the plurality of wing portions define guide slots for guiding a cutting tool to form horizontal plateau resections of the proximal tibia.

4. The patient specific tibial cutting guide of claim 3, wherein one or more of the central portion, the plurality of outrigger portions, and the plurality of wing portions comprises one or more surfaces or point contacts adapted to at least partially conform to or reference a corresponding surface of the proximal tibia, wherein the one or more surfaces is established in pre-surgical planning based on imaging data of the patient's proximal tibia.

5. The patient specific tibial cutting guide of claim 3, further comprising one or more apertures defined in the central portion or the plurality of outrigger portions and configured to guide the placement of provisional fixation pins.

6. The patient specific tibial cutting guide of claim 3, wherein the plurality of wing portions comprise retractor features configured to retain soft tissue away from the guide slots.

7. The patient specific tibial cutting guide of claim 3, further comprising reinforcing elements at least partially embedded in one or more of the central portion, the plurality of outrigger portions, or the plurality of wing portions.

8. A system comprising:
a patient matched cutting block comprising a surface or point contact feature adapted to at least partially conform to or reference a patient specific anatomy; and a plurality of guide slots configured for guiding the movement of cutting tools relative to the patient specific anatomy to form plateau and eminence resections of the patient specific anatomy; or a patient specific tibial cutting guide comprising a central portion configured to at least partially overlay anterior and superior portions of the proximal tibia, a plurality of outrigger portions extending from the central portion and configured to at least partially overlay medial and lateral articulation surfaces of the proximal tibia, and a plurality of wing portions extending medially and laterally from the central portion and configured to extend at least partially around medial and lateral sides of an anterior face of the proximal tibia, wherein the central portion and the plurality of outrigger portions define guides configured for guiding a cutting tool to form vertical and anterior eminence-preserving resections of the proximal tibia and the plurality of wing portions define guide slots for guiding a cutting tool to form horizontal plateau resections of the proximal tibia; and
a standard instrument attachable to the patient matched cutting block or the patient specific tibial cutting guide to assist in the configuration of and guidance of a cutting tool during a bone resection procedure.

9. A method of resectioning a proximal tibia, comprising:
securing a patient matched instrument to a patient's proximal tibia;
using the patient matched instrument to guide one or more cutting guides relative to the proximal tibia to form horizontal medial and lateral plateau resections, medial and lateral vertical eminence-preserving resections.

10. The method of claim 9, wherein securing the patient matched instrument to the patient's proximal tibia comprises using one or more fixation pins to secure the instrument in a particular location relative to the tibia, and wherein one or more holes formed in the tibia during the securing step are removed during resectioning.

11. A kit comprising:
a patient matched cutting block comprising a surface or point contact feature adapted to at least partially conform to or reference a patient specific anatomy; and a plurality of guide slots configured for guiding the movement of cutting tools relative to the patient specific anatomy to form plateau and eminence resections of the patient specific anatomy;
a patient specific tibial cutting guide comprising a central portion configured to at least partially overlay anterior and superior portions of the proximal tibia, a plurality of outrigger portions extending from the central portion and configured to at least partially overlay medial and lateral articulation surfaces of the proximal tibia, and a plurality of wing portions extending medially and laterally from the central portion and configured to extend at least partially around medial and lateral sides of an anterior face of the proximal tibia, wherein the central portion and the plurality of outrigger portions define guides configured for guiding a cutting tool to form vertical and anterior eminence resections of the proximal tibia and the plurality of wing portions define guide slots for guiding a cutting tool to form horizontal plateau resections of the proximal tibia; and
a standard instrument attachable to the patient matched cutting block or the patient specific tibial cutting guide to assist in the configuration of and guidance of a cutting tool during a bone resection procedure.

12. The patient matched tibial cutting block of claim 3, wherein each of the plurality of eminence-preserving guides extend in the same anterior-posterior direction.

13. The patient matched tibial cutting block of claim 8, wherein each of the plurality of eminence-preserving guides extend in the same anterior-posterior direction.

14. The patient specific tibial cutting guide of claim 6, wherein the retractor portion extends from the distal end of each wing.

* * * * *